US012674170B2

(12) United States Patent
Aoki et al.

(10) Patent No.: US 12,674,170 B2
(45) Date of Patent: Jul. 7, 2026

(54) APTAMER FOR IL-21 AND USE THEREOF

(71) Applicant: RIBOMIC INC, Tokyo (JP)

(72) Inventors: Kazuteru Aoki, Tokyo (JP); Marie Mitsui, Tokyo (JP)

(73) Assignee: RIBOMIC INC., Tokyo (JP)

( * ) Notice: Subject to any disclaimer, the term of this patent is extended or adjusted under 35 U.S.C. 154(b) by 796 days.

(21) Appl. No.: 18/010,945

(22) PCT Filed: Jun. 17, 2021

(86) PCT No.: PCT/JP2021/023023
§ 371 (c)(1),
(2) Date: Dec. 16, 2022

(87) PCT Pub. No.: WO2021/256530
PCT Pub. Date: Dec. 23, 2021

(65) Prior Publication Data
US 2023/0235333 A1 Jul. 27, 2023

(30) Foreign Application Priority Data

Jun. 17, 2020 (JP) ................................. 2020-104831

(51) Int. Cl.
*C12N 15/115* (2010.01)
*C12N 15/10* (2006.01)
*G01N 33/50* (2006.01)

(52) U.S. Cl.
CPC ........ *C12N 15/115* (2013.01); *C12N 15/1048* (2013.01); *G01N 33/5041* (2013.01); *C12N 2310/16* (2013.01); *C12N 2310/313* (2013.01); *C12N 2310/322* (2013.01); *C12N 2310/3515* (2013.01); *C12N 2310/53* (2013.01)

(58) Field of Classification Search
CPC .............. C12N 15/115; C12N 15/1048; C12N 2310/16; C12N 2310/313; C12N 2310/322; C12N 2310/3515; C12N 2310/53; C12N 2310/315; C12N 2310/317; C12N 2310/321; G01N 33/5041; A61K 31/7105; A61K 31/7088; A61P 11/00; A61P 9/12; A61P 43/00
See application file for complete search history.

(56) References Cited

FOREIGN PATENT DOCUMENTS

| | | |
|---|---|---|
| JP | 6359921 B2 | 7/2018 |
| WO | 91/19813 A1 | 12/1991 |
| WO | 94/08050 A1 | 4/1994 |
| WO | 95/07364 A1 | 3/1995 |
| WO | WO-2019093497 A1 * | 5/2019 ......... A61K 31/7088 |

OTHER PUBLICATIONS

Avino et al. Thrombin binding aptamer, more than a simple aptamer: chemically modified derivatives and biomedical applications. Current pharmaceutical design, 18(14), 2036-2047. (Year: 2012).*
Ribomic, Presentation of research results on the development of innovative therapeutic agents for pulmonary arterial hypertension using anti-IL-21 aptamers (from IDS) (Year: 2019).*
Hashimoto-Kataoka, T et al. 2015. Interleukin-6/interleukin-21 signaling axis is critical in the pathogenesis of pulmonary arterial hypertension. Proceedings of the National Academy of Sciences, 112(20), E2677-E2686. (Year: 2015).*
Hashimoto-Kataoka et al., Interleukin-6/interleukin-21 signaling axis is critical in the pathogenesis of pulmonary arterial hypertension, Proc. Natl. Acad. Sci. U. S. A., 112(20):E2677-86 (2015).
International Application No. PCT/JP2021/023023, International Preliminary Report on Patentability, mailed Sep. 8, 2022.
International Application No. PCT/JP2021/023023, International Search Report and Written Opinion, mailed Jul. 27, 2021.
Ribomic, Presentation of research results on the development of innovative therapeutic agents for pulmonary arterial hypertension using anti-IL-21 aptamers, 3 ((2019), Online available at <URL:https://ss14.eir-parts.net/doc/4591/tdnet/1665714/00.pdf>.
Nakaoka et al., Development of innovative treatment method for pulmonary arterial hypertension targeting interleukin-21, Six Business Joint Results Report Meeting, Feb. 8, 2019.

* cited by examiner

*Primary Examiner* — Arthur S Leonard
*Assistant Examiner* — Erin V Paulus
(74) *Attorney, Agent, or Firm* — MARSHALL, GERSTEIN & BORUN LLP

(57) ABSTRACT

The present invention provides an aptamer that binds to IL-21, an aptamer that binds to IL-21 and inhibits the binding of IL-21 and a receptor thereof, and an aptamer that binds to IL-21 and contains a nucleotide sequence represented by the formula (1): CGRYKACY wherein R is A or G, Y is C or U, and K is G or U.

7 Claims, 21 Drawing Sheets

Specification includes a Sequence Listing.

[Fig. 1]

SEQ ID NO: 1 dG = -17.80 [Initially -17.80] 20Feb19-00-57-55

[Fig. 1] (continued)

SEQ ID NO: 2 dG = -18.20 [Initially -18.20] 20Feb19-00-59-13

[Fig. 2]
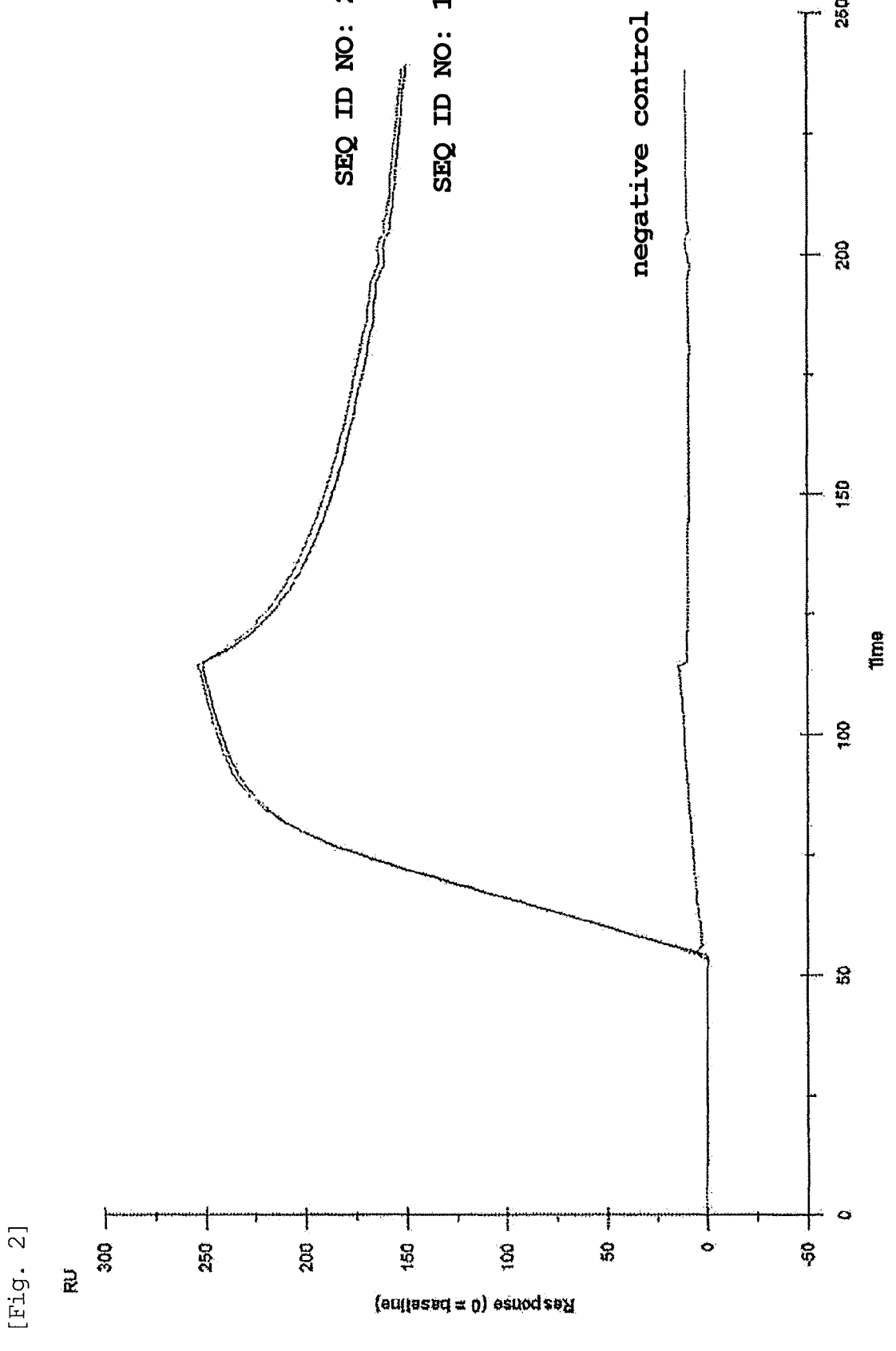

[Fig. 3]
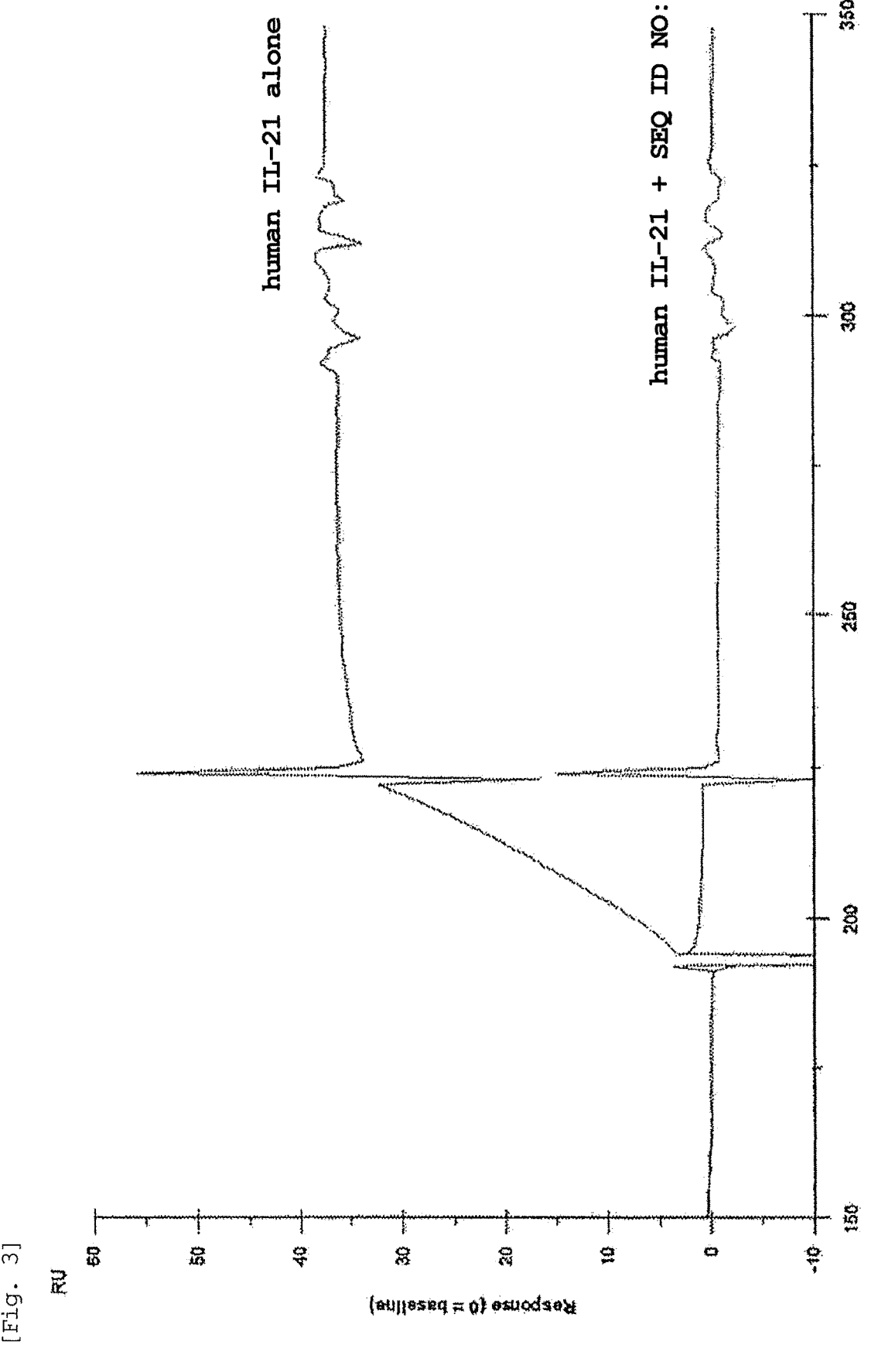

[Fig. 4]

SEQ ID NO: 3

Output of sir_graph(©)
mfold_util 4.7

Created Tue Jan 7 01:25:08 2020 dG = -15.10 [Initially -15.10] 20Jan07-01-25-07

[Fig. 4] (continued)

SEQ ID NO: 4

Output of sir_graph(©)
mfold_util 4.7

Created Wed Oct 25 06:11:23 2017 dG = -14.70 [Initially -14.70] 17Oct25-06-11-22

[Fig. 4] (continued)

SEQ ID NO: 5

Output of sir_graph(©)
mfold_util 4.7

Created Mon May 21 22:34:38 2018 dG = -9.30 [Initially -9.30] 18May21-22-34-37

[Fig. 4] (continued)

SEQ ID NO: 7

Output of slr_graph(©)
mfold_util 4.7

Created Tue Jan 7 02:03:19 2020

[Fig. 5]
SEQ ID NO: 22
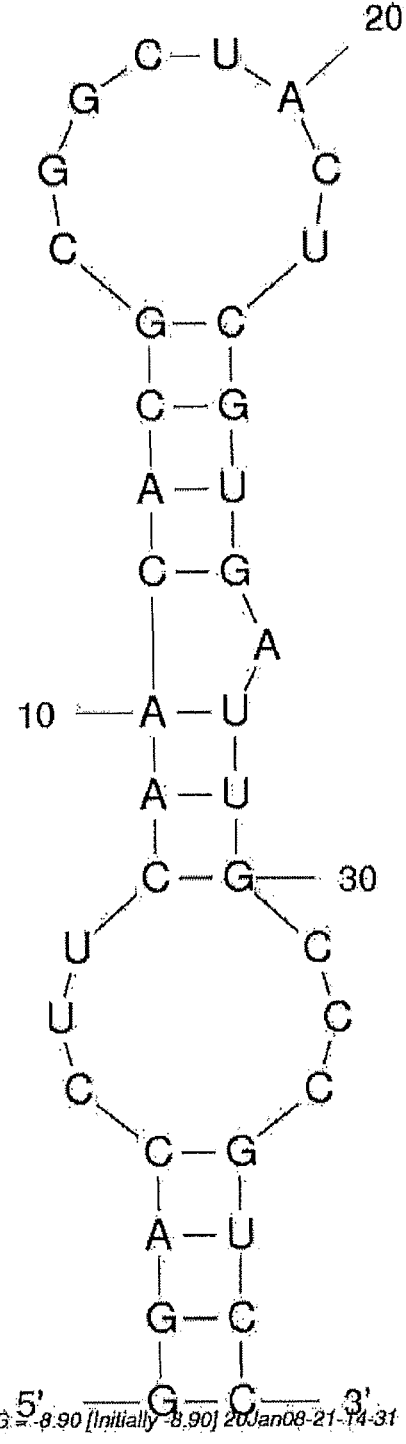

[Fig. 6]

SEQ ID NO: 25

[Fig. 6] (continued)
SEQ ID NO: 26
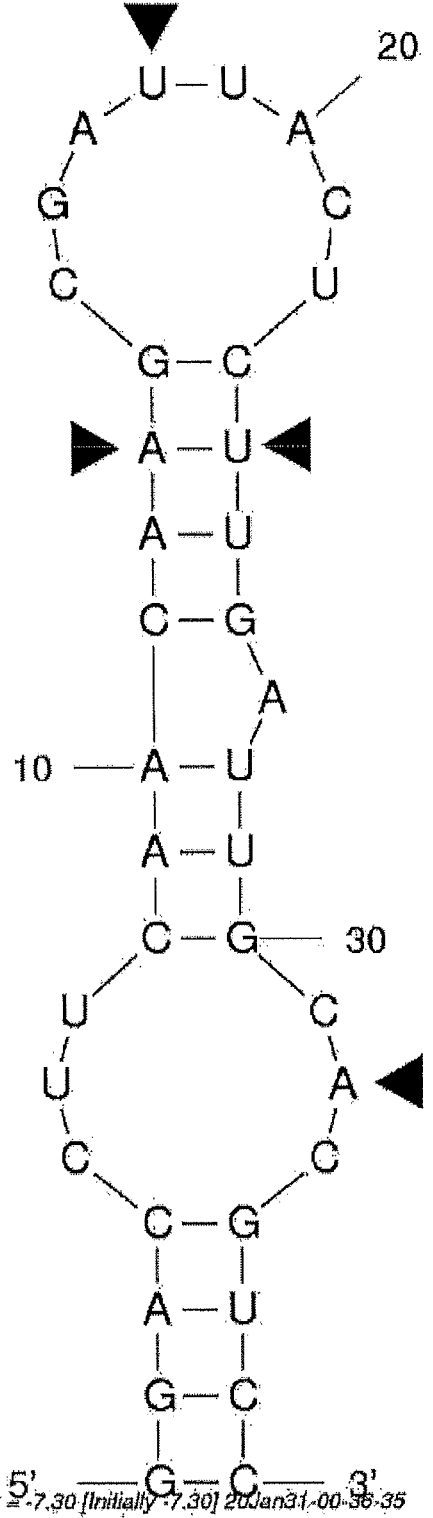

[Fig. 6] (continued)

SEQ ID NO: 27

[Fig. 6] (continued)

SEQ ID NO: 28 dG = -11.20 [Initially -11.20] 19Apr05-02-39-50

[Fig. 6] (continued)
SEQ ID NO: 29
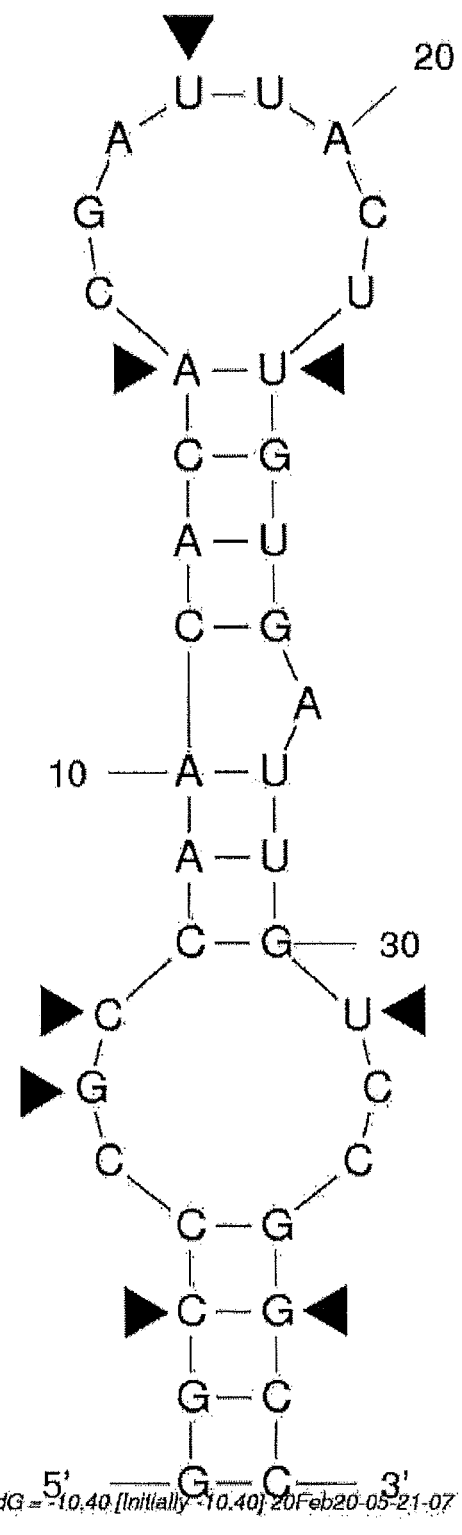

[Fig. 6] (continued)

SEQ ID NO: 30 dG = -11.90 [Initially -11.90] 20Feb20-05-21-42

[Fig. 6] (continued)

SEQ ID NO: 31 dG = -11.70 [Initially -11.70] 20Feb20-05-22-22

[Fig. 6] (continued)

SEQ ID NO: 32 dG 5'-8.30 [Initially -8.30] 20Feb20-05-22-50

[Fig. 6] (continued)
SEQ ID NO: 33
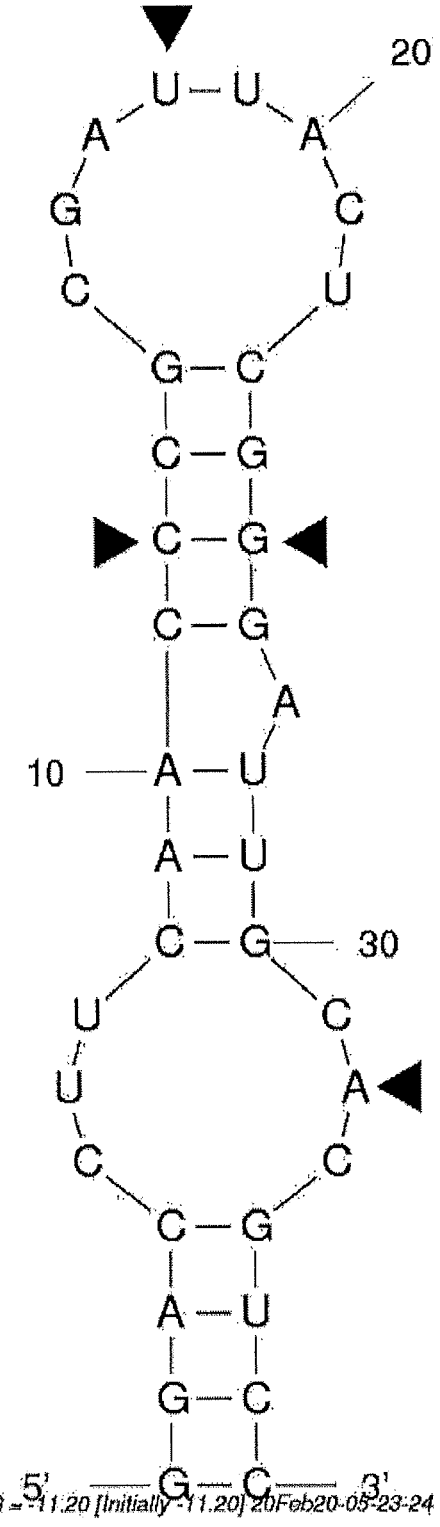

[Fig. 6] (continued)

SEQ ID NO: 34 dG = -8.30 [Initially -8.30] 19Apr05-02-40-40

[Fig. 6] (continued)

SEQ ID NO: 35 dG = -9.60 [Initially -9.60] 20Feb20-05-24-23

[Fig. 6] (continued)
SEQ ID NO: 36
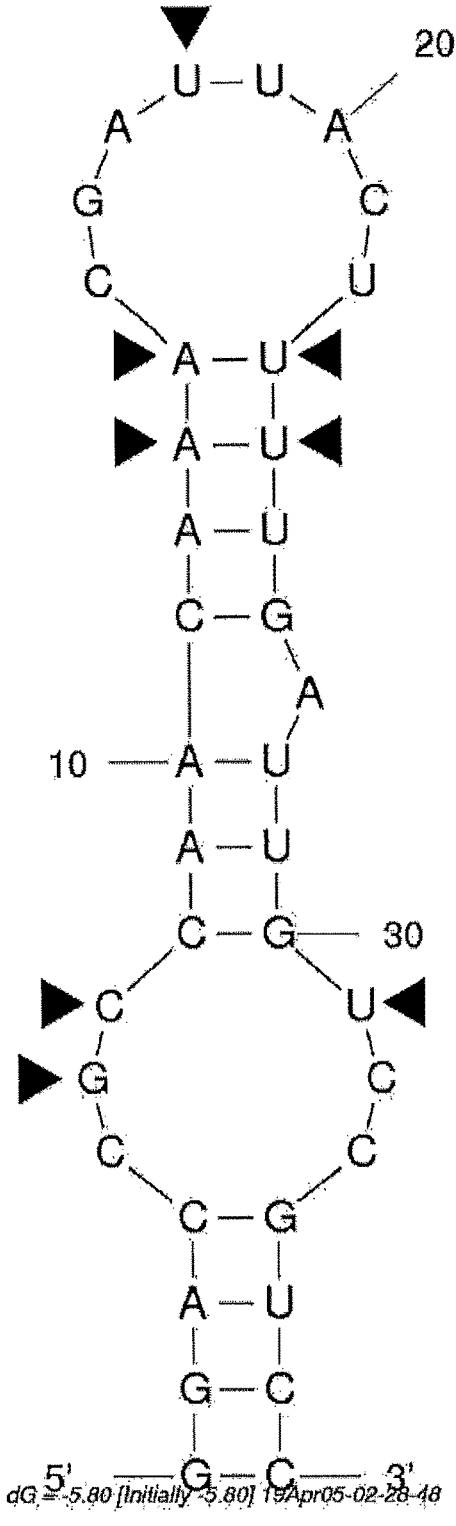

SEQUENCE LISTING

<160> NUMBER OF SEQ ID NOS: 53

<210> SEQ ID NO 1
<211> LENGTH: 65
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Aptamer binding to human IL-21 selected by
      SELEX

<400> SEQUENCE: 1
gggagaagaa ccuucaacac gcgacuacuc gugauugccc guucugagcc cagacgcucu      60
gcgcu                                                                 65

<210> SEQ ID NO 2
<211> LENGTH: 65
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature -continued

```
<223> OTHER INFORMATION: Aptamer binding to human IL-21 selected by
      SELEX

<400> SEQUENCE: 2
gggagaagaa ccuuccacga ccgacuacug ucaauggccc guucuuugcc cagacgcucu      60
gcgcu                                                                  65

<210> SEQ ID NO 3
<211> LENGTH: 51
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Variant from aptamer shown by SEQ ID NO:1

<400> SEQUENCE: 3
gggagaagaa ccuucaacac gcgacuacuc gugauugccc guucugagcc c               51

<210> SEQ ID NO 4
<211> LENGTH: 43
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Variant from aptamer shown by SEQ ID NO:1

<400> SEQUENCE: 4
ggagaaccuu caacacgcga cuacucguga uugcccguuc ucc                        43

<210> SEQ ID NO 5
<211> LENGTH: 37
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Variant from aptamer shown by SEQ ID NO:1

<400> SEQUENCE: 5
ggaccuucaa cacgcgacua cucgugauug cccgucc                               37

<210> SEQ ID NO 6
<211> LENGTH: 27
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Variant from aptamer shown by SEQ ID NO:1

<400> SEQUENCE: 6
ggcaacacgc gacuacucgu gauugcc                                          27

<210> SEQ ID NO 7
<211> LENGTH: 35
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Variant from aptamer shown by SEQ ID NO:5
```

-continued

<400> SEQUENCE: 7
ggccuucaac acgcgacuac ucgugauugc ccgcc                                    35

<210> SEQ ID NO 8
<211> LENGTH: 35
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Variant from aptamer shown by SEQ ID NO:7

<400> SEQUENCE: 8
ggacuucaac acgcgacuac ucgugauugc ccucc                                    35

<210> SEQ ID NO 9
<211> LENGTH: 36
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Variant from aptamer shown by SEQ ID NO:5

<400> SEQUENCE: 9
ggacuucaac acgcgacuac ucgugauugc ccgucc                                   36

<210> SEQ ID NO 10
<211> LENGTH: 36
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Variant from aptamer shown by SEQ ID NO:5

<400> SEQUENCE: 10
ggaccucaac acgcgacuac ucgugauugc ccgucc                                   36

<210> SEQ ID NO 11
<211> LENGTH: 36
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Variant from aptamer shown by SEQ ID NO:5

<400> SEQUENCE: 11
ggaccuucaa cacggacuac ucgugauugc ccgucc                                   36

<210> SEQ ID NO 12
<211> LENGTH: 36
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Variant from aptamer shown by SEQ ID NO:5

<400> SEQUENCE: 12
ggaccuucaa cacgcacuac ucgugauugc ccgucc                                   36

```
<210> SEQ ID NO 13
<211> LENGTH: 36
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Variant from aptamer shown by SEQ ID NO:5

<400> SEQUENCE: 13
ggaccuucaa cacgcgcuac ucgugauugc ccgucc                               36

<210> SEQ ID NO 14
<211> LENGTH: 36
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Variant from aptamer shown by SEQ ID NO:5

<400> SEQUENCE: 14
ggaccuucaa cacgcgauac ucgugauugc ccgucc                               36

<210> SEQ ID NO 15
<211> LENGTH: 36
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Variant from aptamer shown by SEQ ID NO:5

<400> SEQUENCE: 15
ggaccuucaa cacgcgacac ucgugauugc ccgucc                               36

<210> SEQ ID NO 16
<211> LENGTH: 36
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Variant from aptamer shown by SEQ ID NO:5

<400> SEQUENCE: 16
ggaccuucaa cacgcgacuc ucgugauugc ccgucc                               36

<210> SEQ ID NO 17
<211> LENGTH: 36
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Variant from aptamer shown by SEQ ID NO:5

<400> SEQUENCE: 17
ggaccuucaa cacgcgacua ucgugauugc ccgucc                               36

<210> SEQ ID NO 18
<211> LENGTH: 36
```

<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Variant from aptamer shown by SEQ ID NO:5

<400> SEQUENCE: 18
ggaccuucaa cacgcgacua ccgugauugc ccgucc                                36

<210> SEQ ID NO 19
<211> LENGTH: 36
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Variant from aptamer shown by SEQ ID NO:5

<400> SEQUENCE: 19
ggaccuucaa cacgcgacua cucgugauug ccgucc                                36

<210> SEQ ID NO 20
<211> LENGTH: 35
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Variant from aptamer shown by SEQ ID NO:5

<400> SEQUENCE: 20
gaccuucaac acgcgacuac ucgugauugc ccguc                                 35

<210> SEQ ID NO 21
<211> LENGTH: 33
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Variant from aptamer shown by SEQ ID NO:20

<400> SEQUENCE: 21
accuucaaca cgcgacuacu cgugauugcc cgu                                   33

<210> SEQ ID NO 22
<211> LENGTH: 37
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Variant from aptamer shown by SEQ ID NO:5

<400> SEQUENCE: 22
ggaccuucaa cacgcggcua cucgugauug cccgucc                               37

<210> SEQ ID NO 23
<211> LENGTH: 37
<212> TYPE: RNA
<213> ORGANISM: Artificial Sequence
<220> FEATURE:
<223> OTHER INFORMATION: synthetic polynucleotide -continued

```
<220> FEATURE:
<221> NAME/KEY: misc_feature
<223> OTHER INFORMATION: Variant from aptamer shown by SEQ ID NO:5

<400> SEQUENCE: 23
gaaccuucaa cacgcgacua cucgugauug cccguuc                                 37

<210> SEQ ID NO 24
<211> LENGTH: 35
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Variant from aptamer shown by SEQ ID NO:22

<400> SEQUENCE: 24
gaccuucaac acgcggcuac ucgugauugc ccguc                                   35

<210> SEQ ID NO 25
<211> LENGTH: 37
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Aptamer binding to human IL-21 selected by
      SELEX

<400> SEQUENCE: 25
ggaccuucaa cacgcgauua cucgugauug cccgucc                                 37

<210> SEQ ID NO 26
<211> LENGTH: 37
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Aptamer binding to human IL-21 selected by
      SELEX

<400> SEQUENCE: 26
ggaccuucaa caagcgauua cucuugauug cacgucc                                 37

<210> SEQ ID NO 27
<211> LENGTH: 37
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Aptamer binding to human IL-21 selected by
      SELEX

<400> SEQUENCE: 27
ggaccuucaa cccgcgauua cucgggauug cccgucc                                 37

<210> SEQ ID NO 28
<211> LENGTH: 37
<212> TYPE: RNA
<213> ORGANISM: Artificial Sequence
<220> FEATURE:
<223> OTHER INFORMATION: synthetic polynucleotide
```

-continued

```
<400> SEQUENCE: 28
ggaccuucaa cccgcgacua cucgggauug cccgucc                                      37

<210> SEQ ID NO 29
<211> LENGTH: 37
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Aptamer binding to human IL-21 selected by
      SELEX

<400> SEQUENCE: 29
ggcccgccaa cacacgauua cuugugauug uccggcc                                      37

<210> SEQ ID NO 30
<211> LENGTH: 37
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Aptamer binding to human IL-21 selected by
      SELEX

<400> SEQUENCE: 30
ggaccuucaa cacgcgauua cucgugauug accgucc                                      37

<210> SEQ ID NO 31
<211> LENGTH: 37
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Aptamer binding to human IL-21 selected by
      SELEX

<400> SEQUENCE: 31
ggaccuucaa cgcgcgacua cucgcgauug cccgucc                                      37

<210> SEQ ID NO 32
<211> LENGTH: 37
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Aptamer binding to human IL-21 selected by
      SELEX

<400> SEQUENCE: 32
ggaccgccaa cacacgauua cuugugauug cccgucc                                      37

<210> SEQ ID NO 33
<211> LENGTH: 37
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Aptamer binding to human IL-21 selected by
      SELEX
```

-continued

<400> SEQUENCE: 33
ggaccuucaa cccgcgauua cucgggauug cacgucc                         37

<210> SEQ ID NO 34
<211> LENGTH: 37
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Aptamer binding to human IL-21 selected by
      SELEX

<400> SEQUENCE: 34
ggaccgccaa cacacgacua cuugugauug uccgucc                         37

<210> SEQ ID NO 35
<211> LENGTH: 37
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Aptamer binding to human IL-21 selected by
      SELEX

<400> SEQUENCE: 35
ggaccuucau cacgcgauua cucgugaaug cccgucc                         37

<210> SEQ ID NO 36
<211> LENGTH: 37
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Aptamer binding to human IL-21 selected by
      SELEX

<400> SEQUENCE: 36
ggaccgccaa caaacgauua cuuuugauug uccgucc                         37

<210> SEQ ID NO 37
<211> LENGTH: 37
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Variant from aptamer shown by SEQ ID NO:28

<400> SEQUENCE: 37
ggaccuucaa cccgcggcua cucgggauug cccgucc                         37

<210> SEQ ID NO 38
<211> LENGTH: 35
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Variant from aptamer shown by SEQ ID NO:37

-continued

```
<400> SEQUENCE: 38
gaccuucaac ccgcggcuac ucgggauugc ccguc                                    35

<210> SEQ ID NO 39
<211> LENGTH: 37
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Variant from aptamer shown by SEQ ID NO:5

<400> SEQUENCE: 39
ggaccgucaa cacgcgacua cucgugauug cccgucc                                  37

<210> SEQ ID NO 40
<211> LENGTH: 37
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Variant from aptamer shown by SEQ ID NO:5

<400> SEQUENCE: 40
ggaccuccaa cacgcgacua cucgugauug cccgucc                                  37

<210> SEQ ID NO 41
<211> LENGTH: 37
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Variant from aptamer shown by SEQ ID NO:5

<400> SEQUENCE: 41
ggaccuucaa cacgcgacga cucgugauug cccgucc                                  37

<210> SEQ ID NO 42
<211> LENGTH: 37
<212> TYPE: RNA
<213> ORGANISM: Artificial Sequence
<220> FEATURE:
<223> OTHER INFORMATION: synthetic polynucleotide

<400> SEQUENCE: 42
ggaccuucaa cacgcgacua cccgugauug cccgucc                                  37

<210> SEQ ID NO 43
<211> LENGTH: 37
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Variant from aptamer shown by SEQ ID NO:5

<400> SEQUENCE: 43
ggaccuucaa cacgcgacua cucgugauug cacgucc                                  37

<210> SEQ ID NO 44
<211> LENGTH: 162
```

-continued

```
<212> TYPE: PRT
<213> ORGANISM: Homo sapiens

<400> SEQUENCE: 44

Met Arg Ser Ser Pro Gly Asn Met Glu Arg Ile Val Ile Cys Leu Met
1               5                   10                  15

Val Ile Phe Leu Gly Thr Leu Val His Lys Ser Ser Ser Gln Gly Gln
            20                  25                  30

Asp Arg His Met Ile Arg Met Arg Gln Leu Ile Asp Ile Val Asp Gln
        35                  40                  45

Leu Lys Asn Tyr Val Asn Asp Leu Val Pro Glu Phe Leu Pro Ala Pro
    50                  55                  60

Glu Asp Val Glu Thr Asn Cys Glu Trp Ser Ala Phe Ser Cys Phe Gln
65                  70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
            100                 105                 110

Gly Arg Arg Gln Lys His Arg Leu Thr Cys Pro Ser Cys Asp Ser Tyr
        115                 120                 125

Glu Lys Lys Pro Pro Lys Glu Phe Leu Glu Arg Phe Lys Ser Leu Leu
    130                 135                 140

Gln Lys Met Ile His Gln His Leu Ser Ser Arg Thr His Gly Ser Glu
145                 150                 155                 160

Asp Ser

<210> SEQ ID NO 45
<211> LENGTH: 538
<212> TYPE: PRT
<213> ORGANISM: Homo sapiens

<400> SEQUENCE: 45

Met Pro Arg Gly Trp Ala Ala Pro Leu Leu Leu Leu Leu Leu Gln Gly
1               5                   10                  15

Gly Trp Gly Cys Pro Asp Leu Val Cys Tyr Thr Asp Tyr Leu Gln Thr
            20                  25                  30

Val Ile Cys Ile Leu Glu Met Trp Asn Leu His Pro Ser Thr Leu Thr
        35                  40                  45

Leu Thr Trp Gln Asp Gln Tyr Glu Glu Leu Lys Asp Glu Ala Thr Ser
    50                  55                  60

Cys Ser Leu His Arg Ser Ala His Asn Ala Thr His Ala Thr Tyr Thr
65                  70                  75                  80

Cys His Met Asp Val Phe His Phe Met Ala Asp Asp Ile Phe Ser Val
                85                  90                  95

Asn Ile Thr Asp Gln Ser Gly Asn Tyr Ser Gln Glu Cys Gly Ser Phe
            100                 105                 110

Leu Leu Ala Glu Ser Ile Lys Pro Ala Pro Pro Phe Asn Val Thr Val
        115                 120                 125

Thr Phe Ser Gly Gln Tyr Asn Ile Ser Trp Arg Ser Asp Tyr Glu Asp
    130                 135                 140

Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Arg Lys Leu Ile
                165                 170                 175

Ser Val Asp Ser Arg Ser Val Ser Leu Leu Pro Leu Glu Phe Arg Lys
```

```
                180             185              190

Asp Ser Ser Tyr Glu Leu Gln Val Arg Ala Gly Pro Met Pro Gly Ser
        195             200              205

Ser Tyr Gln Gly Thr Trp Ser Glu Trp Ser Asp Pro Val Ile Phe Gln
        210             215              220

Thr Gln Ser Glu Glu Leu Lys Glu Gly Trp Asn Pro His Leu Leu Leu
225             230             235              240

Leu Leu Leu Leu Val Ile Val Phe Ile Pro Ala Phe Trp Ser Leu Lys
            245             250              255

Thr His Pro Leu Trp Arg Leu Trp Lys Lys Ile Trp Ala Val Pro Ser
        260             265              270

Pro Glu Arg Phe Phe Met Pro Leu Tyr Lys Gly Cys Ser Gly Asp Phe
        275             280              285

Lys Lys Trp Val Gly Ala Pro Phe Thr Gly Ser Ser Leu Glu Leu Gly
        290             295              300

Pro Trp Ser Pro Glu Val Pro Ser Thr Leu Glu Val Tyr Ser Cys His
305             310             315              320

Pro Pro Arg Ser Pro Ala Lys Arg Leu Gln Leu Thr Glu Leu Gln Glu
            325             330              335

Pro Ala Glu Leu Val Glu Ser Asp Gly Val Pro Lys Pro Ser Phe Trp
            340             345              350

Pro Thr Ala Gln Asn Ser Gly Gly Ser Ala Tyr Ser Glu Glu Arg Asp
        355             360              365

Arg Pro Tyr Gly Leu Val Ser Ile Asp Thr Val Thr Val Leu Asp Ala
        370             375              380

Glu Gly Pro Cys Thr Trp Pro Cys Ser Cys Glu Asp Asp Gly Tyr Pro
385             390             395              400

Ala Leu Asp Leu Asp Ala Gly Leu Glu Pro Ser Pro Gly Leu Glu Asp
            405             410              415

Pro Leu Leu Asp Ala Gly Thr Thr Val Leu Ser Cys Gly Cys Val Ser
            420             425              430

Ala Gly Ser Pro Gly Leu Gly Gly Pro Leu Gly Ser Leu Leu Asp Arg
        435             440              445

Leu Lys Pro Pro Leu Ala Asp Gly Glu Asp Trp Ala Gly Gly Leu Pro
        450             455              460

Trp Gly Gly Arg Ser Pro Gly Gly Val Ser Glu Ser Glu Ala Gly Ser
465             470             475              480

Pro Leu Ala Gly Leu Asp Met Asp Thr Phe Asp Ser Gly Phe Val Gly
            485             490              495

Ser Asp Cys Ser Ser Pro Val Glu Cys Asp Phe Thr Ser Pro Gly Asp
        500             505              510

Glu Gly Pro Pro Arg Ser Tyr Leu Arg Gln Trp Val Val Ile Pro Pro
        515             520              525

Pro Leu Ser Ser Pro Gly Pro Gln Ala Ser
    530             535
```

<210> SEQ ID NO 46
<211> LENGTH: 84
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: DNA template
<220> FEATURE:

```
<221> NAME/KEY: misc_feature
<222> LOCATION: (16)..(50)
<223> OTHER INFORMATION: n is a, c, g, or t

<400> SEQUENCE: 46
agcgcagagc gtctgnnnnn nnnnnnnnnn nnnnnnnnnn gaaggttctt        60
ctccctatag tgagtcgtat tagg                                   84

<210> SEQ ID NO 47
<211> LENGTH: 34
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Primer

<400> SEQUENCE: 47
cctaatacga ctcactatag ggagaagaac cttc                        34

<210> SEQ ID NO 48
<211> LENGTH: 15
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Primer

<400> SEQUENCE: 48
agcgcagagc gtctg                                             15

<210> SEQ ID NO 49
<211> LENGTH: 51
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Non-human IL-21 aptamer

<400> SEQUENCE: 49
gggaagcucc gucgagcuuu ccugcauaag cuguauugca gccagcauuu a      51

<210> SEQ ID NO 50
<211> LENGTH: 72
<212> TYPE: RNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Non-human IL-21 aptamer

<400> SEQUENCE: 50
gggaagcucc gucgagcuuu ccugcauaag cuguauugca gccagcauuu auuguacgcc  60
ugcguagcuc cu                                                72

<210> SEQ ID NO 51
<211> LENGTH: 68
<212> TYPE: DNA
<213> ORGANISM: Artificial Sequence
<220> FEATURE:
<223> OTHER INFORMATION: synthetic polynucleotide
```

-continued

```
<220> FEATURE:
<221> NAME/KEY: misc_feature
<223> OTHER INFORMATION: DNA template

<400> SEQUENCE: 51
gcagagctcg tgctcagaac gggcaatcac gagtagtcgc gtgttgaagg ttcttctcac        60
tgtgagcc                                                                 68

<210> SEQ ID NO 52
<211> LENGTH: 32
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Primer

<400> SEQUENCE: 52
taatacgact cactataggg ctcacagtga ga                                      32

<210> SEQ ID NO 53
<211> LENGTH: 15
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: Primer

<400> SEQUENCE: 53
gcagagctcg tgctc                                                         15
```

APTAMER FOR IL-21 AND USE THEREOF

CROSS REFERENCE TO RELATED APPLICATIONS

This application is a U.S. national stage of International Patent Application No. PCT/JP2021/023023, filed Jun. 17, 2021, which claims the benefit of Japanese Patent Application No. 2020-104831, filed Jun. 17, 2020, the entire contents of each of which are fully incorporated herein by reference.

INCORPORATION BY REFERENCE OF MATERIAL SUBMITTED ELECTRONICALLY

A Sequence Listing, which is a part of the present disclosure, is submitted concurrently with the specification as a text file. The name of the text file containing the Sequence Listing is "58645_Seqlisting.txt." The Sequence Listing was created on Dec. 15, 2022, and is 20,757 bytes in size. The subject matter of the Sequence Listing is incorporated by reference herein in its entirety.

TECHNICAL FIELD

The present invention is an invention relating to an aptamer against interleukin-21.

BACKGROUND ART

Pulmonary arterial hypertension (hereinafter sometimes abbreviated as "PAH") is a disease having hyperproliferation of the media and intima of pulmonary arteries as a background of the pathology. At present, pulmonary hypertension is treated with endothelin receptor antagonists (bosentan, ambrisentan, etc.), phosphodiesterase (PDE) 5 inhibitors (sildenafil, Tadalafil, etc.), prostaglandin 12 and derivatives thereof (epoprostenol, beraprost, etc.), and the like. However, the improvement of prognosis by treatments with these is not sufficient, and PAH is designated as one of the intractable diseases. Therefore, the development of a new treatment method for PAH is demanded.

It has been reported that inflammation is involved in the progression of PAH pathology, and particularly, the involvement of an inflammatory cytokine, interleukin-6 (IL-6), has been reported. In recent years, moreover, it has also been reported that interleukin-21 (hereinafter referred to as "IL-21") is secreted from Th17 cells, a kind of helper T cells, by the action of IL-6, and plays an important role in the onset of PAH (Non Patent Literature 1). Specifically, it is considered that IL-21 induces macrophages present in the lung to an M2 macrophage dominant state and promotes proliferation of lung artery smooth myocytes in correlation with the accumulation of M2 macrophages in lung tissue, which in turn causes the onset of PAH.

Patent Literature 1 describes that inhibition of signal transduction from IL-21 enables prophylaxis and treatment of pulmonary hypertension. Specifically, anti-IL-21 antibody inhibits the interaction between IL-21 and IL-21 receptor, thereby inhibiting signal transduction from IL-21. Patent Literature 1 describes IL-21 antibody, IL-21 receptor antibody, a peptide that binds to IL-21 and IL-21 receptor, and the like as substances capable of inhibiting the interaction between IL-21 and IL-21 receptor. However, it does not describe or suggest IL-21 aptamer.

Aptamers are nucleic acids that specifically bind to target molecules (proteins, sugar chains, hormones, etc.), and can bind to target molecules via a three-dimensional structure formed by single-stranded RNA (or DNA). A screening method called the SELEX method (Systematic Evolution of Ligands by Exponential Enrichment) is used to acquire an aptamer (Patent Literatures 2 to 4). The aptamers obtained by the SELEX method have a chain length of about 80 nucleotides, and are then shortened using the physiological inhibitory activity of the target molecule as an index. Furthermore, it is chemically modified for the purpose of improving in vivo stability, and optimized as a pharmaceutical product. Aptamers are unlikely to undergo immune elimination, and adverse reactions characteristic of antibodies, such as antibody-dependent cell-mediated cytotoxicity (ADCC) and complement-dependent cytotoxicity (CDC), do not occur easily with the use of aptamers. In addition, low-molecular-weight compounds, which are also molecular-targeted drugs, include poorly soluble molecules, and formulation thereof sometimes requires optimization. Aptamers are advantageous in this respect because they have high water solubility. Furthermore, since aptamers are produced by chemical synthesis, reduction of cost by large-scale production is possible. Other advantages of aptamers include long-term storage stability, heat resistance, and solvent resistance. On the other hand, the blood half-lives of aptamers are generally shorter than those of antibodies; however, this property is sometimes advantageous from the aspect of toxicity. Various aptamer drugs have been developed, including Macugen (target disease: age-related macular degeneration), which is the first RNA aptamer drug approved in December 2004 in the United States. In recent years, not only RNA aptamers but also DNA aptamers that can be stably and inexpensively produced in vivo have been developed. In recent years, not only RNA aptamers but also DNA aptamers that can be stable in vivo and produced at a low cost have also been developed.

In addition, many attempts have been made to use aptamers for purification of target molecules and molecular targeting by utilizing the high affinity that the aptamers have for target molecules. Aptamers often have higher affinity than antibodies having similar functions. Also from the aspect of delivery, since the molecular size of aptamers is about 1/10 that of antibodies, they easily migrate into tissues, making it easier to deliver drugs to the desired sites. Therefore, pharmaceutical products more useful than antibodies may be developed

CITATION LIST

Patent Literature

[PTL 1]
JP-B-6359921
[PTL 2]
WO 91/19813
[PTL 3]
WO 94/08050
[PTL 4]
WO 95/07364

Non Patent Literature

[NPL 1]
PNAS May 19, 2015 112 (20) E2677-E2686

SUMMARY OF INVENTION

Technical Problem

The present invention aims to provide an aptamer against IL-21.

Solution to Problem

The present inventors conducted intensive studies to solve the problem described above, and succeeded in producing an aptamer that binds to IL-21. They have also clarified that the aptamer inhibits the binding between IL-21 and IL-21 receptor. They have also clarified that the IL-21 aptamer is an aptamer having a characteristic motif sequence.

That is, the present invention provides the following.

[1] An aptamer that binds to interleukin-21.

[2] The aptamer of [1] that inhibits binding between interleukin-21 and a receptor thereof.

[3] The aptamer of [1] or [2], comprising a nucleotide sequence represented by the following formula (1):

$$\text{CGRYKACY} \tag{1}$$

wherein R is A or G, Y is C or U, and K is G or U.

[4] The aptamer of [3], wherein, at the 1st C in the formula (1), the hydroxy group at the 2'-position of ribose is substituted by a fluoro group.

[5] The aptamer of [3] or [4], further comprising a nucleotide sequence represented by the following formula (2):

$$\text{CCKYC} \tag{2}$$

wherein K is G or U and Y is C or U, and a nucleotide sequence represented by the following formula (3):

$$\text{GYMCG} \tag{3}$$

wherein Y is C or U and M is A or C.

[6] The aptamer of [5], wherein the respective nucleotide sequences are in the order of the formula (2), the formula (1), and the formula (3) from the 5'-terminal side.

[7] The aptamer of [5] or [6], wherein, in the formula (1), the 4th Y is C, and K and the 8th Y are each U, in the formula (2), K and Y are each U, and in the formula (3), Y and M are each C.

[8] The aptamer of any of [1] to [7], comprising a nucleotide sequence represented by the following formula (4):

$$\text{CCKYC-N}_1\text{-CGRYKACY-N}_2\text{-GYMCG} \tag{4}$$

wherein $N_1$ is any sequence with a length of 5 to 9 nucleotides, $N_2$ is any sequence with a length of 5 to 10 nucleotides, R is A or G, Y is C or U, K is G or U, and M is A or C.

[9] The aptamer of any of [1] to [7], comprising a nucleotide sequence represented by the following formula (5):

$$\text{X}_1\text{CCKYCX}_2\text{-N}_{1a}\text{-X}_3\text{CGRYKACYX}_4\text{-N}_{2a}\text{-X}_5\text{GYMCGX}_6 \tag{5}$$

wherein $N_{1a}$ is any sequence with a length of 3 to 7 nucleotides, $N_{2a}$ is any sequence with a length of 3 to 8 nucleotides, $X_1$ and $X_6$, $X_2$ and $X_5$, and $X_3$ and $X_4$ are nucleotides complementary to each other, R is A or G, Y is C or U, K is G or U, and M is A or C.

[10] An aptamer comprising a nucleotide sequence resulting from the substitution, deletion, insertion, or addition of 1 or several nucleotides in the aptamer of any of [1] to [9], wherein (a) in the nucleotide contained in the aptamer, (i) the 2'-position of ribose of each pyrimidine nucleotide is a fluorine atom, and (ii) the 2'-position of ribose of each purine nucleotide is a hydroxy group, or wherein (b) in the aptamer of (a), (i) the fluorine atoms at the 2'-position of ribose of respective pyrimidine nucleotides are each independently unsubstituted or substituted by an atom or group selected from the group consisting of a hydrogen atom, a hydroxy group, and a methoxy group, (ii) the hydroxy groups at the 2'-position of ribose of respective purine nucleotides are each independently unsubstituted or substituted by an atom or group selected from the group consisting of a hydrogen atom, a methoxy group, and a fluorine atom.

[11] The aptamer of any of [5] to [9], wherein, at the 4th C in the formula (3): GYMCG, the hydroxy group at the 2'-position of ribose is substituted by a fluoro group.

[12] The aptamer of any of [1] to [11], wherein the length of the nucleotide is not more than 65 nucleotides.

[13] The aptamer of [8] or [9], comprising the nucleotide sequence of the following (a) or (b):

(a) a nucleotide sequence represented by any of SEQ ID NOs: 1-5, 7, 20-29, and 31-43 (provided that uracil (U) may be thymine (T))

(b) a nucleotide sequence resulting from the substitution, deletion, insertion, or addition of 1 or several nucleotides in the nucleotide sequence of the above-mentioned (a).

[14] A complex comprising the aptamer of any of [1] to [13] and a functional substance.

[15] The complex of [14], wherein the functional substance is an affinity substance, a labeling substance, an enzyme, a drug delivery vehicle, or a drug.

[16] A medicament comprising the aptamer of any one of [1] to

[13] or the complex of [14] or [15].

[17] The medicament of [16], which is for the treatment or prophylaxis of pulmonary hypertension.

Advantageous Effects of Invention

The aptamer of the present invention or a complex containing the aptamer may be useful for the prophylaxis or treatment of diseases involving IL-21, particularly for the prophylaxis or treatment of pulmonary hypertension. Alternatively, it may also be useful for the purification and concentration of IL-21, labeling to IL-21, and detection and quantification of IL-21.

BRIEF DESCRIPTION OF DRAWINGS

Figure 1:
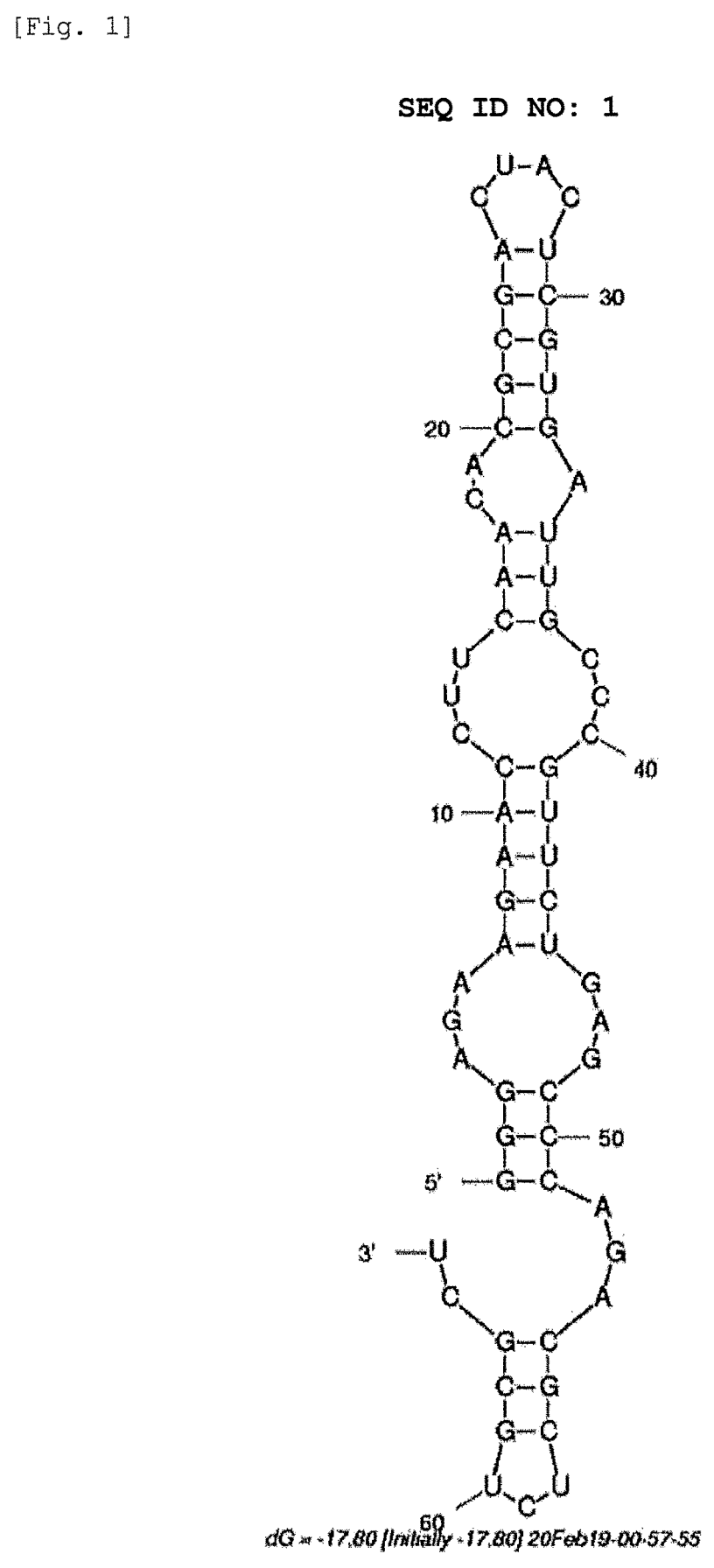
Figure 1:
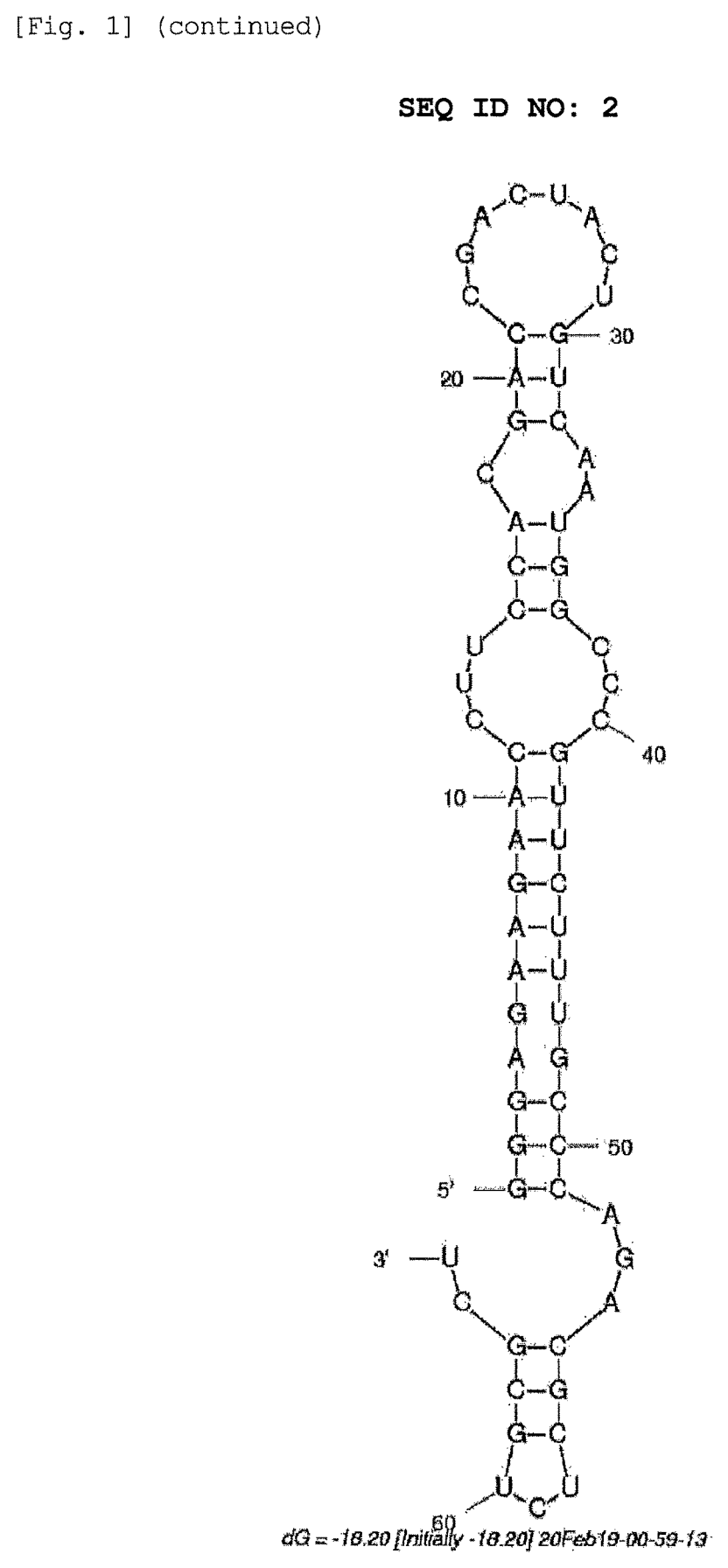

FIG. 1 shows secondary structure predictions of respective aptamers represented by SEQ ID NOs: 1 and 2.

FIG. 2 is a sensorgram showing that respective aptamers represented by SEQ ID NOs: 1 and 2 bind to human IL-21.

FIG. 3 is a sensorgram showing that the aptamer represented by SEQ ID NO: 1 inhibits the binding of human IL-21 and a receptor thereof.

FIG. 4 shows secondary structure predictions of respective aptamers represented by SEQ ID NOs: 3-5 and 7.

FIG. 5 shows secondary structure prediction of the aptamer represented by SEQ ID NO:22.

FIG. 6 shows secondary structure predictions of respective aptamers represented by SEQ ID NOs: 25-36.

DESCRIPTION OF EMBODIMENTS

The present invention provides an aptamer that binds to interleukin (IL) 21, that is, an aptamer having a binding activity to IL-21 (hereinafter sometimes to be referred to as "the aptamer of the present invention").

An aptamer refers to a nucleic acid molecule having a binding activity for a particular target molecule. The aptamer can inhibit the activity of a particular target molecule by binding to the particular target molecule. The aptamer of the present invention may be an RNA, a DNA, a modified nucleic acid or a mixture thereof. The aptamer of the present invention can also be in a linear, cyclic, or stemloop-like form, and may preferably take the below-mentioned stemloop-like structure.

The aptamer of the present invention binds to IL-21 in a physiological buffer. The buffer is not particularly limited, but one having a pH of about 5.0 to 10.0 is preferably used. Examples of the buffer include solution A described later (see Example 1). The aptamer of the present invention binds to IL-21 with an intensity detectable by any of the following tests.

Biacore T200 manufactured by GE Healthcare is used to measure the bonding strength. In one measurement method, an aptamer is first immobilized on a sensor chip. An IL-21 solution for an analyte was prepared to 0.1 μM and injected, and the binding of human IL-21 to the aptamer is detected. For example, an aptamer targeting other than human IL-21 (hereinafter "non-human IL-21 aptamer") is used as a negative control as used in the below-mentioned Example, and when human IL-21 binds to an aptamer significantly strongly as compared with the control nucleic acid, the aptamer can be determined to have the ability to bind to human IL-21. As another measurement method, it is also possible to immobilize human IL-21 on a sensor chip, inject an aptamer solution, and detect binding.

In one embodiment, the aptamer of the present invention binds to IL-21 and may inhibit the activity of IL-21. That is, the aptamer of the present invention may also have inhibitory activity against IL-21.

The inhibitory activity on IL-21 means an inhibitory capacity on any activity IL-21 has. For example, IL-21 acts on an IL-21 receptor expression cell to activate signal transduction and induce production of various cell growth factors and receptors thereof. Therefore, inhibitory activity on IL-21 can be an activity to inhibit intracellular signal transduction via an IL-21 receptor. Expression of various such cell growth factors and receptors thereof sometimes results in the promotion of cell growth activity and cell migration activity, or a decrease in the secretion of a specific humoral factor from various cells. Therefore, the inhibitory activity on IL-21 means inhibition of those activities and a decrease in a humoral factor conventionally secreted by stimulation of IL-21.

When the aptamer of the present invention binds to IL-21 and inhibits the binding of IL-21 to an IL-21 receptor, the action associated with the activation of the intracellular signal transduction pathway via the IL-21 receptor, for example, secretion of interferon γ in NK cells, may be inhibited. In other words, when the aptamer of the present invention reduces the secretion of interferon γ in NK cells, the aptamer of the present invention can be said to be an aptamer that binds to IL-21 and inhibits the binding of IL-21 to an IL-21 receptor.

IL-21 is a cytokine that is strongly expressed in CD4-positive T cells and natural killer T cells, and is, for example, a protein having the amino acid sequence represented by SEQ ID NO:44. In the present invention, IL-21 is produced in the body of an animal, or can also be produced from cultured cells such as mammalian cells of mouse and the like, insect cells, *Escherichia coli* and the like, or further can also be produced by chemical synthesis. When it is produced from cultured cells or by chemical synthesis, a variant can be easily produced by a method known per se. The "variant" of IL-21 means a protein or peptide having at least one activity from among the activities IL-21 inherently has, which has an amino acid sequence resulting from substitution, deletion, addition and the like of one to several amino acids of the known amino acid sequence of IL-21, or an amino acid sequence consisting of a part of the known amino acid sequence of IL-21. When an amino acid is substituted or added, said amino acid may be a natural amino acid or a non-natural amino acid. IL-21 in the present invention includes variants thereof.

The IL-21 receptor (hereinafter sometimes to be also referred to as "IL-21R") means a cell surface protein to which IL-21 binds. As the IL-21 receptor, a protein having the amino acid sequence shown in SEQ ID NO: 45 is known. The IL-21 receptor in the present invention may be a protein containing a natural amino acid sequence or a variant thereof. Here, the "variant" of the IL-21 receptor means a protein or peptide wherein one to several amino acids constituting the amino acid sequence of the known IL-21 receptor have been substituted, deleted, added, or the like, or having an amino acid sequence consisting of a part of the known amino acid sequence of IL-21 receptor, which has a binding activity to IL-21. In one embodiment, the present invention provides an aptamer that inhibits binding of IL-21 and an IL-21 receptor.

The aptamer of the present invention is not particularly limited as long as it binds to any portion of IL-21. In addition, the aptamer of the present invention is not particularly limited as long as it is capable of binding to any portion of IL-21 to inhibit the activity thereof.

The length of the aptamer of the present invention is not particularly limited, and can generally be not more than about 200 nucleotides, and can be, for example, not more than about 100 nucleotides, preferably not more than about 70 nucleotides, more preferably not more than about 65 nucleotides, further preferably not more than about 50 nucleotides, further more preferably not more than about 40 nucleotides, most preferably not more than about 37 nucleotides.

When the total number of nucleotides is smaller, chemical synthesis and mass-production will be easier, and there is a major advantage in terms of cost. It is also thought that chemical modification is easy, stability in vivo is high, and toxicity is low. The lower limit of the aptamer length in the present invention is not particularly limited as long as it contains a common sequence (CGRYKACY) and can adopt a stem-loop-like structure described later. The aptamer length may be, for example, 20 nucleotides or more, preferably 30 nucleotides or more, more preferably 35 nucleotides or more. In view of the above, in a particularly preferred embodiment of the present invention, the aptamer of the present invention has a length of 35 to 40 nucleotides.

In one preferred embodiment, the aptamer of the present invention is an aptamer that binds to IL-21 and contains a nucleotide sequence represented by the formula (1):

CGRYKACY (1)

wherein R is A or G, Y is C or U, and K is G or U.

Each nucleotide constituting the aptamer of the present invention may be each independently a ribose or a deoxyribose. When nucleotide is deoxyribose in the aptamer of the present invention, uracil (U) is hereinafter to be referred to as thymine (T).

In the formula (1), the 4th Y is preferably C, K is preferably U, and the 8th Y is preferably U.

In a more preferred embodiment, the aptamer of the present invention is an aptamer that binds to IL-21 and contains a nucleotide sequence represented by the following formula (2):

CCKYC (2)

wherein K is G or U and Y is C or U, and a nucleotide sequence represented by the following formula (3):

GYMCG (3)

wherein Y is C or U and M is A or C.

In the formula (2), K is preferably U and Y is preferably U. In the formula (3), Y is preferably C and M is preferably C.

The above-mentioned formula (1), the formula (2), and the formula (3) may be arranged in any order from the 5'-terminal side in the sequence of the aptamer of the present invention. The formula (2), the formula (1), and the formula (3) are preferably arranged in this order from the 5'-terminal side. When each sequence is configured in this order, the aptamer of the present invention can finely bind to IL-21.

In addition, each nucleotide sequence of the formula (1), the formula (2), and the formula (3) may be bonded via a nucleotide sequence to be a linker (spacer). The nucleotide sequence to be the linker is not particularly limited, and any sequence can be adopted as long as the aptamer of the present invention binds to IL-21.

The aptamer of the present invention is more preferably an aptamer containing a nucleotide sequence represented by the following formula (4):

CCKYC-N$_1$-CGRYKACY-N$_2$-GYMCG (4)

wherein N$_1$ is any sequence with a length of 5 to 9 nucleotides, N$_2$ is any sequence with a length of 5 to 10 nucleotides sequence, R is A or G, Y is C or U, K is G or U, and M is A or C.

As used herein, N$_1$ and N$_2$ correspond to the nucleotide sequences to be the above-mentioned linker, and it is found that the formula (2), the formula (1), and the formula (3) are arranged in this order from the 5'-terminal side via the linker.

When the formula (1), the formula (2), and the formula (3) are arranged in the configuration and the positional relationship shown in the formula (4), the aptamer of the present invention more strongly binds to IL-21, and thus can exhibit higher effects.

In the formula (4), the length of N$_1$ is generally 5 to 9 nucleotides, preferably 5 to 7 nucleotides, most preferably 6 nucleotides. The length of N$_2$ is generally 5 to 10 nucleotides, preferably 5 to 8 nucleotides, most preferably 6 or 7 nucleotides. When N$_1$ and N$_2$ have nucleotide lengths within these ranges, the function of the aptamer of the present invention is exhibited.

In addition, the difference in the lengths of N$_1$ and N$_2$ is preferably 0 to 2, more preferably 0 or 1. N$_1$ and N$_2$ located on both sides of the formula (1) part form a stem structure. The stem structure may contain a partial bulge structure or loop structure due to mismatch as long as the stem structure is formed as a whole.

Furthermore, the nucleotide sequences of N$_1$ and N$_2$ may be any nucleotide sequences as long as the formula (2) part (CCKYC) and the formula (3) part (GYMCG) form a base pair at each end and form an internal loop, and the formula (1) part (CGRYKACY) can form a loop.

Here, the formula (1) part may form a loop as a whole (CGRYKAC<u>Y</u>), or form a base pair (e.g., A-U) between, for example, the underlined R and Y and form a loop. Regardless of which loop is formed, the function of the aptamer of the present invention is exhibited as long as it possesses the aforementioned common sequence. In the latter case, the 2 nucleotides on the 5'-terminal side of N$_2$ desirably form a stem structure with "CG" on the 5'-terminal side of the formula (1), and the sequence thereof is not limited as long as it forms a stem structure. It is desirably "CG".

In the formula (4), preferred nucleotides in respective partial sequences corresponding to the aforementioned formulas (1) to (3) are as described above for the formulas (1) to (3).

The aptamer of the present invention is more preferably an aptamer containing a nucleotide sequence represented by the following formula (5):

X$_1$CCKYCX$_2$-N$_{1a}$-X$_3$CGRYKACYX$_4$-N$_{2a}$-X$_5$GYMCGX$_6$ (5)

wherein N$_{1a}$ is any sequence with a length of 3 to 7 nucleotides, N$_{2a}$ is any sequence with a length of 3 to 8 nucleotides, X$_1$ and X$_6$, X$_2$ and X$_5$, and X$_3$ and X$_4$ are nucleotides complementary to each other, R is A or G, Y is C or U, K is G or U, and M is A or C.

As used herein, N$_{1a}$ and N$_{2a}$ correspond to the nucleotide sequences to be the above-mentioned linker, and it is found that the formula (2), the formula (1), and the formula (3) are arranged in this order from the 5'-terminal side via the linker.

When the formula (1), the formula (2), and the formula (3) are arranged in the configuration and the positional relationship shown in the formula (5), the aptamer of the present invention further more strongly binds to IL-21, and thus can exhibit higher effects.

In the formula (5), the length of N$_{1a}$ is generally 3 to 7 nucleotides, preferably 3 to 5 nucleotides, most preferably 4 nucleotides. The length of N$_{2a}$ is generally 3 to 8 nucleotides, preferably 3 to 6 nucleotides, most preferably 4 or 5 nucleotides. When N$_{1a}$ and N$_{2a}$ have nucleotide lengths within these ranges, the function of the aptamer of the present invention is exhibited. In addition, the difference in the lengths of $N_{1a}$ and $N_{2a}$ is preferably 0 to 2, more preferably 0 or 1. $N_{1a}$ and $N_{2a}$ form a stem structure together with $X_2$, $X_3$ and $X_5$, $X_4$, respectively. The stem structure may contain a partial bulge structure or loop structure due to mismatch between $N_{1a}$ and $N_{2a}$ as long as the stem structure is formed as a whole.

Furthermore, $X_1$ and $X_6$, and $X_2$ and $X_5$ each form a base pair, thereby further stabilizing the formation of an internal loop between the formula (2) part (CCKYC) and the formula (3) part (GYMCG), and $X_3$ and $X_4$ form a base pair, whereby the formula (1) part (CGRYKACY) forms a loop.

In the formula (5), preferred nucleotides in respective partial sequences corresponding to the aforementioned formulas (1) to (3) are as described above for the formulas (1) to (3).

In one preferred embodiment, as the aptamer of the present invention, aptamers containing nucleotide sequences represented by SEQ ID NOs: 1-5, 7, 20-29, and 31-43 can be mentioned. The following shows nucleotide sequences represented by SEQ ID NOs: 1-5, 7, 20-29, and 31-43 (wherein uracil may be thymine). The underline shows the common sequence (the formula (2), the formula (1), and the formula (3) in this order from the 5'-terminal side).

SEQ ID NO: 1:
GGGAGAAGAA<u>CCUUC</u>AACACGCGACUACUCGUGAUUGCCCGUUCUGAGCC

CAGACGCUCUGCGCU

SEQ ID NO: 2:
GGGAGAAGA<u>ACCUUC</u>CACGACCGACUACUGUCAAUGGCCCGUUCUUUGCC

CAGACGCUCUGCGCU

SEQ ID NO: 3:
GGGAGAAGAA<u>CCUUC</u>AACACGCGACUACUCGUGAUUGCCCGUUCUGAGCC

C

SEQ ID NO: 4:
GGAGAA<u>CCUUC</u>AACACGCGACUACUCGUGAUUGCCCGUUCUCC

SEQ ID NO: 5:
GGA<u>CCUUC</u>AACACGCGACUACUCGUGAUUGCCCGUCC

SEQ ID NO: 7:
GG<u>CCUUC</u>AACACGCGACUACUCGUGAUUGCCCGCC

SEQ ID NO: 20:
GA<u>CCUUC</u>AACACGCGACUACUCGUGAUUGCCCGUC

SEQ ID NO: 21:
A<u>CCUUC</u>AACACGCGACUACUCGUGAUUGCCCGU

SEQ ID NO: 22:
GGA<u>CCUUC</u>AACACGCGGCUACUCGUGAUUGCCCGUCC

SEQ ID NO: 23:
GAA<u>CCUUC</u>AACACGCGACUACUCGUGAUUGCCCGUUC

SEQ ID NO: 24:
GA<u>CCUUC</u>AACACGCGGCUACUCGUGAUUGCCCGUC

SEQ ID NO: 25:
GGA<u>CCUUC</u>AACACGCGAUUACUCGUGAUUGCCCGUCC

SEQ ID NO: 26:
GGA<u>CCUUC</u>AACAAGCGAUUACUCUUGAUUGCACGUCC

SEQ ID NO: 27:
GGA<u>CCUUC</u>AACCCGCGAUUACUCGGGAUUGCCCGUCC

SEQ ID NO: 28:
GGA<u>CCUUC</u>AACCCGCGACUACUCGGGAUUGCCCGUCC

SEQ ID NO: 29:
GGCCCGCCAACACACGAUUACUUGUGAUUGUCCGGCC

SEQ ID NO: 31:
GGA<u>CCUUC</u>AACGCGCGACUACUCGCGAUUG<u>CCC</u>GUCC

SEQ ID NO: 32:
GGA<u>CCGCC</u>AACACACGAUUACUUGUGAUUG<u>CCC</u>GUCC

SEQ ID NO: 33:
GGA<u>CCUUC</u>AACCCGCGAUUACUCGGGAUUG<u>CAC</u>GUCC

SEQ ID NO: 34:
GGA<u>CCGCC</u>AACACACGACUACUUGUGAUUGUCCGUCC

SEQ ID NO: 35:
GGA<u>CCUUC</u>AUCACGCGAUUACUCGUGAAUG<u>CCC</u>GUCC

SEQ ID NO: 36:
GGA<u>CCGCC</u>AACAAACGAUUACUUUUGAUUGUCCGUCC

SEQ ID NO: 37:
GGA<u>CCUUC</u>AACCCGCGGCUACUCGGGAUUG<u>CCC</u>GUCC

SEQ ID NO: 38:
GA<u>CCUUC</u>AACCCGCGGCUACUCGGGAUUG<u>CCC</u>GUC

SEQ ID NO: 39:
GGA<u>CCGUC</u>AACACGCGACUACUCGUGAUUG<u>CCC</u>GUCC

SEQ ID NO: 40:
GGA<u>CCUCC</u>AACACGCGACUACUCGUGAUUG<u>CCC</u>GUCC

SEQ ID NO: 41:
GGA<u>CCUUC</u>AACACGCGACGACUCGUGAUUG<u>CCC</u>GUCC

SEQ ID NO: 42:
GGA<u>CCUUC</u>AACACGCGACUA<u>CCC</u>GUGAUUG<u>CCC</u>GUCC

SEQ ID NO: 43:
GGA<u>CCUUC</u>AACACGCGACUACUCGUGAUUG<u>CAC</u>GUCC

In one particularly preferred embodiment, the aptamer of the present invention contains the sequence represented by SEQ ID NO: 24 or 38.

In one embodiment, the aptamer of the present invention is an aptamer of any of the above-mentioned aptamers, which contains a nucleotide sequence wherein 1 or several nucleotides are substituted, deleted, inserted or added, and has binding activity to IL-21, preferably, further inhibitory activity on the binding of IL-21 and a receptor thereof.

Here, the number of nucleotides substituted, deleted, inserted or added as described above is not particularly limited as long as the aptamer still binds to IL-21 even after the substitution, deletion, insertion or addition. For example, it may be 1 to about 10, preferably 1 to 6, more preferably 1 to 5, further preferably 1 to 4, further preferably 1 to 3, most preferably 1 or 2. The site of the nucleotide to be substituted, deleted, inserted, or added is not particularly limited as long as the aptamer still binds to IL-21 even after the substitution, deletion, insertion or addition. In the above-mentioned formulas (1), (2) and (3), nucleotides can be substituted, deleted, inserted, or added at 1 to 3, preferably 1 or 2, more preferably 1, site (in the formulas (1), (2) and (3), at the site where plural kinds of nucleotides may be present (i.e., R, Y, K, or M), substitution between nucleotides included in the alternatives is not included). Particularly preferably, the formulas (1), (2) and (3) do not include substitution, deletion or insertion of nucleotides. On the other hand, at the sites other than those, more number of nucleotides (e.g., 1 to about 10, preferably 1 to 6, more preferably 1 to 5, further preferably 1 to 4) may be replaced, deleted, inserted, or added.

The aptamer of the present invention may be a conjugate of a plurality of any one kind of the above-mentioned aptamers, or a conjugate containing at least one of each of two or more kinds of aptamers selected from those mentioned above. These conjugates can also bind to IL-21.

Here, conjugation can be achieved by tandem binding. In the conjugation, a linker may be utilized. As the linker, nucleotide chains (e.g., 1 to about 20 nucleotides) and non-nucleotide chains (e.g., —(CH$_2$)$_n$— linker, —(CH$_2$CH$_2$O)$_n$— linker, hexaethylene glycol linker, TEG linker, peptide-containing linker, —S—S— bond-containing linker, —CONH— bond-containing linker, —OPO$_3$— bond-containing linker) can be mentioned. The plurality in the above-described plural conjugates is not particularly limited as long as it is two or more, and it may be, for example, 2, 3, or 4.

Each nucleotide contained in the aptamer of the present invention is the same or different and can be a nucleotide containing a hydroxyl group at the 2' position of ribose (e.g., ribose of pyrimidine nucleotide, ribose of purine nucleotide) (i.e., a natural nucleotide) or a nucleotide wherein a hydroxyl group is substituted (modified) by any atom or group at the 2' position of ribose (sometimes to be indicated as "modified nucleotide" in the present invention).

As examples of any such atom or group, a hydrogen atom, a fluorine atom or an —O-alkyl group (e.g., —O-Me group), an acyl group (e.g., —O—CHO group), an amino group (e.g., —NH$_2$ group), and the like can be mentioned. In the aptamer of the present invention, at least one kind (e.g., 1, 2, 3 or 4 kinds) of nucleotide can contain a hydroxyl group, or the above-described any atom or group, for example, at least two kinds (e.g., 2, 3 or 4 kinds) of atoms or groups selected from the group consisting of a hydrogen atom, a fluorine atom, and a —O-Me group, at the 2'-position of ribose.

In the aptamer of the present invention, all pyrimidine nucleotides may be nucleotides in which the 2'-position of ribose is a fluorine atom, or nucleotides in which said fluorine atoms are the same or different and each is unsubstituted or substituted by any atom or group mentioned above, preferably an atom or group selected from the group consisting of a hydrogen atom, a hydroxyl group and a methoxy group. Particularly, when a production method using a T7 Transcription Kit (manufactured by Ribomic Inc.) is applied as a production method of the aptamer of the present invention, an aptamer wherein the 2'-position of ribose of pyrimidine nucleotide is fluorinated can be obtained. The aptamer wherein a fluorine atom is substituted by other atom or group mentioned above can be produced by the below-mentioned method.

In the aptamer of the present invention, all purine nucleotides may be nucleotides in which the 2'-position of ribose is a hydroxy group, or nucleotides in which said hydroxy groups are the same or different and each is unsubstituted or substituted by any atom or group mentioned above, preferably an atom or group selected from the group consisting of a hydrogen atom, a methoxy group, and a fluorine atom. The aptamer wherein a hydroxyl group is substituted by other atom or group mentioned above can be produced by the below-mentioned method.

In the aptamer of the present invention, moreover, all pyrimidine nucleotides may be nucleotides wherein the fluorine atom at the 2'-position of ribose is substituted by any of the aforementioned atoms or groups, for example, the same atoms or groups selected from the group consisting of a hydrogen atom, a hydroxy group, and an —O-Me group.

In the aptamer of the present invention, moreover, all purine nucleotides may be nucleotides wherein the hydroxy group at the 2'-position of ribose is substituted by any of the aforementioned atoms or groups, for example, the same atoms or groups selected from the group consisting of a hydrogen atom, a fluorine atom and an —O-Me group.

In a preferred embodiment, each pyrimidine nucleotide contained in the aptamer of the present invention is a nucleotide having a fluorine atom at the 2'-position of ribose, and each purine nucleotide is a nucleotide having a hydroxy group at the 2'-position of ribose. In another embodiment, the above-mentioned fluorine atom at the 2'-position of the ribose of each pyrimidine nucleotide is independently optionally substituted by an atom or group selected from the group consisting of a hydrogen atom, a hydroxy group and a methoxy group, and the above-mentioned hydroxy group at the 2'-position of the ribose of each purine nucleotide is optionally independently substituted by an atom or group selected from the group consisting of a hydrogen atom, a methoxy group and a fluorine atom.

In this Description, the nucleotides constituting the aptamer are assumed to be RNAs (i.e., the sugar groups are assumed to be ribose) in describing how the sugar groups are modified in the nucleotides. However, this does not mean that DNA is exempted from the aptamer-constituting nucleotides, and a modification of RNA should read as a modification of DNA as appropriate. When the nucleotide constituting the aptamer is DNA, for example, replacement of the hydroxyl group at the 2'-position of ribose with X should read as a replacement of a hydrogen atom at the 2'-position of deoxyribose with X.

In the aptamer of the present invention, one or several, for example, 1 to 2, 1 to 3, 1 to 4, 1 to 5 nucleotides of phosphoric acid diester bond in the nucleotide may be modified or substituted by any substituent(s). For example, phosphoric acid diester bond may be substituted by a phosphorothioate bond, a phosphorodithioate bond, an alkylphosphonate bond, a phosphoramidate bond, and the like. Here, for example, "nucleotide is substituted by a phosphorothioate bond" means that a phosphoric acid group at a binding site between adjacent nucleotides is sulfurated, that is, a phosphodiester bond is altered to a phosphorothioate bond.

In the aptamer of the present invention, one or several, for example, 1 to 2, 1 to 3, 1 to 4, 1 to 5 nucleotides may be substituted by Bridged Nucleic Acid (BNA) or Locked Nucleic Acid (LNA) to stabilize the aptamer and improve the activity thereof. As used herein, the "bridged nucleic acid" refers to one having a structure wherein the binding affinity to a complementary sequence is enhanced by restricting the degree of freedom of nucleic acid by intramolecular crosslinking, and acquire nuclease resistance. Examples thereof include, but are not limited to, 2',4'-BNA (LNA), 2'-0,4'-C-ethylene-bridged Nucleic Acid (ENA), and the like.

The aptamer of the present invention may be one wherein a sugar residue (e.g., ribose) of each nucleotide has been modified to increase the IL-21 binding activity, stability, drug deliverability and the like. As examples of the modification in a sugar residue, replacement of oxygen atom at the 2'-position, 3'-position and/or 4'-position of the sugar residue with another atom, and the like can be mentioned. In addition, examples thereof include 4'-SRNA wherein the 4'-position oxygen is substituted with sulfur, LNA (Locked Nucleic Acid) wherein the 2'-position and the 4'-position are crosslinked via methylene, 3'-N-phosphoramidate nucleic acid wherein the 3'-position hydroxyl group is substituted with an amino group and the like. The aptamer of the present invention is sometimes produced with a given modification of the oxygen atom at the 2'-position of ribose of pyrimidine nucleotide, due to the production method thereof. When, for example, a production method using T7 Transcription Kit (manufactured by Ribomic Inc.) is applied as a production method of the aptamer of the present invention, an aptamer wherein the 2'-position of ribose of all pyrimidine nucleotides is fluorinated is preferably produced. Therefore, it is possible to produce various variations of aptamers having enhanced activity even though the base sequence is the same, by applying such alteration in the sugar residue to the obtained aptamer. From the above, the aptamer of the present invention can be preferably an aptamer wherein a sugar residue of at least one nucleotide is modified. Such alterations in the sugar residue can be performed by a method known per se (see, for example, Sproat et al., (1991), Nucl. Acid. Res. 19, 733-738; Cotton et al., (1991), Nucl. Acid. Res. 19, 2629-2635; Hobbs et al., (1973), Biochemistry 12, 5138-5145). To be specific, an aptamer wherein the hydroxyl group at the 2'-position of ribose is substituted by an atom or group selected from the group consisting of a hydrogen atom, a hydroxyl group and a methoxy group can be produced by using, as a base, an aptamer wherein the hydroxyl group at the 2'-position of ribose of all pyrimidine nucleotides is substituted by a fluoro group.

In one preferred embodiment of the aptamer of the present invention, at the 1st C in the formula (1), the hydroxy group at the 2'-position of ribose is substituted by a fluoro group. Alternatively/additionally, at the 2nd C in the formula (1), the hydroxy group at the 2'-position of ribose is substituted by a fluoro group. In one preferred embodiment of the aptamer of the present invention, the hydroxy group at the 2'-position of ribose at the 4th C in the formula (3): GYMCG is substituted by a fluoro group.

The aptamer of the present invention may also have a nucleic acid base (e.g., purine or pyrimidine) altered (e.g., chemically substituted) to increase the IL-21 binding activity, multimerization prevention, stability, drug deliverability, and the like. As examples of such alterations, pyrimidine alteration at 5-position, purine alteration at 6- and/or 8-position(s), alteration with an extracyclic amine, substitution with 4-thiouridine, and substitution with 5-bromo or 5-iodouracil can be mentioned. The phosphate group contained in the aptamer of the present invention may be altered to confer resistance to nuclease and hydrolysis. For example, the P(O)O group may be substituted by P(O)S (thioate), P(S)S (dithioate), P(O)N(R)R' (amidate), P(O)R, P(O)OR, CO or CH$_2$ (formacetal) or 3'-amine (—NH—CH$_2$—CH$_2$—) [wherein each R or R' is independently H or a substituted or unsubstituted alkyl (e.g., methyl, ethyl)].

The linking group is, for example, —O—, —N— or —S—, and nucleotides can bind to an adjoining nucleotide via these linking groups.

The alterations may also include alterations such as capping at 3' and 5'.

An alteration can further be performed by adding to an end a polyethylene glycol (PEG), amino acid, peptide, inverted dT, nucleic acid, nucleosides, Myristoyl, Lithocolic-oleyl, Docosanyl, Lauroyl, Stearoyl, Palmitoyl, Oleoyl, Linoleoyl, other lipids, steroids, cholesterol, caffeine, vitamins, dyes, fluorescent substances, anticancer agents, toxins, enzymes, radioactive substances, biotin, and the like. For such alterations, refer to, for example, U.S. Pat. Nos. 5,660,985 and 5,756,703.

Particularly, when alteration is performed by adding PEG to an end, the molecular weight of PEG is not particularly limited, and is preferably 1000 to 100000, more preferably 30000 to 90000. PEG may be linear or branched into two or more chains (multi-arm PEG). The terminus addition of PEG is useful for preventing the multimerization of the below-mentioned aptamer.

Such PEG is not particularly limited, and those of ordinary skill in the art can appropriately select and use commercially available or known PEG (e.g., http://www.peg-drug.com/peg_product/branched.html). Specific preferable examples of the PEG to be applied to the aptamer used in the present invention include 2-branched AS type (functional group: —CH$_2$—COO—NHS) PEG having a molecular weight of 40000 (Y-NHS-40K manufactured by Jenkem), 2-branched GS type (functional group: —CO—(CH$_2$)$_3$—COO—NHS) PEG having a molecular weight of 40000 (SUNBRIGHT GL2-400G5 manufactured by NOF CORPORATION), 2-branched TS type (active group: —COO—NHS) PEG having a molecular weight of 40000 (SUNBRIGHT GL2-400TS manufactured by NOF CORPORATION), 4-branched TS type PEG having a molecular weight of 40000 (SUNBRIGHT GL4-400TS manufactured by NOF CORPORATION), 2-branched TS type PEG having a molecular weight of 80000 (SUNBRIGHT GL2-800TS manufactured by NOF CORPORATION), 4-branched TS type PEG having a molecular weight of 80000 (SUNBRIGHT GL4-800TS manufactured by NOF CORPORATION) and the like.

In this case, in the aptamer of the present invention, PEG may be directly added to the terminus. It is more preferable that a linker having a group bindable to PEG and the like be added to the terminus thereof, and PEG be added to the aptamer of the present invention via the linker.

The linker between PEG and the aptamer used in the present invention is not particularly limited, and its carbon chain number, functional group, and the like can be appropriately selected according to the binding site, the type of PEG, and the like. Examples of such linker include a linker having an amino group. Specifically, when added to the 5' end, ssH Linker (SAFC) or DMS(O)MT-AMINO-MODIFIER (GLEN RESEARCH) can be mentioned, and when added to the 3' end, TFA Amino C-6 lcaa CPG (Chem-Genes), and the like can be mentioned. When this linker is selected, for example, an active group of N-hydroxysuccinimide is added to PEG, and reacted with an amino group on the linker side, whereby the aptamer used in the present invention can be bound to PEG via the linker.

As PEG and linker, commercially available products can be preferably used. The reaction conditions and the like relating to the binding of PEG, a linker and the aptamer used in the present invention can be appropriately determined by those of ordinary skill in the art.

The aptamer of the present invention can be chemically synthesized as disclosed herein and by a method known per se in the art. An aptamer binds to the target substance in a wide variety of binding modes, such as ionic bonds based on the negative charge of the phosphate group, hydrophobic bonds and hydrogen bonds based on ribose, and hydrogen bonds and stacking interaction based on nucleic acid bases. In particular, ionic bonds based on the negative charge of the phosphate group, which are present in the same number as the number of constituent nucleotides, are strong, and bind to lysine and arginine being present on the surface of the positive charge of protein. For this reason, nucleic acid bases not involved in the direct binding to the target substance can be substituted. In particular, because the region of stem structure has already formed base pairs and faces the inside of the double helical structure, nucleic acid bases are unlikely to bind directly to the target substance. Therefore, even when a base pair is substituted with another base pair, the activity of the aptamer often does not decrease. Even in structures wherein no base pairs are formed, such as loop structures, base substitution is possible when the nucleic acid base is not involved in the direct binding to the target molecule. Regarding modifications of the 2'-position of ribose, the functional group at the 2'-position of ribose infrequently interacts directly with the target molecule, but in many cases, it is of no relevance, and can be substituted by another modified molecule. Hence, an aptamer, unless the functional group involved in the direct binding to the target molecule is substituted or deleted, often retains the activity thereof. It is also important that the overall three-dimensional structure does not change substantially.

An aptamer can be prepared by utilizing the SELEX method or an improved version thereof (e.g., Ellington et al., (1990) Nature, 346, 818-822; Tuerk et al., (1990) Science, 249, 505-510). In the SELEX method, by increasing the number of rounds or using a competing substance, an aptamer exhibiting a stronger binding potential for the target substance is concentrated and selected. Hence, by adjusting the number of rounds of SELEX and/or changing the competitive condition, aptamers with different binding forces, aptamers with different binding modes, and aptamers with the same binding force or binding mode but different base sequences can be obtained in some cases. The SELEX method comprises a process of amplification by PCR; by causing a mutation by using manganese ions and the like in the process, it is possible to perform SELEX with higher diversity.

The aptamers obtained by SELEX are nucleic acids that exhibit high affinity for the target substance, but this does not necessarily mean that the aptamers bind to an active site of the target substance. Therefore, the aptamers obtained by SELEX do not necessarily act on the function of the target substance. An aptamer that does not bind to an active site may not influence the activity of the target substance. For example, BINKLEY et al. Nucleic Acids Res. 23(16):3198-3205 (1995) discloses several kinds of aptamers that bind to nerve growth factor (NGF) obtained by SELEX. Among them, three kinds of aptamers having high affinity for NGF were tested for inhibitory activity against the binding between NGF and NGF receptors. As a result, none of the aptamers inhibited the binding between NGF and NGF receptors (WO2010/0357259). This means that trial and error is required because, even if aptamers that bind to IL-21 are found by the SELEX method, a suitable combination of various conditions of SELEX must be found in order to obtain an aptamer having the activity of inhibiting the binding between IL-21 and IL-21 receptor to suppress signal transduction via the receptor. Whether or not the IL-21 aptamer obtained by SELEX inhibits the activities of IL-21 (e.g., IL-21 receptor-binding activity, IFN-γ secretion-inducing activity, etc.) can be verified, for example, using various assay methods described in the Examples below.

The active aptamer selected in this way can be further improved to show high performance by performing optimizing SELEX. In the optimizing SELEX, SELEX is performed again after preparing a template wherein an aptamer with a certain sequence is partially randomized, or a template doped with about 10 to 30% of random sequences.

An aptamer obtained by SELEX has a length of about 80 nucleotides, and this is difficult to prepare as a pharmaceutical as it is. Hence, it is preferable to repeat try-and-error efforts to shorten the aptamer to a length enabling easy chemical synthesis (e.g., chemical synthesis can be performed when it is not more than about 60 nucleotides, more preferably not more than about 50 nucleotides, further preferably not more than about 45 nucleotides).

Depending on the primer design for an aptamer obtained by SELEX, the ease of the subsequent minimization operation changes. Unless the primer is designed successfully, subsequent development will be impossible even if an aptamer with activity is selected by SELEX.

Aptamers are altered easily since they permit chemical synthesis. For aptamers, by predicting the secondary structure using the MFOLD program, or by predicting the steric structure by X-ray analysis or NMR analysis, it is possible to predict to some extent which nucleotide can be substituted or deleted, and where to insert a new nucleotide. A predicted aptamer with the new sequence can easily be chemically synthesized, and it can be determined whether or not the aptamer retains the activity using an existing assay system.

When a region important to the binding of the obtained aptamer with the target substance is identified by repeated try-and-error efforts as described above, the activity remains unchanged in many cases even when a new sequence is added to both ends of the sequence. The length of the new sequence is not particularly limited.

As mentioned earlier, modifications, like sequences, permit a wide range of design or alterations.

As stated above, aptamers permit a wide range of design or alterations. The present invention also provides a production method of aptamer that enables a wide range of design or alteration of an aptamer comprising a specified sequence (e.g., a sequence corresponding to a portion selected from among stem regions, internal loop regions, hairpin loop regions and single-strand regions: hereinafter, abbreviated as fixed sequence as required).

For example, the production method of such aptamer includes production of an aptamer comprising a fixed sequence by using a single kind of nucleic acid molecule consisting of a nucleotide sequence shown by:

Primer sequence (i)-(N)a-fixed sequence-(N)b-Primer sequence (ii)

[wherein (N)a represents a nucleotide chain consisting of "a" units of N; (N)b represents a nucleotide chain consisting of "b" units of N; each of the units of N, whether identical or different, is a nucleotide selected from the group consisting of A, G, C, U and T (preferably, A, G, C and U). Each of "a" and "b", whether identical or different, can be any numbers, and can be, for example, 1 to about 100, preferably 1 to about 50, more preferably 1 to about 30, still more preferably 1 to about 20 or 1 to about 10], or plural kinds of nucleic acid molecules (e.g., library of nucleic acid molecule different in the number of a, b etc.) and primer pairs corresponding to the primer sequences (i) and (ii), respectively.

The present invention also provides a complex comprising the aptamer of the present invention and a functional substance bound thereto. The bond between the aptamer and the functional substance in the complex of the present invention can be a covalent bond or a non-covalent bond. The complex of the present invention can be one wherein the aptamer of the present invention and one or more (e.g., 2 or 3) of functional substances of the same kind or different kinds are bound together. The functional substance is not particularly limited, as far as it newly confers a certain function to an aptamer of the present invention, or is capable of changing (e.g., improving) a certain characteristic which an aptamer of the present invention can possess. As examples of the functional substance, proteins, peptides, amino acids, lipids, sugars, monosaccharides, polynucleotides, and nucleotides can be mentioned. As examples of the functional substance, affinity substances (e.g., biotin, streptavidin, polynucleotides possessing affinity for target complementary sequence, antibodies, glutathione sepharose, histidine), substances for labeling (e.g., fluorescent substances, luminescent substances, radioisotopes), enzymes (e.g., horseradish peroxidase, alkaline phosphatase), drug delivery vehicles (e.g., liposome, microspheres, peptides, polyethyleneglycols), drugs (e.g., those used in missile therapy such as calicheamycin and duocarmycin; nitrogen mustard analogues such as cyclophosphamide, melphalan, ifosfamide or trofosfamide; ethylenimines such as thiotepa; nitrosoureas such as carmustine; alkylating agents such as temozolomide or dacarbazine; folate-like metabolic antagonists such as methotrexate or raltitrexed; purine analogues such as thioguanine, cladribine or fludarabine; pyrimidine analogues such as fluorouracil, tegafur or gemcitabine; vinca alkaloids such as vinblastine, vincristine or vinorelbine and analogues thereof; podophyllotoxin derivatives such as etoposide, taxans, docetaxel or paclitaxel; anthracyclines such as doxorubicin, epirubicin, idarubicin and mitoxantrone, and analogues thereof; other cytotoxic antibiotics such as bleomycin and mitomycin; platinum compounds such as cisplatin, carboplatin and oxaliplatin; pentostatin, miltefosine, estramustine, topotecan, irinotecan and bicalutamide), and toxins (e.g., ricin toxin, liatoxin and verotoxin) can be mentioned. These functional molecules are finally removed in some cases. Furthermore, the molecules may be peptides that can be recognized and cleaved by enzymes such as thrombin, matrix metalloproteinase (MMP), and Factor X, and may be polynucleotides that can be cleaved by nucleases or restriction endonuclease.

The aptamer or the complex of the present invention can be used as, for example, a pharmaceutical or a diagnostic reagent, a test reagent or a reagent. Particularly, it is useful as a therapeutic or prophylactic medicament, or a diagnostic reagent, a test reagent or a reagent for pulmonary hypertension.

The medicament of the present invention can be one formulated with a pharmaceutically acceptable carrier. As examples of the pharmaceutically acceptable carrier, excipients such as sucrose, starch, mannit, sorbit, lactose, glucose, cellulose, talc, calcium phosphate, and calcium carbonate; binders such as cellulose, methylcellulose, hydroxylpropylcellulose, polypropylpyrrolidone, gelatin, gum arabic, polyethylene glycol, sucrose, and starch; disintegrants such as starch, carboxymethylcellulose, hydroxylpropylstarch, sodium-glycol-starch, sodium hydrogen carbonate, calcium phosphate, and calcium citrate; lubricants such as magnesium stearate, AEROSIL, talc, and sodium lauryl sulfate; flavoring agents such as citric acid, menthol, glycyrrhizin-ammonium salt, glycine, and orange powder; preservatives such as sodium benzoate, sodium hydrogen sulfite, methylparaben, and propylparaben; stabilizers such as citric acid, sodium citrate, and acetic acid; suspending agents such as methylcellulose, polyvinylpyrrolidone, and aluminum stearate; dispersing agents such as surfactants; diluents such as water, physiological saline, and orange juice; base waxes such as cacao butter, polyethylene glycol, and kerosene; and the like can be mentioned, but these are not limitative.

Preparations suitable for oral administration are a solution prepared by dissolving an effective amount of ligand in a diluent such as water, physiological saline, or orange juice; capsules, sachets or tablets comprising an effective amount of ligand in solid or granular form; a suspension prepared by suspending an effective amount of active ingredient in an appropriate dispersant; an emulsion prepared by dispersing and emulsifying a solution of an effective amount of active ingredient in an appropriate dispersant, and the like.

The medicament of the present invention can be coated by a method known per se for the purpose of taste masking, enteric dissolution, sustained release and the like as necessary. As examples of coating agents used for the coating, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, EUDRAGIT (manufactured by Rohm, Germany, methacrylic acid/acrylic acid copolymer), pigments (e.g., ferric oxide red, titanium dioxide and the like) and the like are used. The medicament may be a rapid-release preparation or sustained-release preparation. Examples of the base of the sustained-release preparation include liposome, atelocollagen, gelatin, hydroxyapatite, PLGA and the like.

As preparations suitable for parenteral administration (e.g., intravenous administration, subcutaneous administration, intramuscular administration, topical administration, intraperitoneal administration, intranasal administration, pulmonary administration and the like), aqueous and non-aqueous isotonic sterile injectable liquids are available, which may comprise an antioxidant, a buffer solution, a bacteriostatic agent, an isotonizing agent and the like. Aqueous and non-aqueous sterile suspensions can also be mentioned, which may comprise a suspending agent, a solubilizer, a thickener, a stabilizer, an antiseptic and the like. The preparation can be included in a container such as an ampoule or a vial in a unit dosage volume or in several divided doses. An active ingredient and a pharmaceutically acceptable carrier can also be freeze-dried and stored in a state that may be dissolved or suspended in an appropriate sterile vehicle just before use. In addition to liquid injections, inhalants and ointments are also acceptable. In the case of an inhalant, an active ingredient in a freeze-dried state is micronized and administered by inhalation using an appropriate inhalation device. An inhalant can be formulated as appropriate with a conventionally used surfactant, oil, seasoning, cyclodextrin or derivative thereof and the like as required.

Here, as examples of the surfactant, oleic acid, lecithin, diethylene glycol dioleate, tetrahydroflufuryl oleate, ethyl oleate, isopropyl myristate, glyceryl trioleate, glyceryl monolaurate, glyceryl monooleate, glyceryl monostearate, glyceryl monolysinoate, cetyl alcohol, stearyl alcohol, polyethyleneglycol 400, cetylpyridinium chloride, sorbitan trioleate (trade name, Span 85), sorbitan monoleate (trade name, Span 80), sorbitan monolaurate (trade name, Span 20), polyoxyethylene hardened castor oil (trade name, HCO-60), polyoxyethylene (20) sorbitan monolaurate (trade name, Tween 20), polyoxyethylene (20) sorbitan monooleate (trade name, Tween 80), lecithin of natural resource origin (trade name, Epiclon), oleylpolyoxyethylene (2) ether (trade name, Brij 92), stearyl polyoxyethylene (2) ether (trade name, Brij 72), lauryl polyoxyethylene (4) ether (trade name, Brij 30), oleylpolyoxyethylene (2) ether (trade name, Genapol 0-020), block copolymer of oxyethylene and oxypropylene (trade name, Synperonic) and the like can be mentioned. Span, Tween, Epiclon, Brij, Genapol and Synperonic are trademarks.

As examples of the oil, corn oil, olive oil, cottonseed oil, sunflower oil and the like can be mentioned. In the case of an ointment, an appropriate pharmaceutically acceptable base (yellow petrolatum, white petrolatum, paraffin, plastibase, silicone, white ointment, beeswax, lard, vegetable oils, hydrophilic ointment, hydrophilic petrolatum, purified lanolin, hydrolyzed lanolin, water-absorbing ointment, hydrophilic plastibase, macrogol ointment and the like) is blended with an active ingredient, and used as a preparation.

An inhalant can be produced according to a conventional method. Specifically, an inhalant can be produced by powdering or liquefying the above-described aptamer and complex of the present invention, blending it in an inhalation propellant and/or carrier, and filling them in an appropriate inhalation vessel. When the above-described aptamer and complex of the present invention is a powder, an ordinary mechanical powder inhalator can be used; in the case of a liquid, an inhalator such as a nebulizer can be used. Here, as the propellant, conventionally known one can be widely used; chlorofluorocarbon-series compounds such as chlorofluorocarbon-11, chlorofluorocarbon-12, chlorofluorocarbon-21, chlorofluorocarbon-22, chlorofluorocarbon-113, chlorofluorocarbon-114, chlorofluorocarbon-123, chlorofluorocarbon-142c, chlorofluorocarbon-134a, chlorofluorocarbon-227, chlorofluorocarbon-C318, and 1,1,1,2-tetrafluoroethane, hydrocarbons such as propane, isobutane, and n-butane, ethers such as diethyl ether, compressed gases such as nitrogen gas and carbon dioxide gas and the like can be mentioned.

When the medicament of the present invention is used as a medicament for the prophylaxis or treatment of the above-mentioned diseases, the medicament of the present invention can be directly administered to a lesion, or administered according to the above-mentioned other methods.

Since the aptamer of the present invention is a single strand nucleic acid, detoxification by the administration of a nucleotide containing a complementary sequence is possible, and has a high possibility of making a pharmaceutical product with higher safety than a neutralizing antibody which is difficult to control dynamically after administration. This is an extremely advantageous aspect in view of the problem of infections possibly occurring in the antibody in the drug treatment and the like, which is caused by a long retention time of antibody in the body. Particularly, when the medicament of the present invention is used as a medicament for the prophylaxis or treatment of the above-mentioned diseases, it is obvious, in consideration of the severity of disease and the risk of side effects, that a medicament having higher safety can be obtained by utilizing an aptamer permitting easy control of in vivo kinetics.

The dosage of the medicament of the present invention varies depending on the kind and activity of active ingredient, seriousness of disease, animal species being the subject of administration, drug tolerability of the subject of administration, body weight, age and the like, and the usual dosage, based on the amount of active ingredient per day for an adult, can be about 0.0001 to about 100 mg/kg, for example, about 0.0001 to about 10 mg/kg, preferably about 0.005 to about 1 mg/kg.

The present invention is explained in detail in the following by referring to Examples, which are not to be construed as limitative.

EXAMPLE

Example 1: Preparation of RNA Aptamer that Binds Specifically to Human IL-21-(1)

RNA aptamers that bind specifically to human IL-21 were prepared using the SELEX method. The SELEX was performed by reference to the method of Ellington et al.

(Ellington and Szostak, Nature 346, 818-822, 1990) and the method of Tuerk et al. (Tuerk and Gold, Science 249, 505-510, 1990). Human IL-21 (manufactured by Peprotech Inc.) and mouse IL-21 (manufactured by Peprotech Inc.) were used as target substances. Human IL-21 and mouse IL-21 were each separately immobilized on a carrier of agarose resin (NHS-activated Sepharose 4 Fast Flow, manufactured by GE Healthcare). The method for immobilizing IL-21 on the carrier was performed according to the manual of GE Healthcare. The immobilization amount was confirmed by examining the IL-21 solution before immobilization and the supernatant immediately after immobilization by SDS-PAGE. As a result of SDS-PAGE, IL-21 band was not detected from the supernatant, which confirmed that almost all IL-21 used was immobilized.

The RNA (35N) used in the first round was obtained by double stranding a DNA template obtained by chemical synthesis by using Fwd primers and transcribing same using the T7 Transcription Kit (manufactured by Ribomic Inc.). The RNA obtained by this method has the 2'-position of the ribose of the pyrimidine nucleotide fluoro-substituted. The DNA of length 84 nucleotides shown below, having a primer sequence at each end of a 35-nucleotide random sequence was used as DNA template. The DNA template and the primers were prepared by chemical synthesis.

```
DNA template:
                                   (SEQ ID NO: 46)
5'-AGCGCAGAGCGTCTGNNNNNNNNNNNNNNNNNNNNNNNNNNNNNNNNNNN

NNNGAAGGTTCTTCTCCCTATAGTGAGTCGTATTAGG-3' primer Fwd:
                                   (SEQ ID NO: 47)
5'-CCTAATACGACTCACTATAGGGAGAAGAACCTTC-3' primer Rev:
                                   (SEQ ID NO: 48)
5'-AGCGCAGAGCGTCTG-3'
```

The continuous Ns in the DNA template (SEQ ID NO:46) are 35 nucleotides in any combination (35N: each N is A, C, G, or T), resulting in a unique sequence region in the obtained aptamer. Primer Fwd contains a promoter sequence of T7 RNA polymerase.

In the first round, a mixture of carriers on which human IL-21 and mouse IL-21 were immobilized was used, and thereafter, SELEX was performed by alternately using them by two rounds each. RNA pool was added to the carrier on which IL-21 was immobilized, and the mixture was maintained while slowly stirring for 20 min at 37° C. The resin was washed with solution A to remove RNA not bound to IL-21. Here, solution A is a mixed solution of 145 mM sodium chloride, 5.4 mM potassium chloride, 1.8 mM calcium chloride, 0.8 mM magnesium chloride, 20 mM tris (pH 7.6), 0.05% Tween 20. The RNA bound to IL-21 was recovered from the supernatant obtained by adding 6 M Urea as an eluate, followed by heat treatment at 85° C. for 2 min. The recovered RNA was amplified by RT-PCR, transcribed using T7 Transcription Kit and used as a pool for the next round. With the above as 1 round, a similar operation was repeatedly performed plural times. From the 5th round, the resin was washed with solution A' (solution obtained by changing 145 mM sodium chloride in solution A to 295 mM sodium chloride) in order to also remove RNA weakly bound to the resin. After completion of SELEX, base sequence analysis was performed using a next-generation sequencer. The Ion PGM™ system (manufactured by Thermo) was used as the next-generation sequencer, and the analysis was performed according to the Thermo Specification.

After 9 rounds of SELEX, 44,423 clone sequences were identified by a next-generation sequencer and confirmed to converge to 32,891 types of sequences. The sequences of a part of those clones are shown in SEQ ID NOs: 1 and 2. There were 182 sequences represented by SEQ ID NO:1. There were 69 sequences represented by SEQ ID NO:2. The common sequences present in SEQ ID NOs: 1 and 2 are underlined in each sequence. The 15 bases at each end have a common sequence because they are in the primer region.

Respective nucleotide sequences are shown below. Unless otherwise stated, the individual sequences listed below are shown in the direction of from 5' to 3', the purine bases (A and G) are in a 2'-OH form, and pyrimidine bases (U and C) are in a 2'-fluoro modified form. The secondary structure predictions of the aptamers represented by both SEQ ID NOs are shown in FIG. 1. The secondary structure was predicted using the MFOLD program (M. Zukker, Nucleic Acids Res. 31 (13), 3406-3415, 2003) (same for FIGS. 4 to 6).

```
SEQ ID NO: 1:
GGGAGAAGAACCUUCAACACGCGACUACUCGUGAUUGCCCGUUCUGAGCC

CAGACGCUCUGCGCU

SEQ ID NO: 2:
GGGAGAAGAACCUUCCACGACCGACUACUGUCAAUGGCCCGUUCUUUGCC

CAGACGCUCUGCGCU
```

The binding activities for human IL-21 of the aptamer shown by SEQ ID NOs:1 and 2 were evaluated by the surface plasmon resonance method. The measurements were taken using Biacore T200 manufactured by GE Healthcare. A CM4 chip with CM group-introduced dextran immobilized thereon was used as the sensor chip, which had streptavidin immobilized thereon. About 1000 RU of human IL-21 as a ligand was immobilized thereon. RNA as an analyte was adjusted to 0.1 μM using solution A and injected at a flow rate of 20 μL/min for 60 seconds. Solution A was also used as a running buffer.

As a result of the measurement, it was found that the aptamers represented by SEQ ID NOs: 1 and 2 bind to human IL-21. A sensorgram showing how these aptamers bind to human IL-21 is shown in FIG. 2. The nucleotide sequence used as the negative control (non-human IL-21 aptamer, 51 mer (GGGAAGCUCCGUCGAGCUUUC-CUGCAUAAGCUGUAUUGCAGCCAGCAUUUA; SEQ ID NO: 49)) did not show the binding to human IL-21. From the above, it was shown that the aptamers represented by SEQ ID NOs: 1 and 2 bind to human IL-21 in a sequence-specific manner.

Whether or not the aptamer represented by SEQ ID NO: 1 inhibits the binding of human IL-21 to its receptor IL-21R was evaluated by the surface plasmon resonance method. Biacore T200 manufactured by GE Healthcare was used for the measurement. A CM5 chip on which CM group-introduced dextran was immobilized was used as the sensor chip, and about 1500 RU of protein A (manufactured by Pierce) was immobilized thereon. Human IL-21R/Fc chimera protein (manufactured by R&D systems) to be a ligand was adjusted to 0.1 μM with solution A and injected at a flow rate of 10 μL/min for 60 seconds to immobilize about 700 RU. human IL-21 adjusted to 0.02 μM was injected thereto at a flow rate of 10 μL/min for 30 seconds to find the binding of about 35 RU. To evaluate whether this binding is inhibited by an aptamer, a mixed solution of human IL-21 and an aptamer was injected under the same conditions. The mixed solution was adjusted with solution A such that the concentration of human IL-21 in the solution was 0.02 μM and the concentration of the aptamer was 0.2 μM. Solution A was also used as a running buffer.

A sensorgram obtained by the measurement is shown in FIG. 3. A mixed solution of human IL-21 and SEQ ID NO: 1 did not show the binding to the receptor IL-21R, indicating that the aptamer represented by SEQ ID NO: 1 inhibits the binding of human IL-21 and IL-21R.

Whether the aptamers represented by SEQ ID NOs: 1 and 2 inhibit the function of human IL-21 even under conditions that mimic the environment in blood, such as a cell evaluation system, was evaluated using the following cell evaluation system. Human NK (natural killer)-like cell line NK92 cells (purchased from American Type Culture Collection) secrete interferon-γ (IFN-γ), which is a type of cytokine, upon stimulation with human IL-21. After culturing the NK92 cells for several days according to the attached specifications, the cells were passaged using the standard medium without IL-2 (manufactured by Roche). This is to suppress IFN-γ secretion by IL-2.

After overnight culture, the same medium was used to seed $2 \times 10^4$ cells per well for testing. Human IL-21 alone or a mixed solution of human IL-21 and aptamer was added thereto and the cells were cultured for 16 hr. The final concentration of human IL-21 was adjusted to 0.05 nM. After 16 hr, the culture supernatant was collected and IFN-γ contained in the supernatant was quantified by sandwich ELISA method. An ELISA Kit manufactured by R&D Systems or Diaclone was used for quantification. After quantification, the inhibitory rate was calculated using the following formula.

$$\text{inhibitory rate } (\%) = (C_{IL\text{-}21} - C_{apt})/(C_{IL\text{-}21} - C_0) \times 100$$

As used herein, $C_{IL\text{-}21}$ is the IFN-γ concentration per unit volume when only human IL-21 was added, $C_{apt}$ is the IFN-γ concentration when human IL-21 and aptamer were simultaneously added, and $C_0$ is the IFN-γ concentration at the time of no addition of human IL-21.

As a result of the test, the both aptamers represented by SEQ ID NOs: 1 and 2 were found to inhibit IFN-γ secretion from NK92 cells by the stimulation with human IL-21. A 72 base nucleotide sequence used as a negative control (non-human IL-21 aptamer, 72 mer GGGAAGCUCCGU-CGAGCUUUCCUGCAUAAGCUGUAUUGCAGCCAG-CAUUUAUUGUACGCCUGC GUAGCUCCU; (SEQ ID NO: 50)) did not show inhibitory activity (inhibitory rate −7.5%).

The above evaluation results of the aptamers represented by SEQ ID NOs: 1 and 2 are summarized in Table 1. In Table 1, "++" for binding indicates that the binding amount (RU value) of the aptamer to human IL-21 immobilized on the CM4 chip is 100 or more. In addition, "n.d." indicates unmeasured.

TABLE 1

| SEQ ID NO | length | human IL-21 binding activity in Biacore | human IL-21 and IL-21R binding inhibitory activity | inhibitory rate (%) in cell assay system (10 nM aptamer) |
|---|---|---|---|---|
| 1 | 65 | ++ | ++ | 80.8 |
| 2 | 65 | ++ | n.d. | 82.4 |

The aptamers represented by SEQ ID NOs: 1 and 2 bind to human IL-21 and inhibit an action with receptor IL-21R thereof. The effect was exhibited even under conditions mimicking the environment in blood, such as in a cell assay system, and it was shown that they are superior aptamers that inhibit human IL-21.

Example 2: Shortening of Aptamer—(1)

The aptamer represented by SEQ ID NO: 1 was shortened based on the secondary structure prediction obtained in FIG. 1. The nucleotide sequences of aptamers produced by shortening are shown below as SEQ ID NOs: 3 to 19. The underline in each sequence indicates a common sequence (corresponding to formula (2), formula (1) and formula (3) in this order from the 5'-terminal side (the underline in SEQ ID NO: 6 corresponds to formula (1))).

Unless otherwise stated, the individual sequences listed below are shown in the direction of from 5' to 3', the purine bases (A and G) are in a 2'-OH form, and pyrimidine bases (U and C) are in a 2'-fluoro modified form.

SEQ ID NO: 3 (sequence obtained by shortening the sequence represented by SEQ ID NO: 1 to a length of 51 nucleotides):

GGGAGAAGAACCUUCAACACGCGACUACUCGUGAUUGCCCGUUCUGAGCC

C

SEQ ID NO: 4 (sequence obtained by shortening the sequence represented by SEQ ID NO: 1 to a length of 43 nucleotides):

GGAGAACCUUCAACACGCGACUACUCGUGAUUGCCCGUUCUCC

SEQ ID NO: 5 (sequence obtained by shortening the sequence represented by SEQ ID NO: 1 to a length of 37 nucleotides):

GGACCUUCAACACGCGACUACUCGUGAUUGCCCGUCC

SEQ ID NO: 6 (sequence obtained by shortening the sequence represented by SEQ ID NO: 1 to a length of 27 nucleotides):

GGCAACACGCGACUACUCGUGAUUGCC

SEQ ID NO: 7 (sequence shortened to a length of 35 nucleotides by deleting the AU base pair consisting of the 3rd and 35th bases of the sequence represented by SEQ ID NO: 5):

GGCCUUCAACACGCGACUACUCGUGAUUGCCCGCC

SEQ ID NO: 8 (35-nucleotide sequence obtained by substituting CG base pairs (bases in the common sequence) consisting of the 3rd and 33rd bases of the sequence represented by SEQ ID NO: 7 with AU base pairs)

GGACUUCAACACGCGACUACUCGUGAUUGCCCUCC

SEQ ID NO: 9 (sequence shortened to a length of 36 nucleotides by deleting the 5th C (base in the common sequence) of the sequence represented by SEQ ID NO: 5):

GGACUUCAACACGCGACUACUCGUGAUUGCCCGUCC

SEQ ID NO: 10 (sequence shortened to a length of 36 nucleotides by deleting the 6th U (base in the common sequence) of the sequence represented by SEQ ID NO: 5):

GGACCUCAACACGCGACUACUCGUGAUUGCCCGUCC

SEQ ID NO: 11 (sequence shortened to a length of 36 nucleotides by deleting the 15th C (base in the common sequence) of the sequence represented by SEQ ID NO: 5):

GGACCUUCAACACGGACUACUCGUGAUUGCCCGUCC

SEQ ID NO: 12 (sequence shortened to a length of 36 nucleotides by deleting the 16th G (base in the common sequence) of the sequence represented by SEQ ID NO: 5):

GGACCUUCAACACGCACUACUCGUGAUUGCCCGUCC

SEQ ID NO: 13 (sequence shortened to a length of 36 nucleotides by deleting the 17th A (base in the common sequence) of the sequence represented by SEQ ID NO: 5):

GGACCUUCAACACGCGCUACUCGUGAUUGCCCGUCC

SEQ ID NO: 14 (sequence shortened to a length of 36 nucleotides by deleting the 18th C (base in the common sequence) of the sequence represented by SEQ ID NO: 5):

GGACCUUCAACACGCGAUACUCGUGAUUGCCCGUCC

SEQ ID NO: 15 (sequence shortened to a length of 36 nucleotides by deleting the 19th U (base in the common sequence) of the sequence represented by SEQ ID NO: 5):

GGACCUUCAACACGCGACACUCGUGAUUGCCCGUCC

SEQ ID NO: 16 (sequence shortened to a length of 36 nucleotides by deleting the 20th A (base in the common sequence) of the sequence represented by SEQ ID NO: 5):

GGACCUUCAACACGCGACUCUCGUGAUUGCCCGUCC

SEQ ID NO: 17 (sequence shortened to a length of 36 nucleotides by deleting the 21st C (base in the common sequence) of the sequence represented by SEQ ID NO: 5):

GGACCUUCAACACGCGACUAUCGUGAUUGCCCGUCC

SEQ ID NO: 18 (sequence shortened to a length of 36 nucleotides by deleting the 22nd U (base in the common sequence) of the sequence represented by SEQ ID NO: 5):

GGACCUUCAACACGCGACUACCGUGAUUGCCCGUCC

SEQ ID NO: 19 (sequence shortened to a length of 36 nucleotides by deleting the 31st C (base in the common sequence) of the sequence represented by SEQ ID NO: 5):

GGA<u>CCUUCAACACG</u>CGACUACUCGUGAUU<u>GCCGUCC</u>

Whether these aptamers bind to human IL-21 and inhibit the function thereof was evaluated by a method similar to that in Example 1. Aptamers were obtained by transcription using double-stranded DNA as a template. The results thereof are shown in Table 2. In the Table, "++" in the binding activity in Biacore indicates that the binding amount (RU value) is 100 or more, "+" indicates that the binding amount (RU value) is 20 or more and less than 100, and "-" indicates that the binding amount is less than 20. The "+" of the inhibitory activity indicates that the aptamer at a concentration of 10 nM inhibited 20% or more in the inhibitory rate (%) in the cell assay system, and "-" indicates a failure to meet the criteria. In addition, "n.d." indicates unmeasured.

TABLE 2

| SEQ ID NO: | length | binding activity in Biacore | inhibitory rate (%) in cell assay system (10 nM aptamer) | inhibitory activity |
|---|---|---|---|---|
| 3 | 51 | ++ | 83.5 | + |
| 4 | 43 | ++ | 75.8 | + |
| 5 | 37 | ++ | 65.1 | + |
| 6 | 27 | – | 15.5 | – |
| 7 | 35 | ++ | 58.3 | + |
| 8 | 35 | n.d. | 8.3 | – |
| 9 | 36 | n.d. | –6.4 | – |
| 10 | 36 | n.d. | –4.2 | – |
| 11 | 36 | n.d. | –1.0 | – |
| 12 | 36 | n.d. | –7.6 | – |
| 13 | 36 | n.d. | –14.0 | – |
| 14 | 36 | + | 13.3 | – |
| 15 | 36 | + | 10.7 | – |
| 16 | 36 | + | 10.7 | – |
| 17 | 36 | – | 7.4 | – |
| 18 | 36 | n.d. | –6.5 | – |
| 19 | 36 | n.d. | –9.8 | – |

Figure 4:
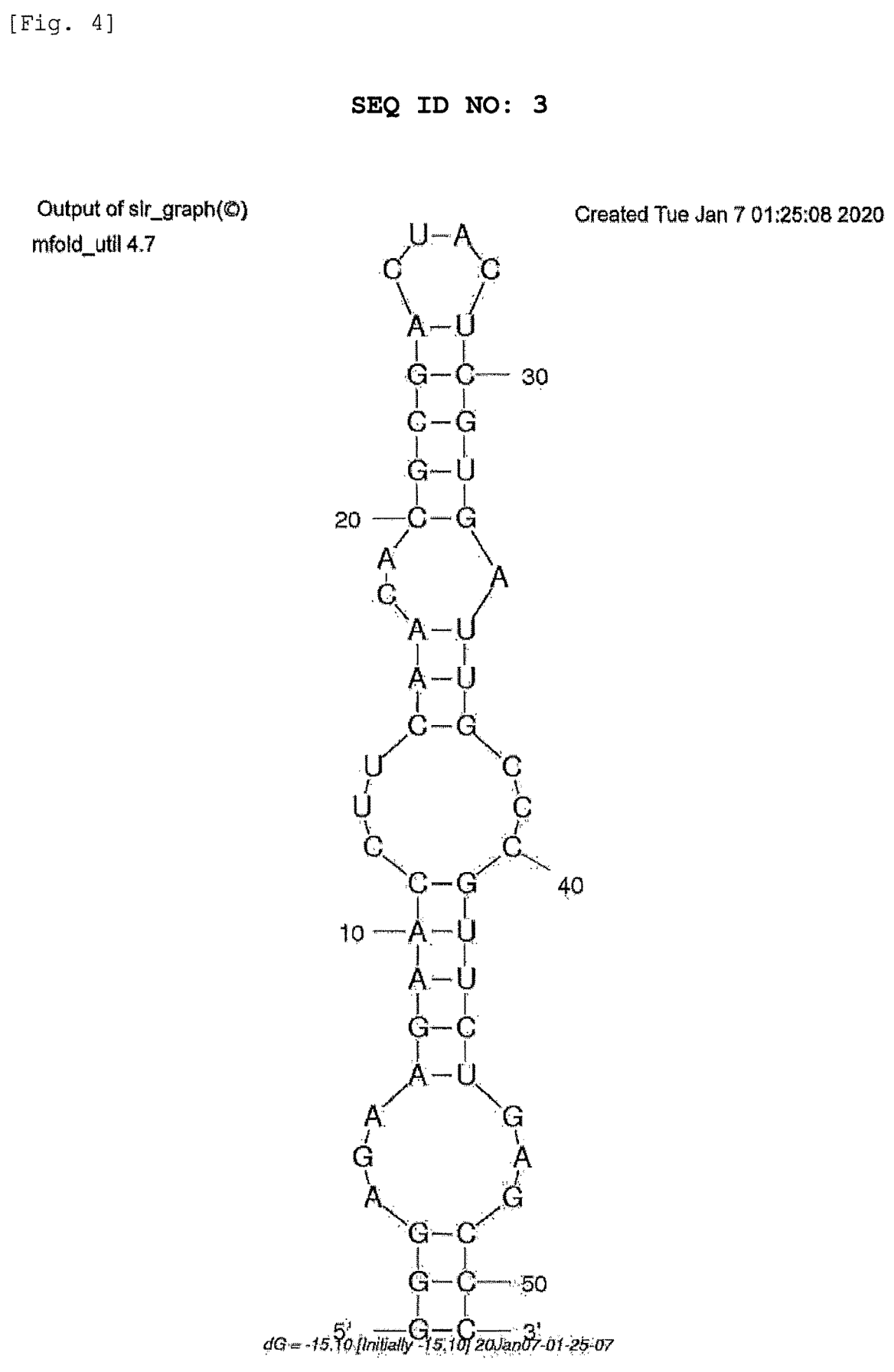
Figure 4:
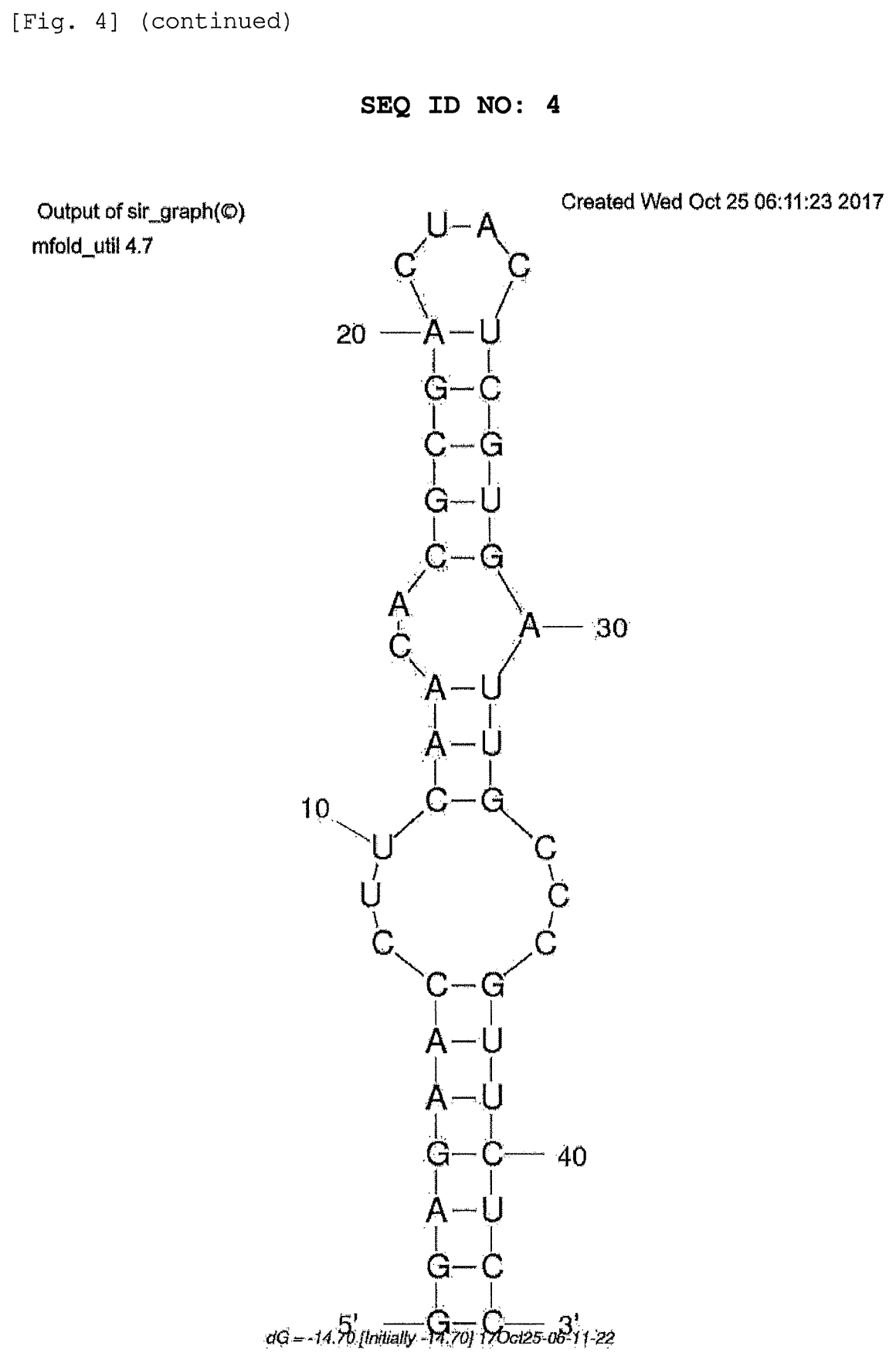
Figure 4:
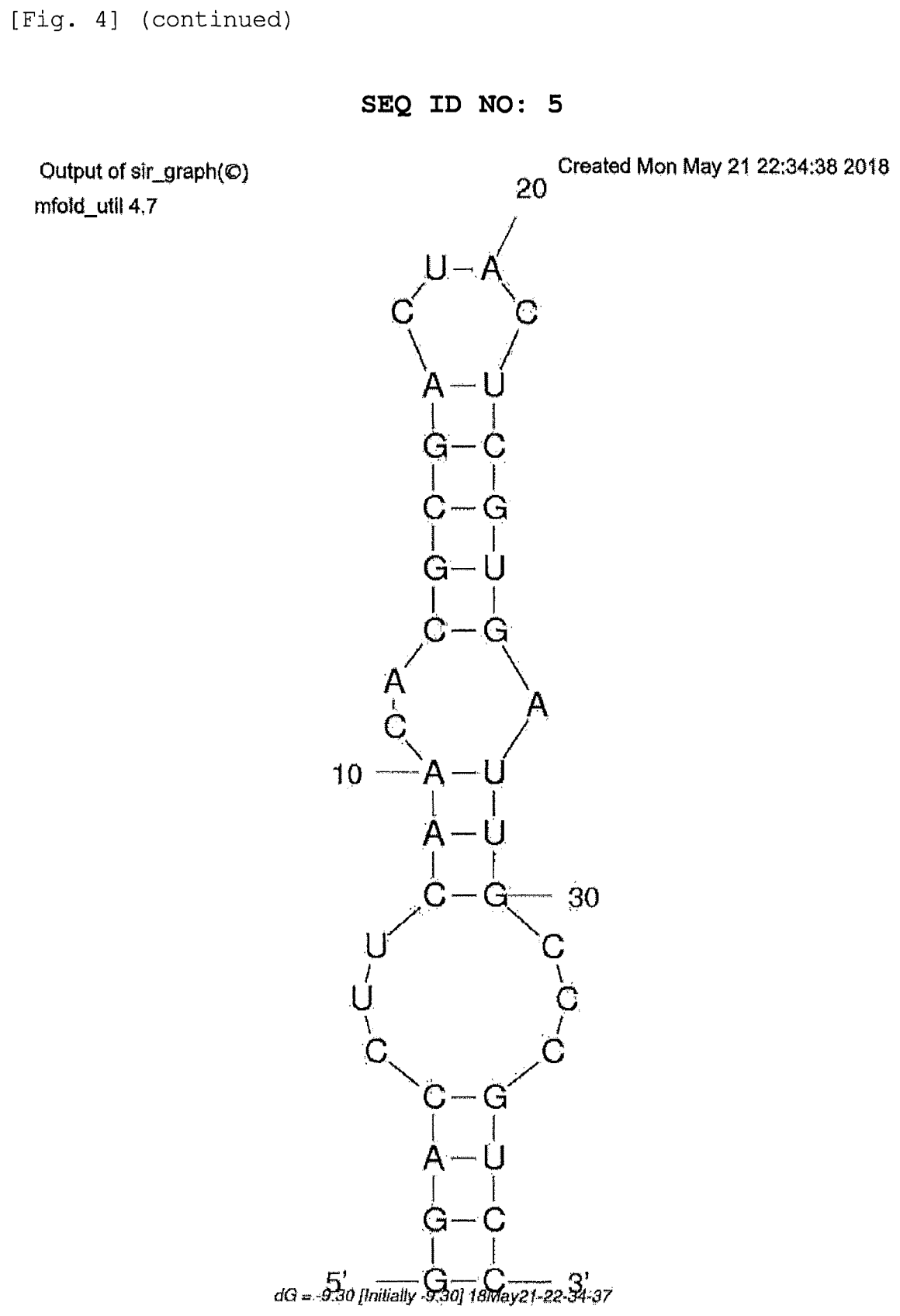
Figure 4:
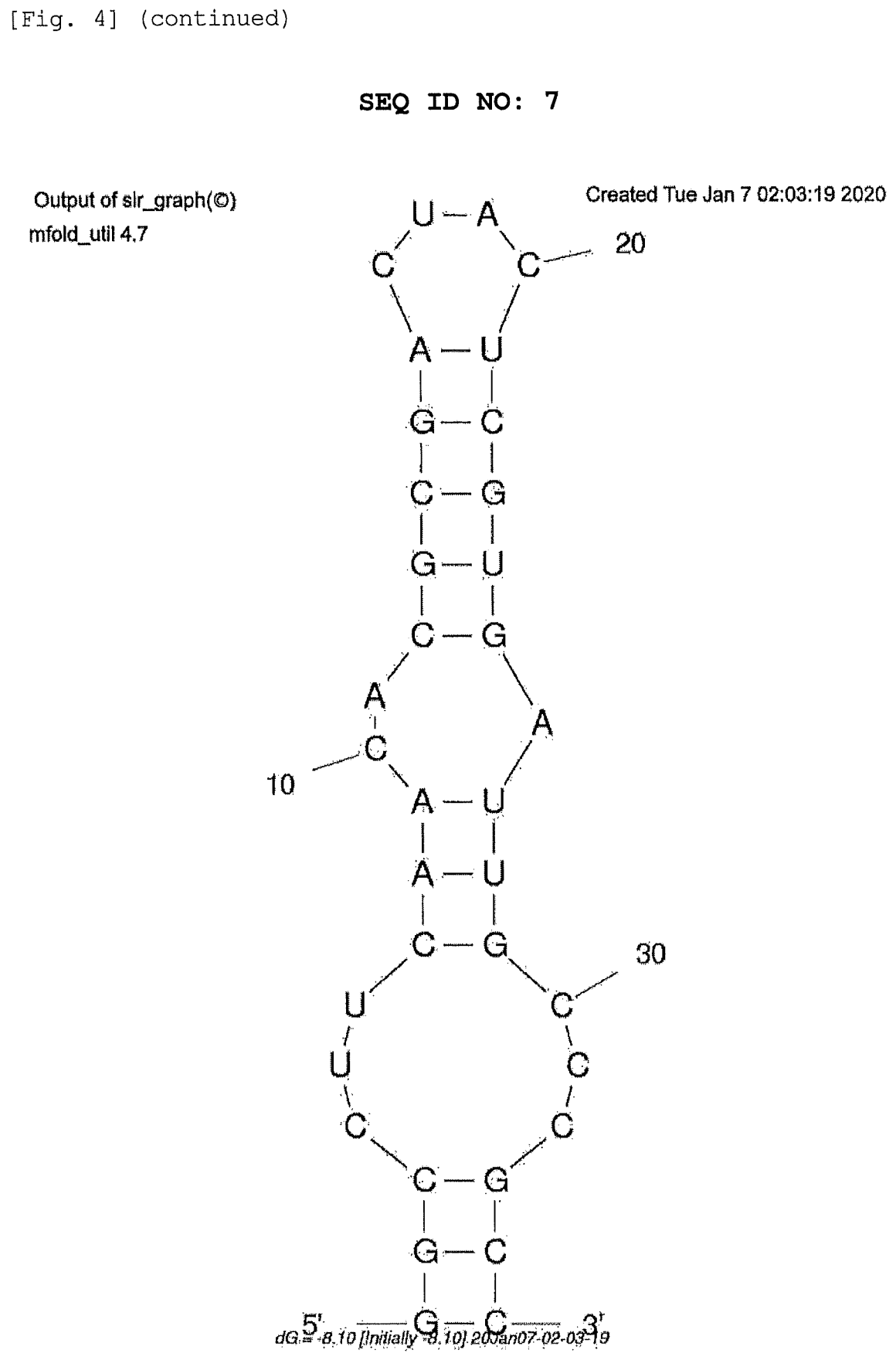

The secondary structure predictions of the aptamers represented by SEQ ID NOs: 3 to 5 and 7 that showed inhibitory activity in the cell assay system are shown in FIG. 4. These results show that even if the aptamer represented by SEQ ID NO: 1 is shortened to 37 bases by deleting the terminal side, the activity can be maintained. In addition, from the results of the aptamer represented by SEQ ID NO: 7, it was shown that the 37-base aptamer represented by SEQ ID NO: 5 can be shortened to 35 bases by deleting the AU base pairs consisting of the 3rd and 35th bases.

On the other hand, from the results of the aptamer represented by SEQ ID NO: 8, it was shown that substitution of CG base pairs consisting of bases in the common sequence with AU base pairs drastically reduces the activity. Furthermore, from the results of the aptamers represented by SEQ ID NOs: 9 to 19 in which one of the bases in the common sequence was deleted, it was shown that deletion of even one base from the common sequence portion drastically reduces the inhibitory activity. Therefore, this example demonstrates the importance of the common sequence portion.

Example 3: Study of Alteration and Terminal Modification of Aptamer—(1)

In order to increase the nuclease resistance of the aptamer represented by SEQ ID NO: 4 (the 2'-position of the ribose of the pyrimidine nucleotide is fluorinated), altered aptamers were prepared by adding idT to the 3'-terminal and introducing a 2'-O-methyl group. The modified sequences are shown in SEQ ID NOs: 4(1) to 4(13).

In addition, in order to examine whether the aptamer can be modified at the 5'-terminal, modified forms of each of SEQ ID NOs: 4, 5 and further-shortened sequences of SEQ ID NO:5 were prepared by adding PEG to the 5'-terminal. These are shown in SEQ ID NOs: 4(14), 5(1), 20, and 21.

The nucleotide sequences and their modification of each aptamer represented by SEQ ID NOs: 4(1)-4(14), 5(1), 20, and 21 are shown below. Unless otherwise stated, the individual sequences listed below are shown in the direction of from 5' to 3', and large letters indicate RNA. Parentheses in nucleotide show modification of the 2'-position of ribose, F shows fluorine atom, and M shows O-methyl group. idT at the end of the sequence indicates modification with inverted-dT and PEG indicates modification with 40 kDa branched polyethylene glycol. The underline in each sequence indicates a common sequence (corresponding to formula (2), formula (1) and formula (3) in this order from the 5'-terminal side, and [ ] indicates a base with introduction of modification and mutation in the SEQ ID NO: thereof, such as introduction of 2'-O-methyl modification.

SEQ ID NO: 4(1) (sequence obtained by adding idT to the 3'-terminal of the sequence represented by SEQ ID NO: 4):

GG<u>AGAAC(F)C(F)U(F)U(F)C(F)AAC(F)AC(F)GC(F)GAC(F)U</u>

<u>(F)AC(F)U(F)C(F)GU(F)GAU(F)U(F)GC(F)C(F)C(F)GU</u>(F)U (F)C(F)U(F)C(F)C(F)-idT

SEQ ID NO: 4(2) (sequence obtained by introducing 2'-O-methyl modification into one site and adding idT to the 3'-terminal of the sequence represented by SEQ ID NO: 4):

GG<u>AGAAC(F)C(F)U(F)U(F)C(F)[A(M)]AC(F)AC(F)GC(F)GAC</u>

<u>(F)U(F)AC(F)U(F)C(F)GU(F)GAU(F)U(F)GC(F)C(F)C(F)GU</u>

(F)U(F)C(F)U(F)C(F)C(F)-idT

SEQ ID NO: 4(3) (sequence obtained by introducing 2'-O-methyl modification into one site and adding idT to the 3'-terminal of the sequence represented by SEQ ID NO: 4):

GG<u>AGAAC(F)C(F)U(F)U(F)C(F)A[A(M)]C(F)AC(F)GC(F)GAC</u>

<u>(F)U(F)AC(F)U(F)C(F)GU(F)GAU(F)U(F)GC(F)C(F)C(F)GU</u>

(F)U(F)C(F)U(F)C(F)C(F)-idT

SEQ ID NO: 4(4) (sequence obtained by introducing 2'-O-methyl modification into one site and adding idT to the 3'-terminal of the sequence represented by SEQ ID NO: 4):

GG<u>AGAAC(F)C(F)U(F)U(F)C(F)AAC(F)[A(M)]C(F)GC(F)GAC</u>

<u>(F)U(F)AC(F)U(F)C(F)GU(F)GAU(F)U(F)GC(F)C(F)C(F)GU</u>

(F)U(F)C(F)U(F)C(F)C(F)-idT

SEQ ID NO: 4(5) (sequence obtained by introducing 2'-O-methyl modification into one site and adding idT to the 3'-terminal of the sequence represented by SEQ ID NO: 4):

GGAGAAC(F)C(F)U(F)U(F)C(F)AAC(F)AC(F)[G(M)]C(F)GAC (F)U(F)AC(F)U(F)C(F)GU(F)GAU(F)U(F)GC(F)C(F)C(F)GU (F)U(F)C(F)U(F)C(F)C(F)-idT

SEQ ID NO: 4(6) (sequence obtained by introducing 2'-O-methyl modification into one site and adding idT to the 3'-terminal of the sequence represented by SEQ ID NO: 4):

GGAGAAC(F)C(F)U(F)U(F)C(F)AAC(F)AC(F)GC(F)[G(M)]AC (F)U(F)AC(F)U(F)C(F)GU(F)GAU(F)U(F)GC(F)C(F)C(F)GU (F)U(F)C(F)U(F)C(F)C(F)-idT

SEQ ID NO: 4(7) (sequence obtained by introducing 2'-O-methyl modification into one site and adding idT to the 3'-terminal of the sequence represented by SEQ ID NO: 4):

GGAGAAC(F)C(F)U(F)U(F)C(F)AAC(F)AC(F)GC(F)G[A(M)]C (F)U(F)AC(F)U(F)C(F)GU(F)GAU(F)U(F)GC(F)C(F)C(F)GU (F)U(F)C(F)U(F)C(F)C(F)-idT

SEQ ID NO: 4(8) (sequence obtained by introducing 2'-O-methyl modification into one site and adding idT to the 3'-terminal of the sequence represented by SEQ ID NO: 4):

GGAGAAC(F)C(F)U(F)U(F)C(F)AAC(F)AC(F)GC(F)GAC(F)U (F)[A(M)]C(F)U(F)C(F)GU(F)GAU(F)U(F)GC(F)C(F)C(F)G U(F)U(F)C(F)U(F)C(F)C(F)-idT

SEQ ID NO: 4(9) (sequence obtained by introducing 2'-O-methyl modification into one site and adding idT to the 3'-terminal of the sequence represented by SEQ ID NO: 4):

GGAGAAC(F)C(F)U(F)U(F)C(F)AAC(F)AC(F)GC(F)GAC(F)U (F)AC(F)U(F)C(F)[G(M)]U(F)GAU(F)U(F)GC(F)C(F)C(F)G U(F)U(F)C(F)U(F)C(F)C(F)-idT

SEQ ID NO: 4(10) (sequence obtained by introducing 2'-O-methyl modification into one site and adding idT to the 3'-terminal of the sequence represented by SEQ ID NO: 4):

GGAGAAC(F)C(F)U(F)U(F)C(F)AAC(F)AC(F)GC(F)GAC(F)U (F)AC(F)U(F)C(F)GU(F)[G(M)]AU(F)U(F)GC(F)C(F)C(F)G U(F)U(F)C(F)U(F)C(F)C(F)-idT

SEQ ID NO: 4(11) (sequence obtained by introducing 2'-O-methyl modification into one site and adding idT to the 3'-terminal of the sequence represented by SEQ ID NO: 4):

GGAGAAC(F)C(F)U(F)U(F)C(F)AAC(F)AC(F)GC(F)GAC(F)U (F)AC(F)U(F)C(F)GU(F)G[A(M)]U(F)U(F)GC(F)C(F)C(F)G U(F)U(F)C(F)U(F)C(F)C(F)-idT

SEQ ID NO: 4(12) (sequence obtained by introducing 2'-O-methyl modification into one site and adding idT to the 3'-terminal of the sequence represented by SEQ ID NO: 4):

GGAGAAC(F)C(F)U(F)U(F)C(F)AAC(F)AC(F)GC(F)GAC(F)U (F)AC(F)U(F)C(F)GU(F)GAU(F)U(F)[G(M)]C(F)C(F)C(F)G U(F)U(F)C(F)U(F)C(F)C(F)-idT

SEQ ID NO: 4(13) (sequence obtained by introducing 2'-O-methyl modification into one site and adding idT to the 3'-terminal of the sequence represented by SEQ ID NO: 4):

GGAGAAC(F)C(F)U(F)U(F)C(F)AAC(F)AC(F)GC(F)GAC(F)U (F)AC(F)U(F)C(F)GU(F)GAU(F)U(F)GC(F)C(F)C(F)[G(M)] U(F)U(F)C(F)U(F)C(F)C(F)-idT

SEQ ID NO: 4(14) (sequence obtained by adding PEG to the 5'-terminal and idT to the 3'-terminal of the sequence represented by SEQ ID NO: 4):

PEG-GGAGAAC(F)C(F)U(F)U(F)C(F)AAC(F)AG(F)GC(F)GAC (F)U(F)AC(F)U(F)C(F)GU(F)GAU(F)U(F)GC(F)C(F)C(F)GU (F)U(F)C(F)U(F)C(F)C(F)-idT

SEQ ID NO: 5(1) (sequence obtained by adding PEG to the 5'-terminal and idT to the 3'-terminal of the sequence represented by SEQ ID NO: 5):

PEG-GGAC(F)C(F)U(F)U(F)C(F)AAC(F)AC(F)GC(F)GAC(F)U (F)AC(F)U(F)C(F)GU(F)GAU(F)U(F)GC(F)C(F)C(F)GU(F)C (F)C(F)-idT

SEQ ID NO: 20 (sequence obtained by shortening the sequence represented by SEQ ID NO: 5 to 35 bases by deleting GC base pair consisting of respective terminal bases, and adding PEG to the 5'-terminal and idT to the 3'-terminal):

PEG-GAC(F)C(F)U(F)U(F)C(F)AAC(F)AC(F)GC(F)GAC(F)U (F)AC(F)U(F)C(F)GU(F)GAU(F)U(F)GC(F)C(F)C(F)GU(F)C (F)-idT

SEQ ID NO: 21 (sequence obtained by shortening the sequence represented by SEQ ID NO: 20 to 33 bases by deleting GC base pair consisting of respective terminal bases, and adding PEG to the 5'-terminal and idT to the 3'-terminal):

PEG-AC(F)C(F)U(F)U(F)C(F)AAC(F)AC(F)GC(F)GAC(F)U (F)AC(F)U(F)C(F)GU(F)GAU(F)U(F)GC(F)C(F)C(F)GU(F)- idT

Whether these aptamers bind to human IL-21 and inhibit the function thereof was evaluated by preparing the aptamers by chemical synthesis and using a method similar to that in Example 1. The evaluation of inhibition in the cell assay system was performed at nucleic acid final concentrations of 1 nM and 0.2 nM. The results thereof are shown in Table 3. In the Table, "++" in the binding activity in Biacore indicates that the binding amount (RU value) of the aptamer to human IL-21 immobilized on CM4 chip is 100 or more. The "+" in the inhibitory activity indicates inhibition of 40% or more at 1 nM and 15% or more at 0.2 nM, and "-" indicates a failure to meet the criteria. In the Table, "n.d." indicates unmeasured.

TABLE 3

| SEQ ID NO: | length | binding activity in Biacore | inhibitory rate (%) in cell assay system | | inhibitory activity |
|---|---|---|---|---|---|
| | | | 1 nM aptamer | 0.2 nM aptamer | |
| 4 (1) | 43 | ++ | 69.3 | 28.6 | + |
| 4 (2) | 43 | n.d. | 63.6 | 28.9 | + |
| 4 (3) | 43 | n.d. | 79.7 | 43.2 | + |
| 4 (4) | 43 | n.d. | 69.5 | 23.8 | + |
| 4 (5) | 43 | n.d. | 67.4 | 28.4 | + |
| 4 (6) | 43 | n.d. | 49.7 | 18.3 | + |
| 4 (7) | 43 | n.d. | 22.0 | 2.3 | − |
| 4 (8) | 43 | ++ | 81.1 | 47.4 | + |
| 4 (9) | 43 | n.d. | 72.3 | 29.5 | + |
| 4 (10) | 43 | n.d. | 73.0 | 40.0 | + |
| 4 (11) | 43 | n.d. | 72.0 | 39.0 | + |
| 4 (12) | 43 | n.d. | 58.8 | 25.6 | + |
| 4 (13) | 43 | n.d. | 72.3 | 35.6 | + |
| 4 (14) | 43 | ++ | 79.7 | 53.6 | + |
| 5 (1) | 37 | ++ | 86.5 | 62.1 | + |
| 20 | 35 | ++ | 78.9 | 50.9 | + |
| 21 | 33 | ++ | 40.6 | 24.4 | + |

These results indicate that it is possible to add idT to the 3'-terminal of the aptamer of the present invention. The inhibitory activity of the synthetic product of SEQ ID NO: 4 (1) in this Example was higher than the inhibitory activity of the transcript of SEQ ID NO: 4 performed in Example 2. This is considered to be because the chemical synthesis increased the purity of the desired nucleic acid sequence, and the addition of idT improved the resistance to degradation by 3' exonuclease.

From these results, it was also found that, among the aptamers represented by SEQ ID NOs: 4(2) to (13), all aptamers except SEQ ID NO: 4(7) maintain inhibitory activity against human IL-21 and function even when 2'-O-methyl modification is introduced into bases at various sites. SEQ ID NOs: 4(3) and 4(8) showed improved inhibitory activity than the aptamer represented by SEQ ID NO: 4(1).

On the other hand, the aptamer represented by SEQ ID NO: 4(7) in which the third A in the common sequence (CGACUACU: the formula (1)) was 2'-O-methyl-modified showed a reduced inhibitory activity.

The results of the aptamers represented by SEQ ID NOs: 4(14), 5(1), 20 and 21 indicate that PEG modification at the 5'-terminal is possible. The results of the aptamers represented by SEQ ID NOs: 20 and 21 indicate that the inhibitory activity was maintained by 35 bases obtained by deleting one terminal base pair from SEQ ID NO: 5(1), and even 33 bases obtained by deleting two terminal base pairs had the inhibitory activity.

Example 4: Alteration of Aptamer—(2)

In order to increase the nuclease resistance of the aptamer represented by SEQ ID NO: 5 (the 2'-position of the ribose of the pyrimidine nucleotide is fluorinated), altered aptamers were prepared by introducing a 2'-O-methyl group. The nucleotide sequences of the altered aptamers are shown below as SEQ ID NOs: 5(2) to 5(18) with modifications.

In order to optimize sequences, an altered aptamer was prepared by substituting a part of the sequence. The nucleotide sequences of the altered aptamers prepared by sequence substitution are shown below as SEQ ID NO: 22 and 23 with modifications. Unless otherwise stated, the individual sequences listed below are shown in the direction of from 5' to 3', and large letters indicate RNA. Parentheses in nucleotide show modification of the 2'-position of ribose, F shows fluorine atom, and M shows O-methyl group. idT at the end of the sequence indicates modification with inverted-dT. The underline in each sequence indicates a common sequence (corresponding to formula (2), formula (1) and formula (3) in this order from the 5'-terminal side, and [ ] indicates a base with introduction of new modification and mutation in the nearest SEQ ID NO, such as introduction of 2'-O-methyl modification.

SEQ ID NO: 5(2) (sequence obtained by adding idT to the 3'-terminal of the sequence represented by SEQ ID NO: 5):

GGAC(F)C(F)U(F)U(F)C(F)AAC(F)AC(F)GC(F)GAC(F)U(F)

AC(F)U(F)C(F)GU(F)GAU(F)U(F)GC(F)C(F)C(F)GU(F)C(F)

C(F)-idT

SEQ ID NO: 5(3) (sequence obtained by introducing modification into the sequence represented by SEQ ID NO: 5 to reflect the 2'-O-methyl modification of SEQ ID NOs: 4(3), (8) to (11), and (13), and adding idT to the 3'-terminal):

GGAC(F)C(F)U(F)U(F)C(F)A[A(M)]C(F)AC(F)GC(F)GAC(F)

U(F)[A(M)]C(F)U(F)C(F)[G(M)]U(F)[G(M)][A(M)]U(F)U (F)GC(F)C(F)C(F)[G(M)]U(F)C(F)C(F)-idT

SEQ ID NO: 22 (sequence obtained by substituting the 17th A (base in the common sequence) with G in the sequence represented by SEQ ID NO: 5(3)):

GGAC(F)C(F)U(F)U(F)C(F)AA(M)C(F)AC(F)GC(F)G[G]C(F)

U(F)A(M)C(F)U(F)C(F)G(M)U(F)G(M)A(M)U(F)U(F)GC(F)C (F)C(F)G(M)U(F)C(F)C(F)-idT

SEQ ID NO: 5(4) (sequence obtained by introducing modification into the sequence represented by SEQ ID NO: 5(3) to reflect the 2'-O-methyl modification of SEQ ID NO: 4(4)):

GGAC(F)C(F)U(F)U(F)C(F)AA(M)C(F)[A(M)]C(F)GC(F)GAC (F)U(F)A(M)C(F)U(F)C(F)G(M)U(F)G(M)A(M)U(F)U(F)GC (F)C(F)C(F)G(M)U(F)C(F)C(F)-idT

SEQ ID NO: 5(5) (sequence obtained by introducing modification into the sequence represented by SEQ ID NO: 5(4) to reflect the 2'-O-methyl modification of SEQ ID NO: 4(5)):

GGAC(F)C(F)U(F)U(F)C(F)AA(M)C(F)A(M)C(F)[G(M)]C(F)

GAC(F)U(F)A(M)C(F)U(F)C(F)G(M)U(F)G(M)A(M)U(F)U(F)

GC(F)C(F)C(F)G(M)U(F)C(F)C(F)-idT

SEQ ID NO: 5(6) (sequence obtained by introducing modification into the sequence represented by SEQ ID NO: 5(5) to reflect the 2'-O-methyl modification of SEQ ID NO: 4(2)):

GGAC(F)C(F)U(F)U(F)C(F)[A(M)]A(M)C(F)A(M)C(F)G(M)C(F)GAC(F)U(F)A(M)C(F)U(F)C(F)G(M)U(F)G(M)A(M)U(F)U(F)GC(F)C(F)C(F)G(M)U(F)C(F)C(F)-idT

SEQ ID NO: 5(7) (sequence obtained by introducing modification into the sequence represented by SEQ ID NO: 5(6) to reflect the 2'-O-methyl modification of SEQ ID NO: 4(12)):

GGAC(F)C(F)U(F)U(F)C(F)A(M)A(M)C(F)A(M)C(F)G(M)C(F)GAC(F)U(F)A(M)C(F)U(F)C(F)G(M)U(F)G(M)A(M)U(F)U(F)[G(M)]C(F)C(F)C(F)G(M)U(F)C(F)C(F)-idT

SEQ ID NO: 5(8) (sequence obtained by introducing 2'-O-methyl modification into 3 bases (3 base pairs) on the both terminals of the sequence represented by SEQ ID NO: 5(3)):

[G(M)][G(M)][A(M)]C(F)C(F)U(F)U(F)C(F)AA(M)C(F)AC(F)GC(F)GAC(F)U(F)A(M)C(F)U(F)C(F)G(M)U(F)G(M)A(M)U(F)U(F)GC(F)C(F)C(F)G(M)[U(M)][C(M)][C(M)]-idT

SEQ ID NO: 23 (sequence obtained by substituting CG base pair consisting of the 2nd and 36th bases of the sequence represented by SEQ ID NO: 5(8) with AU base pair):

G(M)[A(M)]A(M)C(F)C(F)U(F)U(F)C(F)AA(M)C(F)AC(F)GC(F)GAC(F)U(F)A(M)C(F)U(F)C(F)G(M)U(F)G(M)A(M)U(F)U(F)GC(F)C(F)C(F)G(M)U(M)[U(M)]C(M)-idT

SEQ ID NO: 5(9) (sequence obtained by introducing 2'-O-methyl modification into one site and adding idT to the 3'-terminal of the sequence represented by SEQ ID NO: 5):

GGA[C(M)]C(F)U(F)U(F)C(F)AAC(F)AC(F)GC(F)GAC(F)U(F)AC(F)U(F)C(F)GU(F)GAU(F)U(F)GC(F)C(F)C(F)GU(F)C(F)C(F)-idT

SEQ ID NO: 5(10) (sequence obtained by introducing 2'-O-methyl modification into two sites and adding idT to the 3'-terminal of the sequence represented by SEQ ID NO: 5):

GGAC(F)C(F)U(F)U(F)C(F)AA[C(M)]A[C(M)]GC(F)GAC(F)U(F)AC(F)U(F)C(F)GU(F)GAU(F)U(F)GC(F)C(F)C(F)GU(F)C(F)C(F)-idT

SEQ ID NO: 5(11) (sequence obtained by introducing 2'-O-methyl modification into one site and adding idT to the 3'-terminal of the sequence represented by SEQ ID NO: 5):

GGAC(F)C(F)U(F)U(F)C(F)AAC(F)AC(F)G[C(M)]GAC(F)U(F)AC(F)U(F)C(F)GU(F)GAU(F)U(F)GC(F)C(F)C(F)GU(F)C(F)C(F)-idT

SEQ ID NO: 5(12) (sequence obtained by introducing 2'-O-methyl modification into one site and adding idT to the 3'-terminal of the sequence represented by SEQ ID NO: 5):

GGAC(F)C(F)U(F)U(F)C(F)AAC(F)AC(F)GC(F)GA[C(M)]U(F)AC(F)U(F)C(F)GU(F)GAU(F)U(F)GC(F)C(F)C(F)GU(F)C(F)C(F)-idT

SEQ ID NO: 5(13) (sequence obtained by introducing 2'-O-methyl modification into one site and adding idT to the 3'-terminal of the sequence represented by SEQ ID NO: 5):

GGAC(F)C(F)U(F)U(F)C(F)AAC(F)AC(F)GC(F)GAC(F)[U(M)]AC(F)U(F)C(F)GU(F)GAU(F)U(F)GC(F)C(F)C(F)GU(F)C(F)C(F)-idT

SEQ ID NO: 5(14) (sequence obtained by introducing 2'-O-methyl modification into one site and adding idT to the 3'-terminal of the sequence represented by SEQ ID NO: 5):

GGAC(F)C(F)U(F)U(F)C(F)AAC(F)AC(F)GC(F)GAC(F)U(F)A[C(M)]U(F)C(F)GU(F)GAU(F)U(F)GC(F)C(F)C(F)GU(F)C(F)C(F)-idT

SEQ ID NO: 5(15) (sequence obtained by introducing 2'-O-methyl modification into one site and adding idT to the 3'-terminal of the sequence represented by SEQ ID NO: 5):

GGAC(F)C(F)U(F)U(F)C(F)AAC(F)AC(F)GC(F)GAC(F)U(F)AC(F)U(F)C(F)G[U(M)]GAU(F)U(F)GC(F)C(F)C(F)GU(F)C(F)C(F)-idT

SEQ ID NO: 5(16) (sequence obtained by introducing 2'-O-methyl modification into two sites and adding idT to the 3'-terminal of the sequence represented by SEQ ID NO: 5):

GGAC(F)C(F)U(F)U(F)C(F)AAC(F)AC(F)GC(F)GAC(F)U(F)A

C(F)U(F)C(F)GU(F)GA[U(M)][U(M)]GC(F)C(F)C(F)GU(F)C (F)C(F)-idT

SEQ ID NO: 5(17) (sequence obtained by introducing 2'-O-methyl modification into two sites and adding idT to the 3'-terminal of the sequence represented by SEQ ID NO: 5):

GGAC(F)C(F)U(F)U(F)C(F)AAC(F)AC(F)GC(F)GAC(F)U(F)A

C(F)U(F)C(F)GU(F)GAU(F)U(F)G[C(M)][C(M)]C(F)GU(F)C (F)C(F)-idT

SEQ ID NO: 5(18) (sequence obtained by introducing 2'-O-methyl modification into one site and adding idT to the 3'-terminal of the sequence represented by SEQ ID NO: 5):

GGAC(F)C(F)U(F)U(F)C(F)AAC(F)AC(F)GC(F)GAC(F)U(F)A

C(F)U(F)C(F)GU(F)GAU(F)U(F)GC(F)C(F)[C(M)]GU(F)C (F)C(F)-idT

Whether these aptamers bind to human IL-21 and inhibit the function thereof was evaluated by preparing the aptamers by chemical synthesis and using a method similar to that in Example 1. The evaluation of inhibition in the cell assay system was performed at nucleic acid final concentrations of 1 nM and 0.2 nM. The results thereof are shown in Table 4. In the Table, "++" in the binding in Biacore indicates that the binding amount (RU value) of the aptamer to human IL-21 immobilized on CM4 chip is 100 or more. The "+" in the inhibition indicates inhibition of 40% or more at 1 nM and 15% or more at 0.2 nM, and "-" indicates a failure to meet the criteria. In the Table, "n.d." indicates unmeasured.

TABLE 4

| SEQ ID NO: | length | binding activity in Biacore | inhibitory rate (%) in cell assay system | | inhibitory activity |
| | | | 1 nM aptamer | 0.2 nM aptamer | |
|---|---|---|---|---|---|
| 5 (2) | 37 | ++ | 51.2 | 19.5 | + |
| 5 (3) | 37 | n.d. | 78.6 | 50.3 | + |
| 22 | 37 | n.d. | 86.1 | 63.1 | + |
| 5 (4) | 37 | n.d. | 80.9 | 51.2 | + |
| 5 (5) | 37 | n.d. | 84.1 | 59.0 | + |
| 5 (6) | 37 | n.d. | 83.9 | 56.3 | + |
| 5 (7) | 37 | ++ | 76.5 | 49.0 | + |
| 5 (8) | 37 | n.d. | 80.9 | 55.3 | + |
| 23 | 37 | n.d. | 76.8 | 50.6 | + |
| 5 (9) | 37 | n.d. | 44.3 | 23.2 | + |
| 5 (10) | 37 | n.d. | 56.2 | 32.4 | + |
| 5 (11) | 37 | n.d. | 17.6 | 11.9 | - |
| 5 (12) | 37 | n.d. | 20.1 | 9.5 | - |
| 5 (13) | 37 | n.d. | 31.8 | 14.9 | - |
| 5 (14) | 37 | n.d. | 66.0 | 40.1 | + |
| 5 (15) | 37 | n.d. | 63.8 | 37.1 | + |
| 5 (16) | 37 | n.d. | 52.3 | 29.4 | + |
| 5 (17) | 37 | ++ | 85.8 | 59.8 | + |
| 5 (18) | 37 | n.d. | 13.9 | 8.6 | - |

From the results of the aptamers represented by SEQ ID NOs: 5(3) to 5(7), it was found that the 2'-O-methyl modification introduced into one base each in the aptamers represented by SEQ ID NO: 4 did not affect the inhibitory activity of the aptamers even when introduced in combination, but rather improved the activity. As regards the newly examined 2'-O-methyl modification sites, it was shown that the aptamers represented by SEQ ID NOs: 5(9) to 5(10), and 5(14) to 5(17) maintained or improved the activity.

On the other hand, the inhibitory activity of the aptamers represented by SEQ ID NOs: 5(11) to 5(13) and 5(18) decreased. Combined with the results of Example 3, the activity of the 15th to 19th bases (CGACU) of the aptamer represented by SEQ ID NO: 5 decreased due to the 2'-O-methyl modification. This sequence is a part of the common sequence (CGACUACU: formula (1)), and the results of this Example also showed that the common sequence part is important for the inhibitory activity.

In the aptamer represented by SEQ ID NO: 22, the third A in the common sequence (CGACUACU: formula (1)) of SEQ ID NO: 5 was substituted with G. It was found that this base substitution did not affect the inhibitory activity. In addition, this base substitution changed the secondary structure prediction of the aptamer. The secondary structure prediction of the aptamer represented by SEQ ID NO: 22 is shown in FIG. 5. From the results of the aptamer represented by SEQ ID NO: 23, it was found that substitution of the GC base pair consisting of the 2nd and 36th bases in the sequence represented by SEQ ID NO: 5 with the AU base pair does not affect the activity.

Example 5: Alteration of Aptamer—(3)

In order to increase the nuclease resistance of the aptamer represented by SEQ ID NO: 22, altered aptamers with the introduction of a 2'-O-methyl group and altered aptamers with the substitution of a part of bases from RNA to DNA were prepared. The prepared altered aptamers are shown in SEQ ID NOs: 22(1) to 22(14). Among them, SEQ ID NO: 22(2) was subjected to 5'-terminal PEG modification, and altered aptamers were also prepared by shortening the sequence by 2 bases and performing the same terminal modification. These are shown in SEQ ID NOs: 22(15) and 24.

The respective nucleotide sequences of the aptamers represented by SEQ ID NOs: 22(1) to 22(15), and 24 are shown below with modifications. Unless otherwise stated, the individual sequences listed below are shown in the direction of from 5' to 3', large letters indicate RNA, and small letters indicate DNA. Parentheses in nucleotide show modification of the 2'-position of ribose, F shows fluorine atom, and M shows O-methyl group. idT at the end of the sequence indicates modification with inverted-dT and PEG indicates modification with 40 kDa branched polyethylene glycol. The underline in each sequence indicates a common sequence (corresponding to formula (2), formula (1) and formula (3) in this order from the 5'-terminal side, and [ ] indicates a base with introduction of new modification and mutation in the nearest SEQ ID NO, such as introduction of 2'-O-methyl modification.

SEQ ID NO: 22(1) (sequence obtained by introducing modification into the sequence represented by SEQ ID NO: 22 to reflect the 2'-O-methyl modification of SEQ ID NOs: 5(7), (8), (12), (16), (18), and (20) in combination):

[G(M)][G(M)][A(M)]C(F)C(F)U(F)U(F)C(F)[A(M)]A(M)

[C(M)][A(M)][C(M)][G(M)]C(F)GGC(F)U(F)A(M)[C(M)]U (F)C(F)G(M)[U(M)]G(M)A(M)U(F)U(F)[G(M)][C(M)]

[C(M)]C(F)G(M)[U(M)][C(M)][C(M)]-idT

SEQ ID NO: 22(2) (sequence obtained by introducing modification into the sequence represented by SEQ ID NO: 22(1) to reflect the 2'-O-methyl modification of SEQ ID NOs: 5(9) and (19)):

G(M)G(M)A(M)[C(M)]C(F)U(F)U(F)C(F)A(M)A(M)C(M)A(M)

C(M)G(M)C(F)GGC(F)U(F)A(M)C(M)U(F)C(F)G(M)U(M)G(M)

A(M)[U(M)][U(M)]G(M)C(M)C(M)C(F)G(M)U(M)C(M)C(M)- idT

SEQ ID NO: 22(3) (sequence obtained by fluorinating the 2'-position of the sequence represented by SEQ ID NO: 22(1) and introducing a 2'-O-methyl modification into one position thereof):

G(M)G(M)A(M)C(F)[C(M)]U(F)U(F)C(F)A(M)A(M)C(M)A(M)

C(M)G(M)C(F)GGC(F)U(F)A(M)C(M)U(F)C(F)G(M)U(M)G(M)

A(M)U(F)U(F)G(M)C(M)C(M)C(F)G(M)U(M)C(M)C(M)-idT

SEQ ID NO: 22(4) (sequence obtained by fluorinating bases at the 2'-position of the sequence represented by SEQ ID NO: 22(1) and introducing a 2'-O-methyl modification into one position thereof):

G(M)G(M)A(M)C(F)C(F)[U(M)]U(F)C(F)A(M)A(M)C(M)A(M)

C(M)G(M)C(F)GGC(F)U(F)A(M)C(M)U(F)C(F)G(M)U(M)G(M)

A(M)U(F)U(F)G(M)C(M)C(M)C(F)G(M)U(M)C(M)C(M)-idT

SEQ ID NO: 22(5) (sequence obtained by fluorinating bases at the 2'-position of the sequence represented by SEQ ID NO: 22(1) and introducing a 2'-O-methyl modification into one position thereof):

G(M)G(M)A(M)C(F)C(F)U(F)[U(M)]C(F)A(M)A(M)C(M)A(M)

C(M)G(M)C(F)GGC(F)U(F)A(M)C(M)U(F)C(F)G(M)U(M)G(M)

A(M)U(F)U(F)G(M)C(M)C(M)C(F)G(M)U(M)C(M)C(M)-idT

SEQ ID NO: 22(6) (sequence obtained by fluorinating bases at the 2'-position of the sequence represented by SEQ ID NO: 22(1) and introducing a 2'-O-methyl modification into one position thereof):

G(M)G(M)A(M)C(F)C(F)U(F)U(F)[C(M)]A(M)A(M)C(M)A(M)

C(M)G(M)C(F)GGC(F)U(F)A(M)C(M)U(F)C(F)G(M)U(M)G(M)

A(M)U(F)U(F)G(M)C(M)C(M)C(F)G(M)U(M)C(M)C(M)-idT

SEQ ID NO: 22(7) (sequence obtained by fluorinating bases at the 2'-position of the sequence represented by SEQ ID NO: 22(1) and introducing a 2'-O-methyl modification into one position thereof):

G(M)G(M)A(M)C(F)C(F)U(F)U(F)C(F)A(M)A(M)C(M)A(M)C (M)G(M)C(F)GGC(F)U(F)A(M)C(M)[U(M)]C(F)G(M)U(M)G (M)A(M)U(F)U(F)G(M)C(M)C(M)C(F)G(M)U(M)C(M)C(M)- idT

SEQ ID NO: 22(8) (sequence obtained by fluorinating bases at the 2'-position of the sequence represented by SEQ ID NO: 22(1) and introducing a 2'-O-methyl modification into one position thereof):

G(M)G(M)A(M)C(F)C(F)U(F)U(F)C(F)A(M)A(M)C(M)A(M)C (M)G(M)C(F)GGC(F)U(F)A(M)C(M)U(F)[C(M)]G(M)U(M)G (M)A(M)U(F)U(F)G(M)C(M)C(M)C(F)G(M)U(M)C(M)C(M)- idT

SEQ ID NO: 22(9) (sequence obtained by introducing modification into the sequence represented by SEQ ID NO: 22(2) to reflect the 2'-O-methyl modification of SEQ ID NOs: 22(4), (6), and (8) in combination):

G(M)G(M)A(M)C(M)C(F)[U(M)]U(F)[C(M)]A(M)A(M)C(M)A (M)C(M)G(M)C(F)GGC(F)U(F)A(M)C(M)U(F)[C(M)]G(M)U (M)G(M)A(M)U(M)U(M)G(M)C(M)C(M)C(F)G(M)U(M)C(M)C (M)-idT

SEQ ID NO: 22(10) (sequence obtained by introducing 2'-O-methyl modification into one site of unmodified RNA in the sequence represented by SEQ ID NO: 22(9):

G(M)G(M)A(M)C(M)C(F)U(M)U(F)C(M)A(M)A(M)C(M)A(M)C (M)G(M)C(F)[G(M)]GC(F)U(F)A(M)C(M)U(F)C(M)G(M)U(M)

G(M)A(M)U(M)U(M)G(M)C(M)C(M)C(F)G(M)U(M)C(M)C(M)- idT

SEQ ID NO: 22(11) (sequence obtained by introducing modification into the sequence represented by SEQ ID NO: 22(10) to reflect the 2'-O-methyl modification of SEQ ID NOs: 22(3) and (5) in combination):

G(M)G(M)A(M)C(M)[C(M)]U(M)[U(M)]C(M)A(M)A(M)C(M)A (M)C(M)G(M)C(F)G(M)GC(F)U(F)A(M)C(M)U(F)C(M)G(M)U (M)G(M)A(M)U(M)U(M)G(M)C(M)C(M)C(F)G(M)U(M)C(M)C (M)-idT

SEQ ID NO: 22(12) (sequence obtained by substituting one site of unmodified RNA in the sequence represented by SEQ ID NO: 22(2) with DNA:

G(M)G(M)A(M)C(M)C(F)U(F)U(F)C(F)A(M)A(M)C(M)A(M)C (M)G(M)C(F)[g]GC(F)U(F)A(M)C(M)U(F)C(F)G(M)U(M)G

-continued (M)A(M)U(M)U(M)G(M)C(M)C(M)C(F)G(M)U(M)C(M)C(M)- idT

SEQ ID NO: 22(13) (sequence obtained by substituting one site of unmodified RNA in the sequence represented by SEQ ID NO: 22(2) with DNA:

G(M)G(M)A(M)C(M)C(F)U(F)U(F)C(F)A(M)A(M)C(M)A(M)C (M)G(M)C(F)G[g]C(F)U(F)A(M)C(M)U(F)C(F)G(M)U(M)G (M)A(M)U(M)U(M)G(M)C(M)C(M)C(F)G(M)U(M)C(M)C(M)- idT

SEQ ID NO: 22(14) (sequence obtained by substituting 2 sites of unmodified RNA in the sequence represented by SEQ ID NO: 22(2) with DNA:

G(M)G(M)A(M)C(M)C(F)U(F)U(F)C(F)A(M)A(M)C(M)A(M)C (M)G(M)C(F)[g][g]C(F)U(F)A(M)C(M)U(F)C(F)G(M)U(M)G (M)A(M)U(M)U(M)G(M)C(M)C(M)C(F)G(M)U(M)C(M)C(M)- idT

SEQ ID NO: 22(15) (sequence obtained by adding PEG to the 5'-terminal of the sequence represented by SEQ ID NO: 22(2)):

PEG-G(M)G(M)A(M)C(M)C(F)U(F)U(F)C(F)A(M)A(M)C(M)A (M)C(M)G(M)C(F)GGC(F)U(F)A(M)C(M)U(F)C(F)G(M)U(M)G (M)A(M)U(M)U(M)G(M)C(M)C(M)C(F)G(M)U(M)C(M)C(M)- idT

SEQ ID NO: 24 (sequence obtained by shortening the sequence represented by SEQ ID NO: 22(15) to 35 bases by deleting one base each from the both terminals and performing the same terminal modification):

PEG-G(M)A(M)C(M)C(F)U(F)U(F)C(F)A(M)A(M)C(M)A(M)C (M)G(M)C(F)GGC(F)U(F)A(M)C(M)U(F)C(F)G(M)U(M)G(M)A (M)U(M)U(M)G(M)C(M)C(M)C(F)G(M)U(M)C(M)-idT

Whether these aptamers bind to human IL-21 and inhibit the function thereof was evaluated by preparing the aptamers by chemical synthesis and using a method similar to that in Example 1. The evaluation of inhibition in the cell assay system was performed at nucleic acid final concentrations of 1 nM and 0.2 nM. The results thereof are shown in Table 5. In the Table, "++" in the binding in Biacore indicates that the binding amount (RU value) of the aptamer to human IL-21 immobilized on CM4 chip is 100 or more. The "+" in the inhibition indicates inhibition of 40% or more at 1 nM and 15% or more at 0.2 nM, and "-" indicates a failure to meet the criteria. In the Table, "n.d." indicates unmeasured.

TABLE 5

| SEQ ID NO: | length | binding activity in Biacore | inhibitory rate (%) in cell assay system | | inhibitory activity |
|---|---|---|---|---|---|
| | | | 1 nM aptamer | 0.2 nM aptamer | |
| 22 (1) | 37 | ++ | 100.0 | 100.0 | + |
| 22 (2) | 37 | ++ | 100.0 | 100.0 | + |
| 22 (3) | 37 | ++ | 100.0 | 73.6 | + |
| 22 (4) | 37 | ++ | 100.0 | 92.5 | + |
| 22 (5) | 37 | ++ | 77.5 | 39.5 | + |
| 22 (6) | 37 | ++ | 100.0 | 99.3 | + |
| 22 (7) | 37 | ++ | 10.5 | -7.6 | - |
| 22 (8) | 37 | ++ | 100.0 | 87.7 | + |
| 22 (9) | 37 | + | 84.4 | 50.0 | + |
| 22 (10) | 37 | + | 70.2 | 29.1 | + |
| 22 (11) | 37 | - | -11.5 | n.d. | - |
| 22 (12) | 37 | ++ | 100.0 | 99.7 | + |
| 22 (13) | 37 | ++ | 98.6 | 81.2 | + |
| 22 (14) | 37 | ++ | 90.6 | 60.3 | + |
| 22 (15) | 37 | ++ | 100.0 | 100.0 | + |
| 24 | 35 | ++ | 100.0 | 99.0 | + |

As a result of evaluating the aptamers represented by SEQ ID NOs: 22(1) and 22(2), the inhibitory activity was further improved by combining the 2'-O-methyl modification examined for one base each in Example 4. From the results of the aptamer represented by SEQ ID NO: 22(7), it was found that the activity decreases by 2'-O-methyl modification of the 8th U of the common sequence (CGGCUACU: formula (1)).

Regarding the sequence (CUUC (common sequence: part of formula (2))) studied for modification with the aptamers represented by SEQ ID NOs: 22(3) to 22(6), the activity was not significantly affected by modification of each one base. However, it was found that the introduction of modification into all four bases, such as the aptamer represented by SEQ ID NO: 22(11), resulted in the loss of IL-21-binding activity.

From the results of the aptamers represented by SEQ ID NOs: 22(12) to 22(14), it was found that they function even when the 2nd G and 3rd G of the common sequence (CGGCUACU: the formula (1)) were DNAs.

From the results of the aptamer represented by SEQ ID NO: 22(15), it was found that the PEG modification of the 5'-terminal does not affect the activity and that the aptamer represented by SEQ ID NO: 24 obtained by shortening one base pair at the terminal of this aptamer to 35 bases also maintained the activity.

Example 6: Preparation of RNA Aptamer that Binds Specifically to Human IL-21—(2)

SELEX was performed in the same manner as in Example 1 using a template with random sequence and primer sequence different from those used in Example 1. As a target substance, human IL-21 (manufactured by PeproTech) immobilized on a carrier of NHS-activated Sepharose 4 Fast Flow (manufactured by GE Healthcare) was used. The template and the primer sequences used are shown below. The DNA template and primers were prepared by chemical synthesis. A mutation was introduced into the template DNA based on the sequence of SEQ ID NO:4.

DNA template:

(SEQ ID NO: 51)

5'-GCAGAGCTCGTGCTC(A)(G)(A)(A)(C)(G)(G)(G)(C)(A)

(A)(T)(C)(A)(C)(G)(A)(G)(T)(A)(G)(T)(C)(G)(C)(G)

-continued (T)(G)(T)(T)(G)(A)(A)(G)(G)(T)(T)(C)(T)TCTCACTGTGA

GCCC-3' primer Fwd:

(SEQ ID NO: 52)

5'-TAATACGACTCACTATAGGGCTCACAGTGAGA-3' primer Rev:

(SEQ ID NO: 53)

5'-GCAGAGCTCGTGCTC-3'

The parentheses in the DNA template (SEQ ID NO: 51) indicate the introduction of mutation, and are designed to contain 76% of the nucleotides shown in the parentheses and 8% each of the other three types of nucleotides. Primer Fwd contains the promoter sequence of T7 RNA polymerase.

RNA pool was added to the carrier on which human IL-21 was immobilized, and the mixture was maintained while slowly stirring for 20 min at 37° C. The resin was washed with solution A to remove RNA not bound to human IL-21. Here, solution A is a mixed solution of 145 mM sodium chloride, 5.4 mM potassium chloride, 1.8 mM calcium chloride, 0.8 mM magnesium chloride, 20 mM tris (pH 7.6), and 0.05% Tween20. The RNA bound to human IL-21 was heat treated at 90° C. for 2 min by adding ultrapure water (ELGA water) and recovered from the supernatant thereof. The recovered RNA was amplified by RT-PCR, transcribed using T7 Transcription Kit and used as a pool for the next round. With the above as 1 round, a similar operation was repeatedly performed plural times. From the 4th round, the resin was washed with solution A' (solution obtained by changing 145 mM sodium chloride in solution A to 295 mM sodium chloride) in order to also remove RNA weakly bound to the resin. After completion of SELEX, base sequence analysis was performed using a next-generation sequencer. The Ion PGM™ system (manufactured by Thermo) was used as the next-generation sequencer, and the analysis was performed according to the Thermo Specification.

Figure 6:
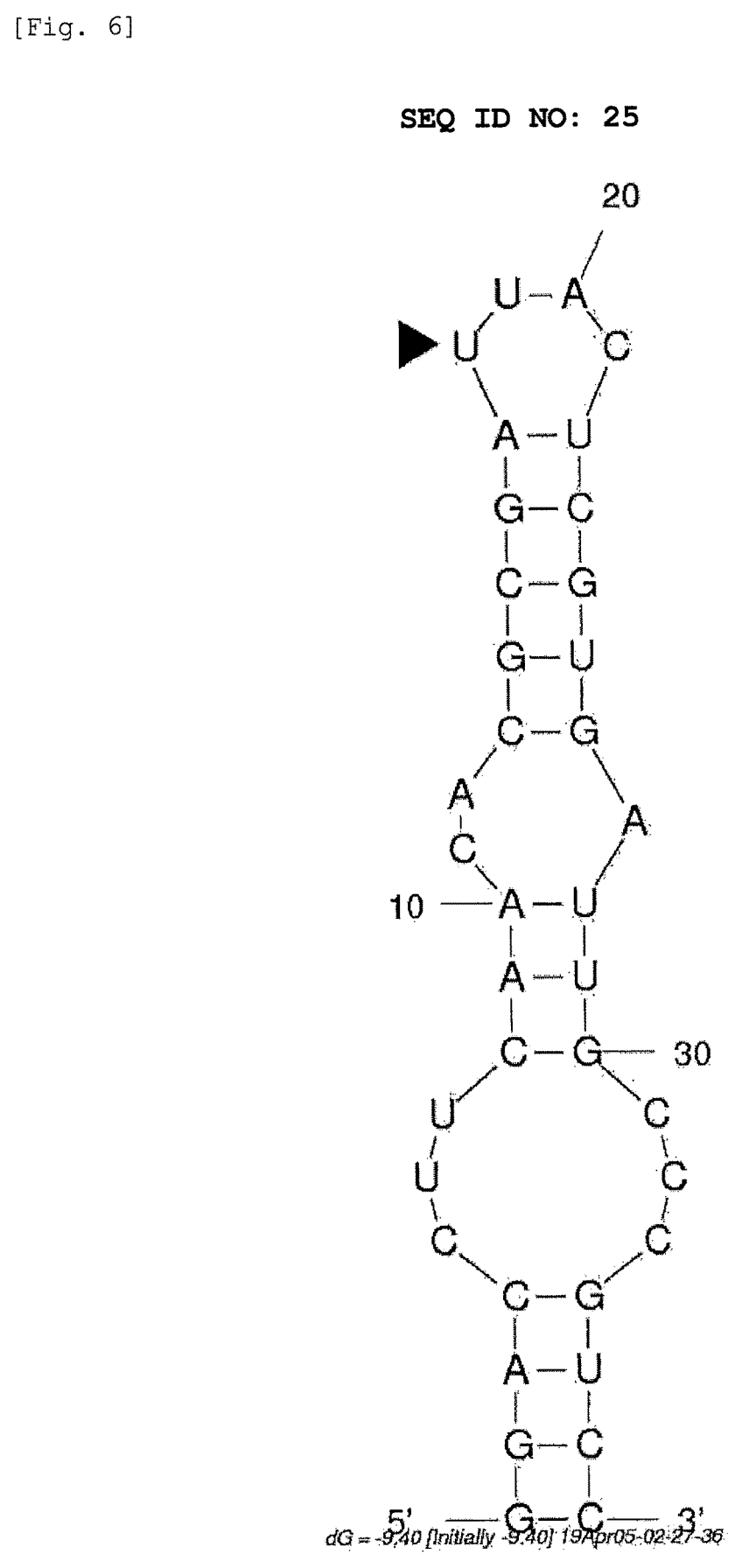
Figure 6:
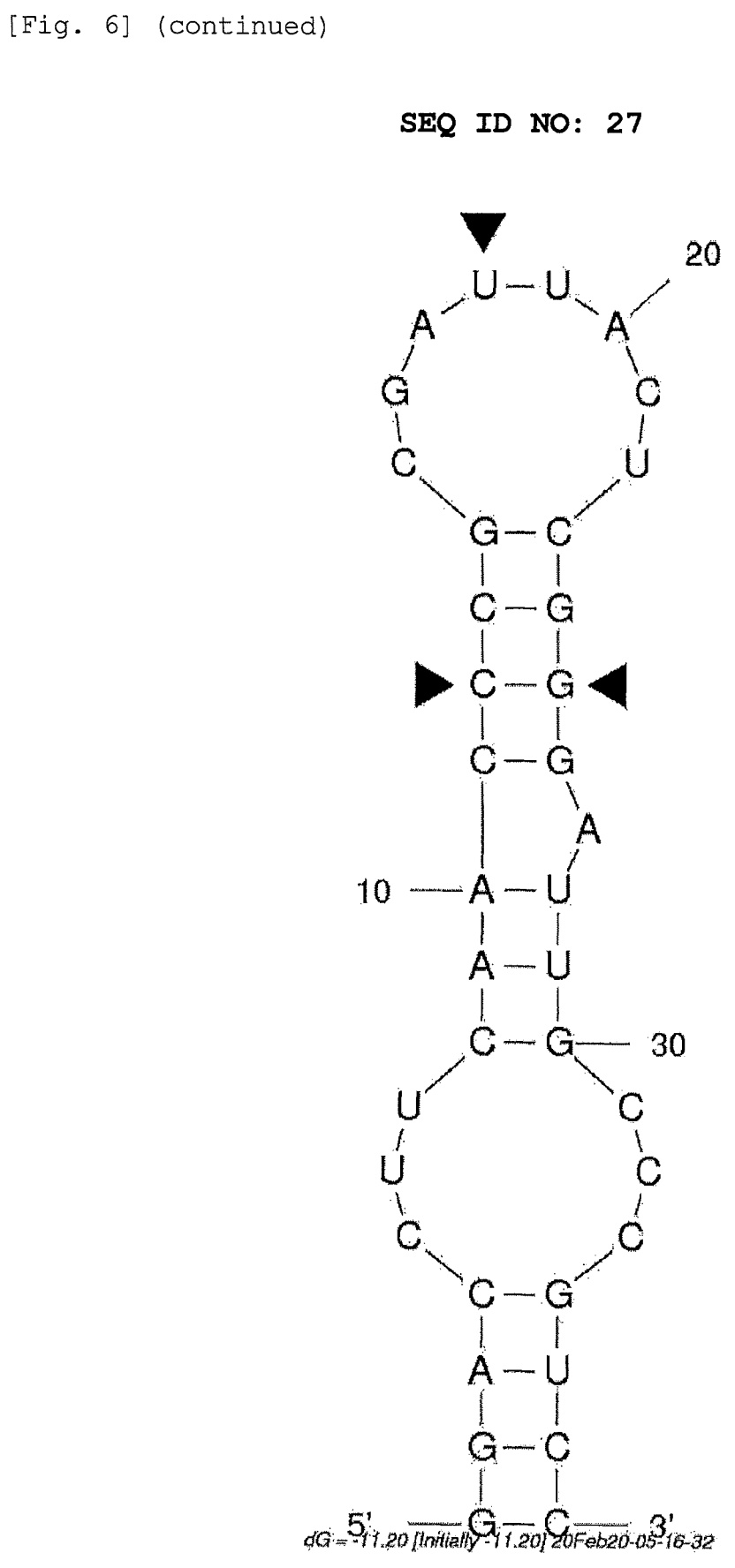
Figure 6:
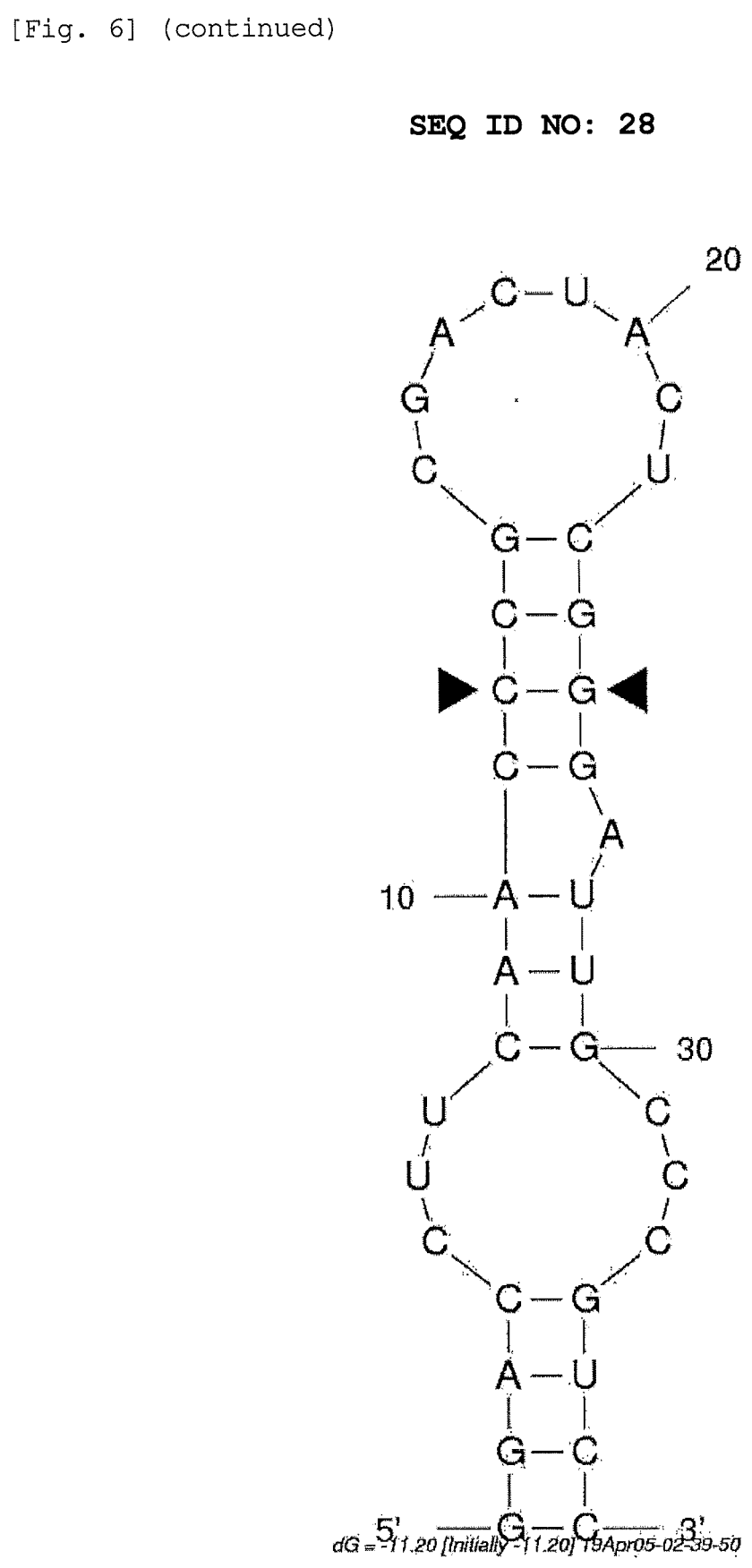
Figure 6:
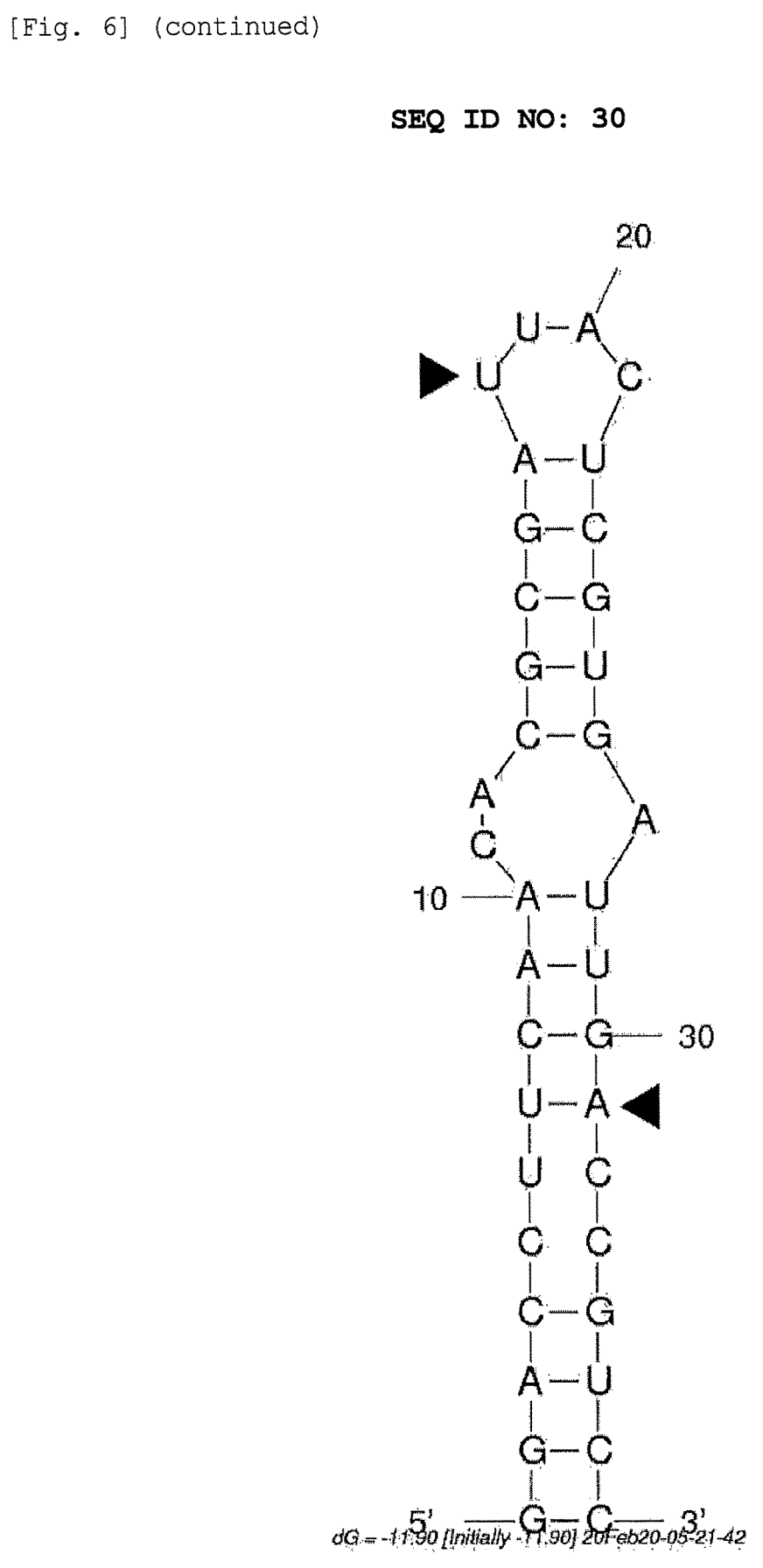
Figure 6:
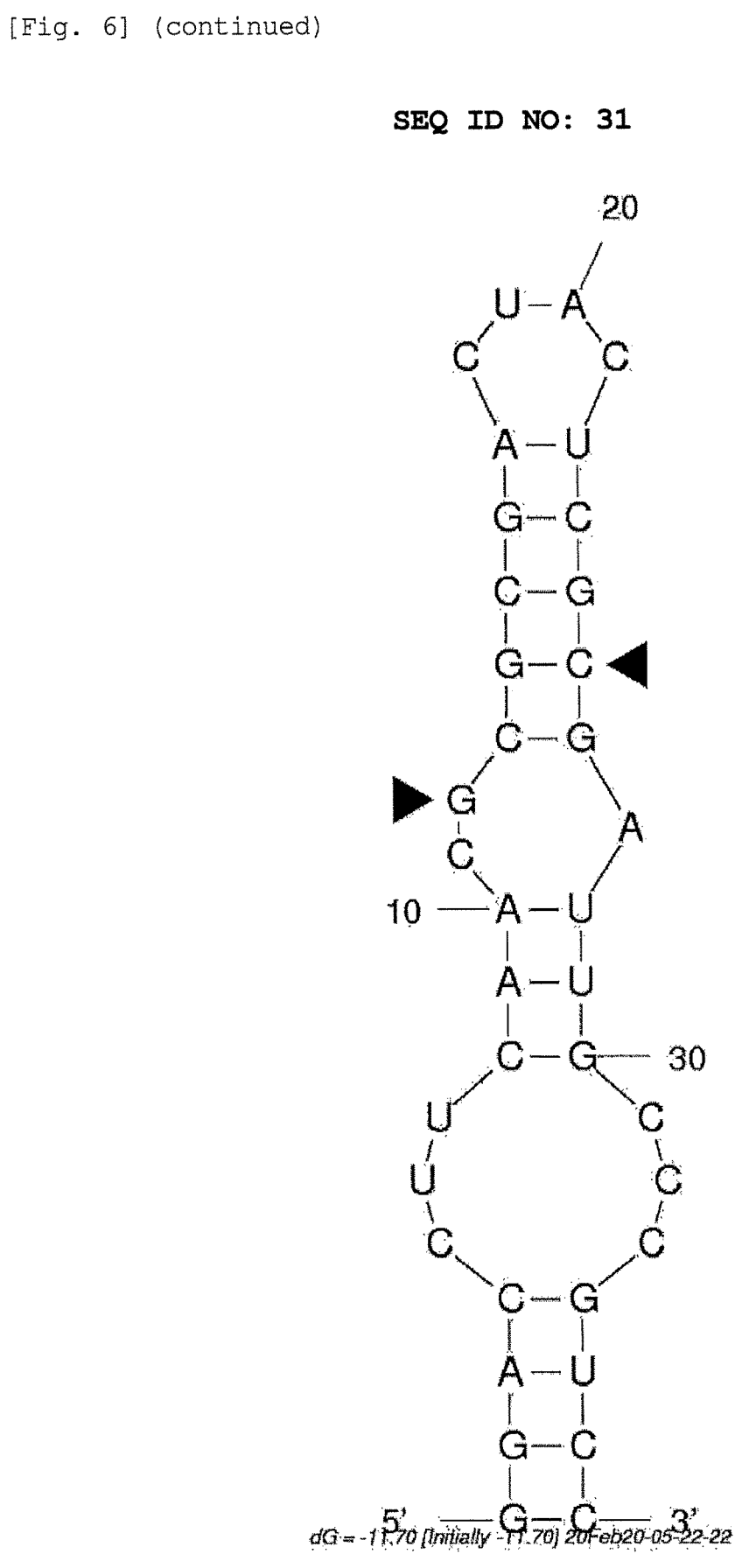
Figure 6:
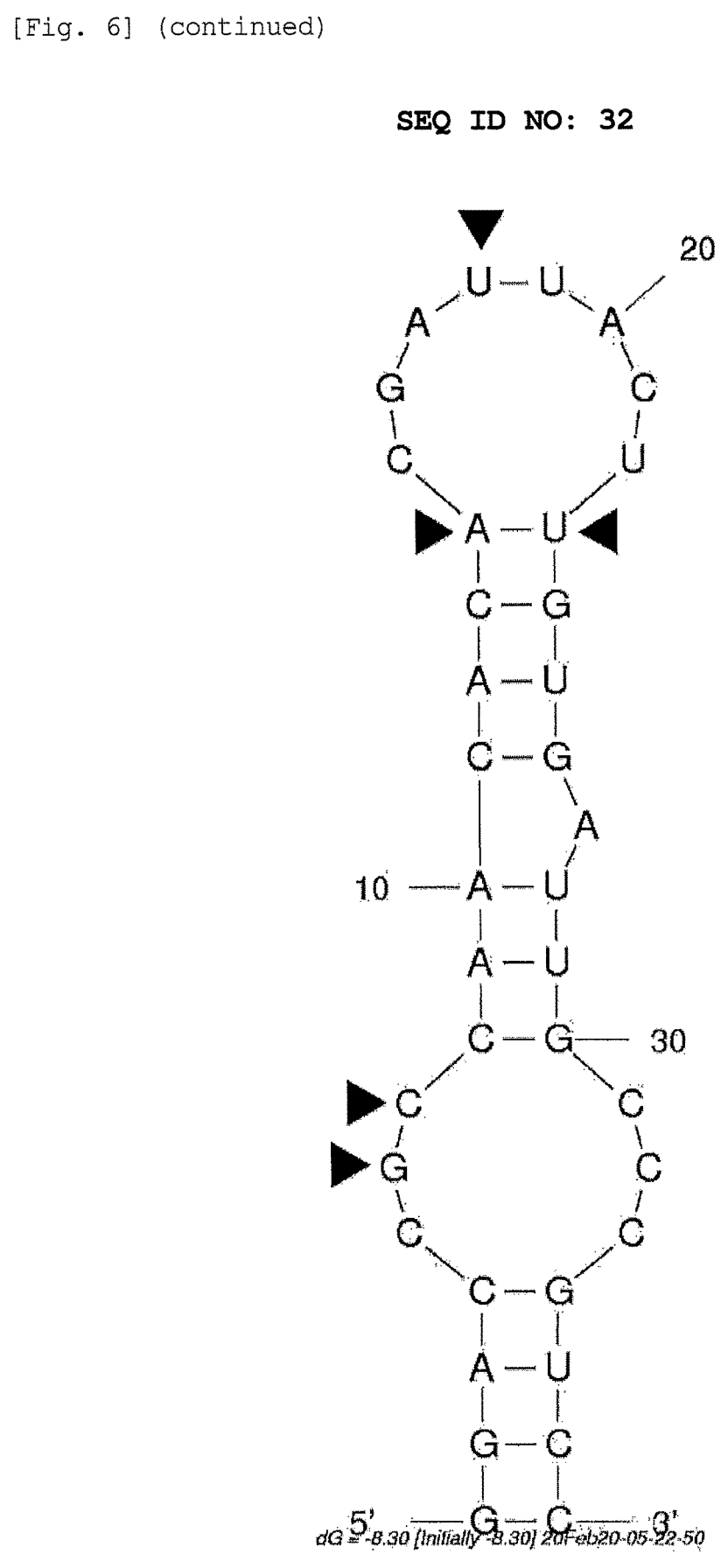
Figure 6:
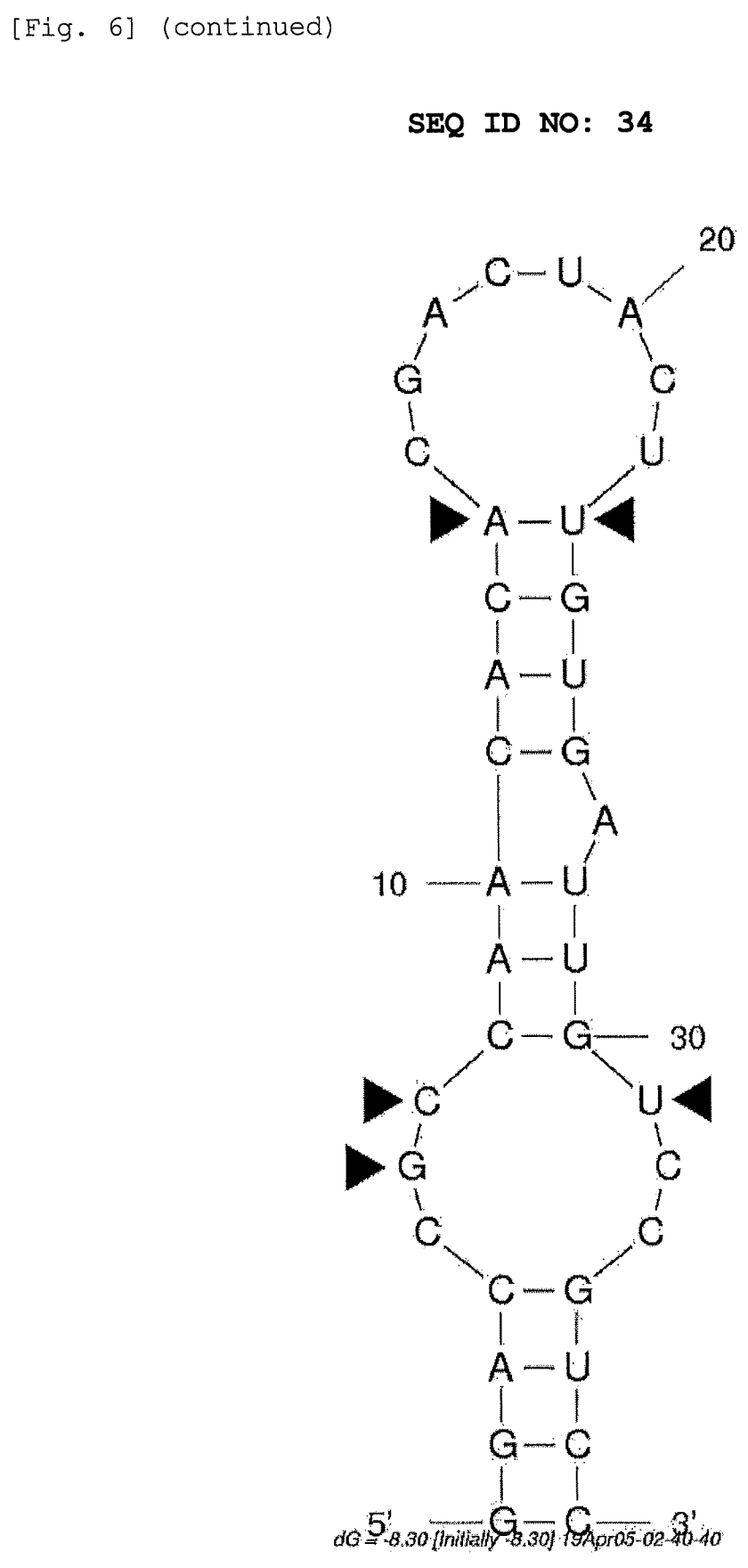
Figure 6:
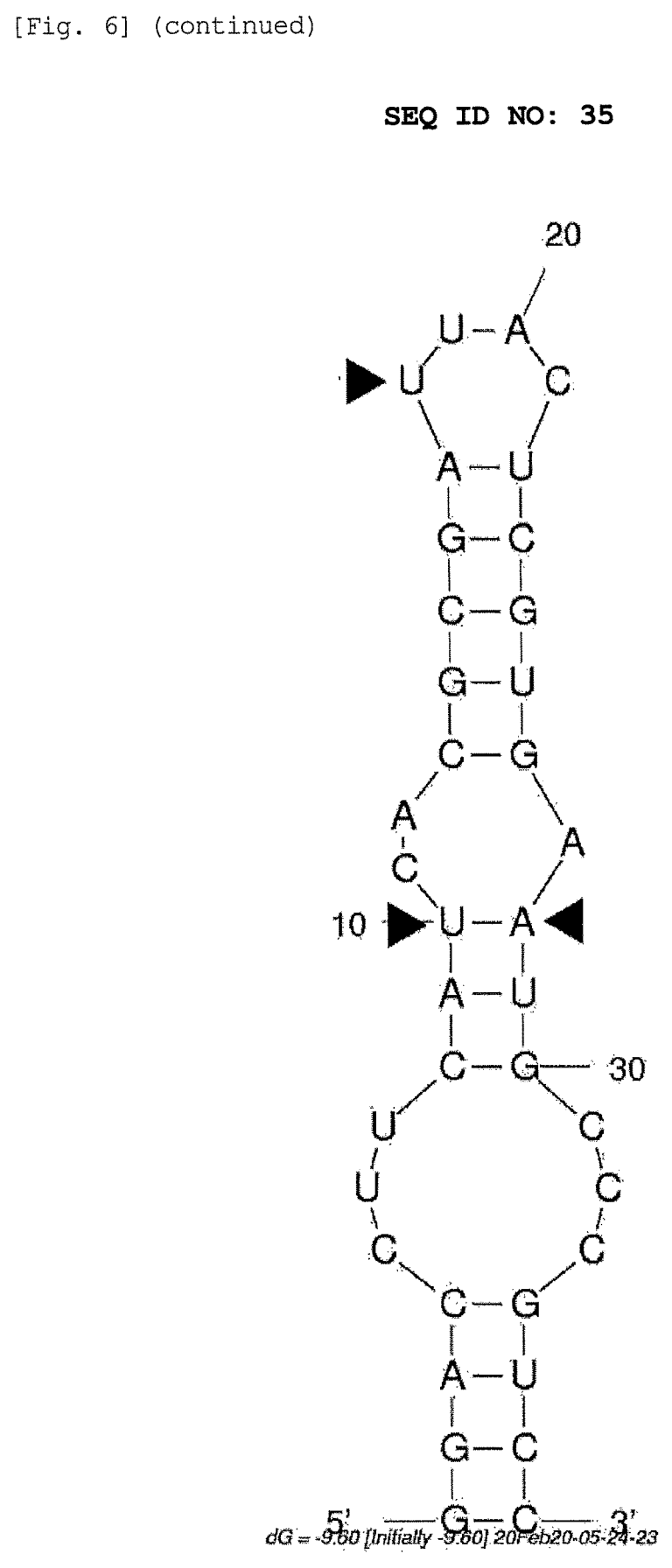

After 6 rounds of SELEX, 546,954 clone sequences were identified by a next-generation sequencer and confirmed to converge to 67,013 types of sequences. At this time, there were 2,765 clones containing the original sequence of SEQ ID NO: 4, and it was the 14th in the number of clones in the whole. The sequences of a part of the analyzed clones are shown in SEQ ID NOs: 25 to 36. The sequences shown here are those obtained by shortening the 69 base sequences obtained by SELEX to 37 bases such that they have the same structure as the sequence of SEQ ID NO:5. The underline in each sequence indicates a common sequence (corresponding to formula (2), formula (1) and formula (3) in this order from the 5'-terminal side. The secondary structure predictions of these clone sequences are shown in FIG. 6. The bases different from SEQ ID NO: 5 are shown with arrows (black triangles).

The respective nucleotide sequences of the aptamers represented by SEQ ID NOs: 25 to 36 are shown below. Unless otherwise stated, the individual sequences listed below are shown in the direction of from 5' to 3'. Purine bases (A and G) are 2'-OH forms, and pyrimidine bases (U and C) are 2'-fluoro-modified forms.

SEQ ID NO: 25:

GGACCUUCAACACGCGAUUACUCGUGAUUGCCCGUCC

SEQ ID NO: 26:

GGACCUUCAACAAGCGAUUACUCUUGAUUGCACGUCC

SEQ ID NO: 27:

GGACCUUCAACCCGCGAUUACUCGGGAUUGCCCGUCC

-continued

SEQ ID NO: 28:

GGACCUUCAACCCGCGACUACUCGGGAUUGCCCGUCC

SEQ ID NO: 29:

GGCCCGCCAACACACGAUUACUUGUGAUUGUCCGGCC

SEQ ID NO: 30:

GGACCUUCAACACGCGAUUACUCGUGAUUGACCGUCC

SEQ ID NO: 31:

GGACCUUCAACGCGCGACUACUCGCGAUUGCCCGUCC

SEQ ID NO: 32:

GGACCGCCAACACACGAUUACUUGUGAUUGCCCGUCC

SEQ ID NO: 33:

GGACCUUCAACCCGCGAUUACUCGGGAUUGCACGUCC

SEQ ID NO: 34:

GGACCGCCAACACACGACUACUUGUGAUUGUCCGUCC

SEQ ID NO: 35:

GGACCUUCAUCACGCGAUUACUCGUGAAUGCCCGUCC

SEQ ID NO: 36:

GGACCGCCAACAAACGAUUACUUUUGAUUGUCCGUCC

Whether these aptamers bind to human IL-21 and inhibit the function thereof was evaluated by a method similar to that in Example 1. Aptamers were obtained by transcription using double-stranded DNA as a template. The evaluation of inhibition in the cell assay system was performed at nucleic acid final concentrations of 30 nM and 10 nM. The results thereof are shown in Table 6. In the Table, "++" in the binding in Biacore indicates that the binding amount (RU value) of the aptamer to human IL-21 immobilized on CM4 chip is 100 or more. The "+" in the binding indicates inhibition of 50% or more at 30 nM and 20% or more at 10 nM, and "-" indicates a failure to meet the criteria.

TABLE 6

| SEQ ID NO: | length | binding activity in Biacore | inhibitory rate (%) in cell assay system | | inhibitory activity |
|---|---|---|---|---|---|
| | | | 30 nM aptamer | 10 nM aptamer | |
| 5 | 37 | ++ | 76.5 | 42.9 | + |
| 25 | 37 | ++ | 64.6 | 27.0 | + |
| 26 | 37 | ++ | 64.8 | 23.9 | + |
| 27 | 37 | ++ | 76.9 | 34.1 | + |
| 28 | 37 | ++ | 92.3 | 68.6 | + |
| 29 | 37 | ++ | 67.4 | 22.9 | + |
| 30 | 37 | ++ | 24.1 | -12.7 | - |
| 31 | 37 | ++ | 74.1 | 25.8 | + |
| 32 | 37 | ++ | 69.3 | 30.1 | + |
| 33 | 37 | ++ | 65.0 | 20.9 | + |
| 34 | 37 | ++ | 92.9 | 62.2 | + |
| 35 | 37 | ++ | 71.4 | 39.8 | + |
| 36 | 37 | ++ | 81.6 | 46.5 | + |

All of the aptamers represented by SEQ ID NOs: 25 to 36 strongly inhibited the function of human IL-21, except for the aptamer represented by SEQ ID NO: 30. As shown in FIG. 6, the same base substitution occurred in multiple clones. In the common sequence (CGACUACU: formula (1)), C was substituted with U at the 4th position in multiple clones. In addition, there were multiple clones in which U at the 3rd and 4th positions in the common sequence (CCUUC: formula (2)) were substituted with G and C, respectively. There was also a clone in which the second C in the common sequence (GCCCG: formula (3)) is substituted with U and the third C is substituted with A. It was found that the internal loop formed by the formula (2) part and the formula (3) part also has sites where base substitution can be made while maintaining the inhibitory activity. Various kinds of base substitutions occurred in the bases of the stem part in each clone, and it was found that various combinations were permissible.

Example 7: Alteration of Aptamer—(4)

In order to increase the nuclease resistance of the aptamer represented by SEQ ID NO: 28, an altered aptamer with the introduction of a 2'-O-methyl group was prepared. After shortening, PEG modification at the 5'-terminal was also performed. The respective nucleotide sequences of the prepared altered aptamers are shown below as SEQ ID NOs: 37, 38, and 38(1) with modifications. Unless otherwise stated, the individual sequences listed below are shown in the direction of from 5' to 3', and large letters indicate RNA. Parentheses in nucleotide show modification of the 2'-position of ribose, F shows fluorine atom, and M shows O-methyl group. idT at the end of the sequence indicates modification with inverted-dT and PEG indicates modification with 40 kDa branched polyethylene glycol. The underline in each sequence indicates a common sequence (corresponding to formula (2), formula (1) and formula (3) in this order from the 5'-terminal side, and [ ] indicates a base with introduction of new modification and mutation in the nearest SEQ ID NO, such as introduction of 2'-O-methyl modification.

SEQ ID NO: 37 (sequence obtained by substituting the 17th A with G in the sequence represented by SEQ ID NO: 28, introducing 2'-O-methyl modification to reflect the modification of the 2'-position of SEQ ID NO: 22(2), and adding idT to the 3'-terminal:

[G(M)][G(M)][A(M)][C(M)]C(F)U(F)U(F)C(F)[A(M)]

[A(M)][C(M)][C(M)][C(M)][G(M)]C(F)G[G]C(F)U(F)

[A(M)][C(M)]U(F)C(F)[G(M)][G(M)][G(M)][A(M)][U(M)]

[U(M)][G(M)][C(M)][C(M)][C(F)][G(M)][U(M)][C(M)]

[C(M)]-idT

SEQ ID NO: 38 (sequence obtained by shortening the sequence represented by SEQ ID NO: 37 to 35 bases by deleting one base each from the both terminals, and adding idT to the 3'-terminal):

G(M)A(M)C(M)C(F)U(F)U(F)C(F)A(M)A(M)C(M)C(M)G (M)C(F)GGC(F)U(F)A(M)C(M)U(F)C(F)G(M)G(M)G(M)A(M)U (M)U(M)G(M)C(M)C(M)C(F)G(M)U(M)C(M)-idT

SEQ ID NO: 38(1) (sequence obtained by adding PEG to the 5'-terminal of the sequence represented by SEQ ID NO: 38):

PEG-G(M)A(M)C(M)C(F)U(F)U(F)C(F)A(M)A(M)C(M)C(M)C (M)G(M)C(F)GGC(F)U(F)A(M)C(M)U(F)C(F)G(M)G(M)G(M)A (M)U(M)U(M)G(M)C(M)C(M)C(F)G(M)U(M)C(M)-idT

Whether these aptamers bind to human IL-21 and inhibit the function thereof was evaluated by preparing the aptamers by chemical synthesis and using a method similar to that in Example 1. In the Table, "++" in the binding activity in Biacore indicates that the binding amount (RU value) of the aptamer to human IL-21 immobilized on CM4 chip is 100 or more. The evaluation of inhibition in the cell assay system was performed at nucleic acid final concentrations of 1 nM and 0.2 nM. In addition, in a cell assay system, the aptamer concentration ($IC_{50}$) at which IFN-γ secretion was inhibited by 50% by IL-21 stimulation was determined. The results thereof are Table 7. In the Table, "n.d." indicates unmeasured.

TABLE 7

| SEQ ID NO: | length | binding activity in Biacore | inhibitory rate (%) in cell assay system | | $IC_{50}$ (nM) in cell assay system |
| --- | --- | --- | --- | --- | --- |
| | | | 1 nM aptamer | 0.2 nM aptamer | |
| 37 | 37 | ++ | 100.0 | 100.0 | 0.02 |
| 38 | 35 | ++ | 99.6 | n.d. | n.d. |
| 38 (1) | 35 | ++ | 100.0 | 100.0 | 0.02 |

From the results of the aptamer represented by SEQ ID NO: 37, it was shown in the aptamer represented by SEQ ID NO: 28 that the 17th A can be substituted with G, as in the aptamer represented by SEQ ID NO: 5. It was also found that introduction of 2'-O-methyl modification into bases at various sites does not affect the activity. The results of the aptamers represented by SEQ ID NOs: 38 and 38(1) reveal that the activity was maintained even after shortening to 35 bases, and PEG modification of the 5'-terminal was also possible.

Example 8: Alteration and Terminal Modification of Aptamer—(5)

In order to increase the nuclease resistance of the aptamer represented by SEQ ID NO: 38, an altered aptamer with the substitution of a part of bases with DNA from RNA and an altered aptamer with the introduction of phosphorothioate were prepared. Furthermore, in order to also examine terminal modification, a sequence in which fatty acid was added to the 5'-terminal was prepared. The respective nucleotide sequences of the prepared altered aptamers are shown below as SEQ ID NOs: 38(2) to 38(21) with modifications. Unless otherwise stated, the individual sequences listed below are shown in the direction of from 5' to 3', large letters indicate RNA, and small letters indicate DNA. Parentheses in nucleotide show modification of the 2'-position of ribose, F shows fluorine atom, and M shows O-methyl group. idT at the end of the sequence indicates modification with inverted-dT and PEG indicates modification with 40 kDa branched polyethylene glycol. As the fatty acid modification, Myr indicates myristic acid, and Pal indicates palmitic acid. In the sequences, s indicates that phosphate groups linking nucleotides were phosphorothioate. The underline in each sequence indicates a common sequence (corresponding to formula (2), formula (1) and formula (3) in this order from the 5'-terminal side, and [ ] indicates a base with introduction of new modification and mutation in the nearest SEQ ID NO, such as substitution with DNA.

SEQ ID NO: 38(2) (sequence obtained by substituting one of the bases fluorinated at the 2'-position of the sequence represented by SEQ ID NO: 38 with DNA):

G(M)A(M)C(M)[c]U(F)U(F)C(F)A(M)A(M)C(M)C(M)C(M)G (M)C(F)GGC(F)U(F)A(M)C(M)U(F)C(F)G(M)G(M)G(M)A(M)U (M)U(M)G(M)C(M)C(M)C(F)G(M)U(M)C(M)-idT

SEQ ID NO: 38(3) (sequence obtained by substituting one of the bases fluorinated at the 2'-position of the sequence represented by SEQ ID NO: 38 with DNA):

G(M)A(M)C(M)C(F)[u]U(F)C(F)A(M)A(M)C(M)C(M)C(M)G (M)C(F)GGC(F)U(F)A(M)C(M)U(F)C(F)G(M)G(M)G(M)A(M)U (M)U(M)G(M)C(M)C(M)C(F)G(M)U(M)C(M)-idT

SEQ ID NO: 38(4) (sequence obtained by substituting one of the bases fluorinated at the 2'-position of the sequence represented by SEQ ID NO: 38 with DNA):

G(M)A(M)C(M)C(F)U(F)[u]C(F)A(M)A(M)C(M)C(M)C(M)G (M)C(F)GGC(F)U(F)A(M)C(M)U(F)C(F)G(M)G(M)G(M)A(M)U (M)U(M)G(M)C(M)C(M)C(F)G(M)U(M)C(M)-idT

SEQ ID NO: 38(5) (sequence obtained by substituting one of the bases fluorinated at the 2'-position of the sequence represented by SEQ ID NO: 38 with DNA):

G(M)A(M)C(M)C(F)U(F)U(F)[c]A(M)A(M)C(M)C(M)C(M)G (M)C(F)GGC(F)U(F)A(M)C(M)U(F)C(F)G(M)G(M)G(M)A(M)U (M)U(M)G(M)C(M)C(M)C(F)G(M)U(M)C(M)-idT

SEQ ID NO: 38(6) (sequence obtained by substituting one of the bases fluorinated at the 2'-position of the sequence represented by SEQ ID NO: 38 with DNA):

G(M)A(M)C(M)C(F)U(F)U(F)C(F)A(M)A(M)C(M)C(M)C(M)G (M)[c]GGC(F)U(F)A(M)C(M)U(F)C(F)G(M)G(M)G(M)A(M)U (M)U(M)G(M)C(M)C(M)C(F)G(M)U(M)C(M)-idT

SEQ ID NO: 38(7) (sequence obtained by substituting one of the bases fluorinated at the 2'-position of the sequence represented by SEQ ID NO: 38 with DNA):

G(M)A(M)C(M)C(F)U(F)U(F)C(F)A(M)A(M)C(M)C(M)C(M)G (M)C(F)GG[c]U(F)A(M)C(M)U(F)C(F)G(M)G(M)G(M)A(M)U (M)U(M)G(M)C(M)C(M)C(F)G(M)U(M)C(M)-idT

SEQ ID NO: 38(8) (sequence obtained by substituting one of the bases fluorinated at the 2'-position of the sequence represented by SEQ ID NO: 38 with DNA):

G(M)A(M)C(M)C(F)U(F)U(F)C(F)A(M)A(M)C(M)C(M)C(M)G (M)C(F)GGC(F)[u]A(M)C(M)U(F)C(F)G(M)G(M)G(M)A(M)U (M)U(M)G(M)C(M)C(M)C(F)G(M)U(M)C(M)-idT

SEQ ID NO: 38(9) (sequence obtained by substituting one of the bases fluorinated at the 2'-position of the sequence represented by SEQ ID NO: 38 with DNA):

G(M)A(M)C(M)C(F)U(F)U(F)C(F)A(M)A(M)C(M)C(M)C(M)G (M)C(F)GGC(F)U(F)A(M)C(M)[u]C(F)G(M)G(M)G(M)A(M)U (M)U(M)G(M)C(M)C(M)C(F)G(M)U(M)C(M)-idT

SEQ ID NO: 38(10) (sequence obtained by substituting one of the bases fluorinated at the 2'-position of the sequence represented by SEQ ID NO: 38 with DNA):

G(M)A(M)C(M)C(F)U(F)U(F)C(F)A(M)A(M)C(M)C(M)C(M)G (M)C(F)GGC(F)U(F)A(M)C(M)U(F)[c]G(M)G(M)G(M)A(M)U (M)U(M)G(M)C(M)C(M)C(F)G(M)U(M)C(M)-idT

SEQ ID NO: 38(11) (sequence obtained by substituting one of the bases fluorinated at the 2'-position of the sequence represented by SEQ ID NO: 38 with DNA):

G(M)A(M)C(M)C(F)U(F)U(F)C(F)A(M)A(M)C(M)C(M)C(M)G (M)C(F)GGC(F)U(F)A(M)C(M)U(F)C(F)G(M)G(M)G(M)A(M)U (M)U(M)G(M)C(M)C(M)[c]G(M)U(M)C(M)-idT

SEQ ID NO: 38(12) (sequence obtained by substituting all bases fluorinated at the 2'-position of the sequence represented by SEQ ID NO: 38 with DNA, and adding PEG to the 5'-terminal):

PEG-G(M)A(M)C(M)[c][u][u][c]A(M)A(M)C(M)C(M)C(M)G (M)[c]GG[c][u]A(M)C(M)[u][c]G(M)G(M)G(M)A(M)U(M)U (M)G(M)C(M)C(M)[c]G(M)U(M)C(M)-idT

SEQ ID NO: 38(13) (sequence obtained by introducing phosphorothioate modification into one site of the sequence represented by SEQ ID NO: 38(1)):

PEG-G(M)A(M)C(M)C(F)U(F)U(F)C(F)A(M)A(M)C(M)C(M)C (M)G(M)[C(F)s]GGC(F)U(F)A(M)C(M)U(F)C(F)G(M)G(M)G (M)A(M)U(M)U(M)G(M)C(M)C(M)C(F)G(M)U(M)C(M)-idT

SEQ ID NO: 38(14) (sequence obtained by introducing phosphorothioate modification into one site of the sequence represented by SEQ ID NO: 38(1)):

PEG-G(M)A(M)C(M)C(F)U(F)U(F)C(F)A(M)A(M)C(M)C(M)C (M)G(M)C(F)[Gs]GC(F)U(F)A(M)C(M)U(F)C(F)G(M)G(M)G (M)A(M)U(M)U(M)G(M)C(M)C(M)C(F)G(M)U(M)C(M)-idT

SEQ ID NO: 38(15) (sequence obtained by introducing phosphorothioate modification into one site of the sequence represented by SEQ ID NO: 38(1)):

PEG-G(M)A(M)C(M)C(F)U(F)U(F)C(F)A(M)A(M)C(M)C(M)C (M)G(M)C(F)G[Gs]C(F)U(F)A(M)C(M)U(F)C(F)G(M)G(M)G (M)A(M)U(M)U(M)G(M)C(M)C(M)C(F)G(M)U(M)C(M)-idT

SEQ ID NO: 38(16) (sequence obtained by introducing phosphorothioate modification into two sites of the sequence represented by SEQ ID NO: 38(1)):

```
PEG-G(M)A(M)C(M)C(F)U(F)U(F)C(F)A(M)A(M)C(M)C(M)C (M)G(M)[C(F)s][Gs]GC(F)U(F)A(M)C(M)U(F)C(F)G(M)G (M)G(M)A(M)U(M)U(M)G(M)C(M)C(M)C(F)G(M)U(M)C(M)- idT
```

SEQ ID NO: 38(17) (sequence obtained by introducing phosphorothioate modification into two sites of the sequence represented by SEQ ID NO: 38(1)):

```
PEG-G(M)A(M)C(M)C(F)U(F)U(F)C(F)A(M)A(M)C(M)C(M)C (M)G(M)[C(F)s]G[Gs]C(F)U(F)A(M)C(M)U(F)C(F)G(M)G (M)G(M)A(M)U(M)U(M)G(M)C(M)C(M)C(F)G(M)U(M)C(M)- idT
```

SEQ ID NO: 38(18) (sequence obtained by introducing phosphorothioate modification into two sites of the sequence represented by SEQ ID NO: 38(1)):

```
PEG-G(M)A(M)C(M)C(F)U(F)U(F)C(F)A(M)A(M)C(M)C(M)C (M)G(M)C(F)[Gs][Gs]C(F)U(F)A(M)C(M)U(F)C(F)G(M)G (M)G(M)A(M)U(M)U(M)G(M)C(M)C(M)C(F)G(M)U(M)C(M)- idT
```

SEQ ID NO: 38(19) (sequence obtained by introducing phosphorothioate modification into three sites of the sequence represented by SEQ ID NO: 38(1)):

```
PEG-G(M)A(M)C(M)C(F)U(F)U(F)C(F)A(M)A(M)C(M)C(M)C (M)G(M)[C(F)s][Gs][Gs]C(F)U(F)A(M)C(M)U(F)C(F)G(M)

G(M)G(M)A(M)U(M)U(M)G(M)C(M)C(M)C(F)G(M)U(M)C(M)- idT
```

SEQ ID NO: 38(20) (sequence obtained by adding Myr to the 5'-terminal of the sequence represented by SEQ ID NO: 38):

```
Myr-G(M)A(M)C(M)C(F)U(F)U(F)C(F)A(M)A(M)C(M)C(M)C (M)G(M)C(F)GGC(F)U(F)A(M)C(M)U(F)C(F)G(M)G(M)G(M)A (M)U(M)U(M)G(M)C(M)C(M)C(F)G(M)U(M)C(M)-idT
```

SEQ ID NO: 38(21) (sequence obtained by adding Pal to the 5'-terminal of the sequence represented by SEQ ID NO: 38):

```
Pal-G(M)A(M)C(M)C(F)U(F)U(F)C(F)A(M)A(M)C(M)C(M)C (M)G(M)C(F)GGC(F)U(F)A(M)C(M)U(F)C(F)G(M)G(M)G(M)A (M)U(M)U(M)G(M)C(M)C(M)C(F)G(M)U(M)C(M)-idT
```

Whether these aptamers bind to human IL-21 and inhibit the function thereof was evaluated by preparing the aptamers by chemical synthesis and using a method similar to that in Example 1. The evaluation of inhibition in the cell assay system was performed at nucleic acid final concentrations of 1 nM and 0.1 nM. The results thereof are shown in Table 8.

In the Table, "++" in the binding in Biacore indicates that the binding amount (RU value) of the aptamer to human IL-21 immobilized on CM4 chip is 100 or more. The "+" in the inhibition indicates inhibition of 40% or more at 1 nM and 15% or more at 0.1 nM, and "-" indicates a failure to meet the criteria. In the Table, "n.d." indicates unmeasured.

TABLE 8

| SEQ ID NO: | length | binding activity in Biacore | inhibitory rate (%) in cell assay system | | inhibitory activity |
|---|---|---|---|---|---|
| | | | 1 nM aptamer | 0.1 nM aptamer | |
| 38 | 35 | ++ | 99.6 | 93.0 | + |
| 38 (2) | 35 | ++ | 98.8 | 86.0 | + |
| 38 (3) | 35 | ++ | 97.6 | 81.6 | + |
| 38 (4) | 35 | ++ | 85.0 | 35.4 | + |
| 38 (5) | 35 | ++ | 99.0 | 87.9 | + |
| 38 (6) | 35 | ++ | 98.6 | 87.2 | + |
| 38 (7) | 35 | ++ | 93.1 | 61.1 | + |
| 38 (8) | 35 | ++ | 99.2 | 92.8 | + |
| 38 (9) | 35 | ++ | 87.2 | 43.8 | + |
| 38 (10) | 35 | ++ | 99.0 | 89.2 | + |
| 38 (11) | 35 | ++ | 94.2 | 63.6 | + |
| 38 (12) | 35 | – | n.d. | n.d. | n.d. |
| 38 (13) | 35 | n.d. | 100.0 | 98.0 | + |
| 38 (14) | 35 | n.d. | 100.0 | 100.0 | + |
| 38 (15) | 35 | n.d. | 100.0 | 100.0 | + |
| 38 (16) | 35 | n.d. | 100.0 | 98.0 | + |
| 38 (17) | 35 | n.d. | 100.0 | 96.6 | + |
| 38 (18) | 35 | n.d. | 100.0 | 100.0 | + |
| 38 (19) | 35 | n.d. | 100.0 | 96.4 | + |
| 38 (20) | 35 | ++ | 100.0 | n.d. | + |
| 38 (21) | 35 | ++ | 100.0 | n.d. | + |

All of the aptamers represented by SEQ ID NOs: 38(2) to 38(11) exhibited inhibitory activity against human IL-21, although the inhibitory activity was stronger or weaker. From these results, it was found that the activity can be maintained even if at least one of the bases in which the 2'-position of the aptamer represented by SEQ ID NO: 38 is fluorinated is substituted with DNA. However, the results of the aptamer represented by SEQ ID NO: 38(12) reveal that the binding activity disappears when all sites are substituted with DNA at once. All of the aptamers represented by SEQ ID NOs: 38(13) to 38(19) maintain high inhibitory activity, and it was found that the activity is not affected even if the phosphate group is phosphorothioated in the three sites examined this time.

From the results of the aptamers represented by SEQ ID NOs: 38(20) and 38(21), it was found that modification of the 5'-terminal is not limited to PEG, but can be made with fatty acids and the like.

Example 9: Study of Base Substitution of Aptamer

From the results of the above Examples, the base sequence of the common sequence part is important for inhibiting the function of human IL-21, and it was also found that there are sites where base substitution is possible. Therefore, a sequence was prepared by substituting a part of the common sequence part of the aptamer represented by SEQ ID NO:5. The nucleotide sequences of parts of the prepared base-substituted aptamers are shown below as SEQ ID NOs: 39 to 43 with modifications. Unless otherwise stated, the individual sequences listed below are shown in the direction of from 5' to 3', the purine bases (A and G) are in a 2'-OH form, and pyrimidine bases (U and C) are in a 2'-fluoro modified form. The underline in each sequence indicates a common sequence (corresponding to formula (2), formula (1) and formula (3) in this order from the 5'-terminal side, and indicates base substitution from the sequence represented by SEQ ID NO: 5.

SEQ ID NO: 39 (sequence obtained by substituting the 6th U with G in the sequence represented by SEQ ID NO: 5):

GGACC[G]UCAACACGCGACUACUCGUGAUUGCCCGUCC

SEQ ID NO: 40 (sequence obtained by substituting the 7th U with C in the sequence represented by SEQ ID NO: 5):

GGACCU[C]CAACACGCGACUACUCGUGAUUGCCCGUCC

SEQ ID NO: 41 (sequence obtained by substituting the 19th U with G in the sequence represented by SEQ ID NO: 5):

GGACCUUCAACACGCGAC[G]ACUCGUGAUUGCCCGUCC

SEQ ID NO: 42 (sequence obtained by substituting the 22nd U with C in the sequence represented by SEQ ID NO: 5):

GGACCUUCAACACGCGACUAC[C]CGUGAUUGCCCGUCC

SEQ ID NO: 43 (sequence obtained by substituting the 32nd C with A in the sequence represented by SEQ ID NO: 5):

GGACCUUCAACACGCGACUACUCGUGAUUGC[A]CGUCC

Whether these aptamers bind to human IL-21 and inhibit the function thereof was evaluated by a method similar to that in Example 1. Aptamers were obtained by transcription using double-stranded DNA as a template. The evaluation of inhibition in the cell assay system was performed at a nucleic acid final concentration of 10 nM. The results thereof are shown in Table 9. In the Table, "++" in the binding in Biacore indicates that the binding amount (RU value) of the aptamer to human IL-21 immobilized on CM4 chip is 100 or more. The "+" in the binding indicates inhibition of 20% or more at 10 nM, and "-" indicates a failure to meet the criteria. In the Table, "n.d." indicates unmeasured.

TABLE 9

| SEQ ID NO: | length | binding activity in Biacore | inhibitory rate (%) in cell assay system (10 nM aptamer) | inhibitory activity |
|---|---|---|---|---|
| 5 | 37 | ++ | 62.9 | + |
| 39 | 37 | n.d. | 56.1 | + |
| 40 | 37 | n.d. | 42.0 | + |
| 41 | 37 | n.d. | 32.4 | + |
| 42 | 37 | n.d. | 39.0 | + |
| 43 | 37 | n.d. | 43.7 | + |

All of the aptamers represented by SEQ ID NOs: 39 to 43 inhibited the function of human IL-21, like the aptamer represented by SEQ ID NO:5. From these results, it was found that in the common sequence (CGACUACU: formula (1)), the 5th U can be substituted with G, and the 8th U can be substituted with C. Similarly, it was found that the formula (2) part (CCUUC) may be CCGUC or CCUCC, and the formula (3) part (GCCCG) may be GCACG.

INDUSTRIAL APPLICABILITY

The aptamer of the present invention is useful as a therapeutic or prophylactic medicament, or a diagnostic reagent, a test reagent, or a reagent for pulmonary hypertension. This application is based on a patent application No. 2020-104831 filed in Japan (filing date: Jun. 17, 2020), the contents of which are incorporated in full herein.

The invention claimed is:

1. An aptamer comprising the nucleotide sequence of SEQ ID NOs: 1-5, 7, 20-29, or 31-43 provided that uracil (U) is optionally thymine (T), wherein the nucleotide sequence of SEQ ID NOs: 1-5, 7, 20-29, or 31-43 is represented by the following formulas (1) to (3):

formula (1) is CGRYKACY, formula (2) is CCKYC, formula (3) is GYMCG, wherein formulas (1) to (3) are arranged to comprise the order of formula (2), formula (1), and formula (3) from the 5'-terminal side, wherein R is A or G, Y is C or U, K is G or U, and M is A or C, and wherein the aptamer binds to interleukin-21 and inhibits binding between the interleukin-21 and a interleukin-21 receptor.

2. The aptamer according to claim 1, wherein, at the 1st C in the formula (1), the hydroxy group at the 2'-position of ribose is substituted by a fluoro group.

3. The aptamer according to claim 1 wherein a nucleotide contained in the aptamer, (i) a hydroxy group at the ribose 2'-position of each pyrimidine nucleotide contained in the aptamer is the same or different, and unsubstituted or substituted by an atom or a group selected from the group consisting of a hydrogen atom, a fluorine atom, and a methoxy group, and wherein in the aptamer of (i), (ii) a hydroxy group at the ribose 2'-position of each purine nucleotide contained in the aptamer is the same or different, and unsubstituted or substituted by an atom or a group selected from the group consisting of a hydrogen atom, a methoxy group, and a fluorine atom.

4. The aptamer according to claim 1, wherein, at the C at position 4 in the formula (3): GYMCG, the hydroxy group at the 2'-position of ribose is substituted by a fluoro group.

5. A complex comprising the aptamer according to claim 1 and a functional substance, wherein the functional substance is an affinity substance, a labeling, substance, an enzyme, a drug delivery vehicle, or a drug.

6. A medicament comprising the aptamer according to claim 1.

7. A method for the treatment or prophylaxis of pulmonary hypertension, the method comprising administering the medicament of claim 6 to a subject in need thereof.

\* \* \* \* \*